(12) United States Patent
Melik et al.

(10) Patent No.: US 9,017,305 B2
(45) Date of Patent: Apr. 28, 2015

(54) ELASTOMERIC COMPOSITIONS THAT RESIST FORCE LOSS AND DISINTEGRATION

(75) Inventors: David Harry Melik, Cincinnati, OH (US); Steven Daryl Smith, Fairfield, OH (US); Janet Neton, West Chester, OH (US)

(73) Assignee: The Procter Gamble Company, Cincinatti, OH (US)

(*) Notice: Subject to any disclaimer, the term of this patent is extended or adjusted under 35 U.S.C. 154(b) by 536 days.

(21) Appl. No.: 13/293,590

(22) Filed: Nov. 10, 2011

(65) Prior Publication Data
US 2012/0123370 A1   May 17, 2012

Related U.S. Application Data

(60) Provisional application No. 61/412,843, filed on Nov. 12, 2010.

(51) Int. Cl.
*A61F 13/15*   (2006.01)
*A61L 15/42*   (2006.01)
(Continued)

(52) U.S. Cl.
CPC ....... *A61L 15/42* (2013.01); *A61F 2013/49022* (2013.01); *A61F 13/49009* (2013.01);
(Continued)

(58) Field of Classification Search
CPC ............... A61F 13/49009; A61F 13/49012; A61F 13/49015; A61F 13/49017; A61F 13/4902; A61F 13/49022; A61F 13/49023; A61F 13/49031; A61F 13/49033; A61F 13/49034; A61F 2013/49038; A61F 2013/49039; A61F 13/49041; A61F 13/51322; A61F 2013/51464; A61F 2013/49022; A61F 2013/49023
USPC .......................................... 604/385.24–385.3
See application file for complete search history.

(56) References Cited

U.S. PATENT DOCUMENTS 3,086,242 A   4/1963   Cook et al.
3,139,468 A   6/1964   Wheat
(Continued)

FOREIGN PATENT DOCUMENTS

CH   528285   2/1968
DE   1910911   3/1969
(Continued)

OTHER PUBLICATIONS

*Polymer Handbook*, Third Edition; Wiley Interscience; Section VII pp. 519-559.
(Continued)

*Primary Examiner* — Lynne Anderson
(74) *Attorney, Agent, or Firm* — Richard L. Alexander

(57) ABSTRACT

Embodiments of the present disclosure may provide various properties of slow recovery polymers, films, and laminates that in combination with an hydrogenated block copolymer provide for (1) an order-disorder transition temperature of greater than about 135° C., (2) a hard phase glass transition temperature of greater than about 60° C., (3) a combination of one or more hard block associating ingredients that maintain or increase the glass transition temperature of at least one equivalent hard block polymer of the hydrogenated block copolymer, (4) a force retention factor of greater than about 2, (5) aromatic substitution of either or both the soft block and the hard block, (6) hard blocks with a solubility parameter of greater than about 9.1 $(cal/cm^3)^{1/2}$, and (7) compositions that remain extendable to at least 50% engineering strain after exposure to isopropyl palmitate for 30 hours at room temperature.

20 Claims, 10 Drawing Sheets

(51) Int. Cl.
*A61F 13/514* (2006.01)
*A61L 15/24* (2006.01)
*A61F 13/49* (2006.01)

(52) U.S. Cl.
CPC . *A61F2013/49023* (2013.01); *A61F 13/51464* (2013.01); *A61F 13/4902* (2013.01); *A61L 15/24* (2013.01)

(56) References Cited

U.S. PATENT DOCUMENTS

| | | |
|---|---|---|
| 3,370,630 A | 2/1968 | Gordon et al. |
| 3,587,581 A | 6/1971 | Jones, Sr. |
| 3,592,946 A | 7/1971 | Griffith |
| 3,601,923 A | 8/1971 | Rosenberg |
| 3,639,917 A | 2/1972 | Althouse |
| 3,819,401 A | 6/1974 | Massengale et al. |
| 3,848,594 A | 11/1974 | Buell |
| 3,860,003 A | 1/1975 | Buell |
| 3,911,173 A | 10/1975 | Sprague, Jr. |
| 3,912,565 A | 10/1975 | Koch et al. |
| 3,929,135 A | 12/1975 | Thompson |
| RE28,688 E | 1/1976 | Cook |
| 4,054,616 A | 10/1977 | Miki et al. |
| 4,089,913 A | 5/1978 | Miki et al. |
| 4,116,842 A | 9/1978 | Meier |
| 4,122,134 A | 10/1978 | Miki et al. |
| 4,152,370 A | 5/1979 | Moczygemba |
| 4,169,336 A | 10/1979 | Kuhn |
| 4,248,981 A | 2/1981 | Milkovich et al. |
| 4,248,982 A | 2/1981 | Bi et al. |
| 4,248,984 A | 2/1981 | Bi et al. |
| 4,259,220 A | 3/1981 | Bunnelle et al. |
| 4,324,246 A | 4/1982 | Mullane et al. |
| 4,337,771 A | 7/1982 | Pieniak et al. |
| 4,342,314 A | 8/1982 | Radel et al. |
| 4,346,198 A | 8/1982 | Doak et al. |
| 4,381,781 A | 5/1983 | Sciaraffa et al. |
| 4,412,087 A | 10/1983 | Trepka |
| 4,418,180 A | 11/1983 | Heinz et al. |
| 4,450,026 A | 5/1984 | Pieniak et al. |
| 4,463,045 A | 7/1984 | Ahr et al. |
| 4,515,595 A | 5/1985 | Kievit et al. |
| 4,573,986 A | 3/1986 | Minetola et al. |
| 4,603,155 A | 7/1986 | Muramori et al. |
| 4,609,191 A | 9/1986 | Remme |
| 4,609,518 A | 9/1986 | Curro et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,673,402 A | 6/1987 | Weisman et al. |
| 4,681,580 A | 7/1987 | Reising et al. |
| 4,695,278 A | 9/1987 | Lawson |
| 4,698,242 A | 10/1987 | Salerno |
| 4,699,622 A | 10/1987 | Toussant et al. |
| 4,699,941 A | 10/1987 | Salerno |
| 4,704,115 A | 11/1987 | Buell |
| 4,704,116 A | 11/1987 | Enloe |
| 4,704,434 A | 11/1987 | Kitchen et al. |
| 4,710,189 A | 12/1987 | Lash |
| 4,719,261 A | 1/1988 | Bunnelle et al. |
| 4,720,415 A | 1/1988 | Vander Wielen et al. |
| 4,761,198 A | 8/1988 | Salerno |
| 4,785,996 A | 11/1988 | Ziecker et al. |
| 4,787,897 A | 11/1988 | Torimae et al. |
| 4,795,454 A | 1/1989 | Dragoo |
| 4,808,178 A | 2/1989 | Aziz et al. |
| 4,816,025 A | 3/1989 | Foreman |
| 4,816,094 A | 3/1989 | Pomplun et al. |
| 4,820,590 A | 4/1989 | Hodgson, Jr. et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |
| 4,874,255 A | 10/1989 | Ball et al. |
| 4,888,231 A | 12/1989 | Angstadt |
| 4,892,536 A | 1/1990 | Desmarais et al. |
| 4,894,060 A | 1/1990 | Nestegard |
| 4,900,317 A | 2/1990 | Buell |
| 4,909,803 A | 3/1990 | Aziz et al. |
| 4,938,753 A | 7/1990 | Van Gompel et al. |
| 4,939,208 A | 7/1990 | Lanza et al. |
| 4,940,464 A | 7/1990 | Van Gompel et al. |
| 4,946,527 A | 8/1990 | Battrell |
| 4,946,899 A | 8/1990 | Kennedy et al. |
| 4,963,140 A | 10/1990 | Robertson et al. |
| 4,965,122 A | 10/1990 | Morman |
| 4,968,312 A | 11/1990 | Khan |
| 4,981,747 A | 1/1991 | Morman |
| 4,987,194 A | 1/1991 | Maeda et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,028,646 A | 7/1991 | Miller et al. |
| 5,036,978 A | 8/1991 | Frank et al. |
| 5,037,416 A | 8/1991 | Allen et al. |
| 5,047,484 A | 9/1991 | Tung |
| 5,049,591 A | 9/1991 | Hayashi et al. |
| 5,050,742 A | 9/1991 | Muckenfuhs |
| 5,054,619 A | 10/1991 | Muckenfuhs |
| 5,062,840 A | 11/1991 | Holt et al. |
| 5,085,654 A | 2/1992 | Buell |
| 5,089,558 A | 2/1992 | Hall et al. |
| 5,092,861 A | 3/1992 | Nomura et al. |
| 5,093,384 A | 3/1992 | Hayashi et al. |
| 5,098,776 A | 3/1992 | Kobayashi et al. |
| 5,114,781 A | 5/1992 | Morman |
| 5,116,662 A | 5/1992 | Morman |
| 5,118,762 A | 6/1992 | Chin |
| 5,135,786 A | 8/1992 | Hayashi et al. |
| 5,137,537 A | 8/1992 | Herron et al. |
| 5,139,832 A | 8/1992 | Hayashi et al. |
| 5,145,935 A | 9/1992 | Hayashi |
| 5,147,345 A | 9/1992 | Young et al. |
| 5,149,741 A | 9/1992 | Alper et al. |
| 5,151,092 A | 9/1992 | Buell et al. |
| 5,156,793 A | 10/1992 | Buell et al. |
| 5,156,911 A | 10/1992 | Stewart |
| 5,159,022 A | 10/1992 | Ikematu et al. |
| 5,167,897 A | 12/1992 | Weber et al. |
| 5,171,236 A | 12/1992 | Dreier et al. |
| 5,188,627 A | 2/1993 | Igaue et al. |
| 5,189,110 A | 2/1993 | Ikematu et al. |
| 5,192,301 A | 3/1993 | Kamiya et al. |
| 5,221,274 A | 6/1993 | Buell et al. |
| 5,226,992 A | 7/1993 | Morman |
| 5,234,999 A | 8/1993 | Tung et al. |
| 5,242,436 A | 9/1993 | Weil et al. |
| 5,246,433 A | 9/1993 | Hasse et al. |
| 5,256,736 A | 10/1993 | Trepka et al. |
| 5,260,345 A | 11/1993 | DesMarais et al. |
| 5,269,755 A | 12/1993 | Bodicky |
| 5,270,388 A | 12/1993 | Onishi et al. |
| 5,272,215 A | 12/1993 | Harwood et al. |
| 5,296,184 A | 3/1994 | Wu |
| 5,306,266 A | 4/1994 | Freeland |
| 5,336,545 A | 8/1994 | Morman |
| 5,342,338 A | 8/1994 | Roe |
| 5,344,691 A | 9/1994 | Hanschen et al. |
| 5,358,500 A | 10/1994 | LaVon et al. |
| 5,358,783 A | 10/1994 | Diehl et al. |
| 5,387,207 A | 2/1995 | Dyer et al. |
| 5,387,450 A | 2/1995 | Stewart |
| 5,397,316 A | 3/1995 | LaVon et al. |
| 5,397,318 A | 3/1995 | Dreier |
| 5,429,856 A | 7/1995 | Krueger et al. |
| 5,439,459 A | 8/1995 | Tanji et al. |
| 5,439,966 A | 8/1995 | Graham et al. |
| 5,445,140 A | 8/1995 | Tovey |
| 5,447,508 A | 9/1995 | Numano et al. |
| 5,468,237 A | 11/1995 | Miller et al. |

(56) References Cited

U.S. PATENT DOCUMENTS

| | | |
|---|---|---|
| 5,468,428 A | 11/1995 | Hanschen et al. |
| 5,492,751 A | 2/1996 | Butt, Sr. et al. |
| 5,499,978 A | 3/1996 | Buell et al. |
| 5,506,300 A | 4/1996 | Ward et al. |
| 5,507,736 A | 4/1996 | Clear et al. |
| 5,514,121 A | 5/1996 | Roe et al. |
| 5,518,433 A | 5/1996 | Sneddon |
| 5,518,801 A | 5/1996 | Chappell et al. |
| 5,532,315 A | 7/1996 | Bonekamp et al. |
| 5,536,563 A | 7/1996 | Shah et al. |
| 5,540,671 A | 7/1996 | Dreier |
| 5,540,976 A | 7/1996 | Shawver et al. |
| 5,545,690 A | 8/1996 | Trepka et al. |
| 5,554,142 A | 9/1996 | Dreier et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe et al. |
| 5,591,152 A | 1/1997 | Buell et al. |
| 5,607,760 A | 3/1997 | Roe |
| 5,609,587 A | 3/1997 | Roe |
| 5,620,780 A | 4/1997 | Krueger et al. |
| 5,625,222 A | 4/1997 | Yoneda et al. |
| 5,634,913 A | 6/1997 | Stinger |
| 5,635,191 A | 6/1997 | Roe et al. |
| H1670 H | 7/1997 | Aziz et al. |
| 5,643,588 A | 7/1997 | Roe et al. |
| 5,648,167 A | 7/1997 | Peck |
| 5,653,703 A | 8/1997 | Roe et al. |
| 5,669,897 A | 9/1997 | LaVon et al. |
| 5,691,034 A | 11/1997 | Krueger et al. |
| 5,714,548 A | 2/1998 | Ma et al. |
| 5,719,226 A | 2/1998 | Kegley |
| H1732 H | 6/1998 | Johnson |
| 5,762,641 A | 6/1998 | Bewick-Sonntag et al. |
| 5,814,705 A | 9/1998 | Ward et al. |
| 5,830,203 A | 11/1998 | Suzuki et al. |
| 5,853,864 A | 12/1998 | Bunnelle |
| 5,858,150 A | 1/1999 | Yarusso et al. |
| 5,865,823 A | 2/1999 | Curro |
| 5,889,118 A | 3/1999 | Delgado et al. |
| 5,897,545 A | 4/1999 | Kline et al. |
| 5,899,895 A | 5/1999 | Robles et al. |
| 5,910,546 A | 6/1999 | Trepka et al. |
| 5,916,206 A | 6/1999 | Otsubo et al. |
| 5,934,470 A | 8/1999 | Bauer et al. |
| 5,938,648 A | 8/1999 | LaVon et al. |
| 5,941,864 A | 8/1999 | Roe |
| 5,957,908 A | 9/1999 | Kline et al. |
| 5,968,025 A | 10/1999 | Roe et al. |
| 5,972,519 A | 10/1999 | Niessner et al. |
| 5,977,430 A | 11/1999 | Roe et al. |
| 5,997,520 A | 12/1999 | Ahr et al. |
| 6,004,306 A | 12/1999 | Robles et al. |
| 6,010,490 A | 1/2000 | Freeland et al. |
| 6,013,063 A | 1/2000 | Roe et al. |
| 6,025,071 A | 2/2000 | Cameron et al. |
| 6,031,053 A | 2/2000 | Knoll et al. |
| 6,063,838 A | 5/2000 | Patnode et al. |
| 6,103,814 A | 8/2000 | Vandrongelen et al. |
| 6,107,537 A | 8/2000 | Elder et al. |
| 6,120,487 A | 9/2000 | Ashton |
| 6,120,489 A | 9/2000 | Johnson et al. |
| 6,120,866 A | 9/2000 | Arakawa et al. |
| 6,140,433 A | 10/2000 | Zhang et al. |
| 6,149,637 A | 11/2000 | Allen et al. |
| 6,156,842 A | 12/2000 | Hoenig et al. |
| 6,168,584 B1 | 1/2001 | Allen et al. |
| 6,176,510 B1 | 1/2001 | Masubuchi et al. |
| 6,177,517 B1 | 1/2001 | Guntherberg et al. |
| 6,179,820 B1 | 1/2001 | Fernfors |
| 6,184,285 B1 | 2/2001 | Goodman et al. |
| 6,187,696 B1 | 2/2001 | Lim et al. |
| 6,190,768 B1 | 2/2001 | Turley et al. |
| 6,193,701 B1 | 2/2001 | Van Gompel et al. |
| 6,194,073 B1 | 2/2001 | Li et al. |
| 6,197,889 B1 | 3/2001 | Knoll et al. |
| 6,211,272 B1 | 4/2001 | Hansen et al. |
| 6,235,306 B1 | 5/2001 | Miranda et al. |
| 6,235,847 B1 | 5/2001 | Hoshi et al. |
| 6,245,050 B1 | 6/2001 | Odorzynski et al. |
| 6,265,484 B1 | 7/2001 | Trepka et al. |
| 6,265,485 B1 | 7/2001 | Trepka et al. |
| 6,274,666 B1 | 8/2001 | Dougherty |
| 6,274,685 B2 | 8/2001 | Blok et al. |
| 6,288,149 B1 | 9/2001 | Kroll |
| 6,300,208 B1 | 10/2001 | Talwar et al. |
| 6,310,154 B1 | 10/2001 | Babcock et al. |
| 6,357,499 B1 | 3/2002 | Kralevich, Jr. et al. |
| 6,369,160 B1 | 4/2002 | Knoll et al. |
| 6,372,853 B1 | 4/2002 | Li et al. |
| 6,383,431 B1 | 5/2002 | Dobrin et al. |
| 6,418,848 B1 | 7/2002 | Fujimoto et al. |
| 6,419,798 B1 | 7/2002 | Topolkaraev et al. |
| 6,423,807 B1 | 7/2002 | Oi et al. |
| 6,432,098 B1 | 8/2002 | Kline et al. |
| 6,444,755 B1 | 9/2002 | Deporter et al. |
| 6,455,627 B1 | 9/2002 | De Keyzer et al. |
| 6,476,288 B1 | 11/2002 | Vanrijswijck et al. |
| 6,482,191 B1 | 11/2002 | Roe et al. |
| 6,485,557 B1 | 11/2002 | Swiler |
| 6,521,704 B1 | 2/2003 | Hubbard et al. |
| 6,531,544 B1 | 3/2003 | Vaughan et al. |
| 6,533,987 B2 | 3/2003 | Topolkaraev et al. |
| 6,565,549 B1 | 5/2003 | Allen et al. |
| 6,571,704 B2 | 6/2003 | Fujimoto et al. |
| 6,579,940 B1 | 6/2003 | Dove |
| 6,592,995 B2 | 7/2003 | Topolkaraev et al. |
| 6,593,430 B1 | 7/2003 | Knoll et al. |
| 6,598,637 B2 | 7/2003 | Lechtenböhmer et al. |
| 6,626,879 B1 | 9/2003 | Ashton et al. |
| 6,627,673 B2 | 9/2003 | Topolkaraev et al. |
| 6,635,041 B1 | 10/2003 | Popp et al. |
| 6,648,869 B1 | 11/2003 | Gillies et al. |
| 6,657,000 B1 | 12/2003 | De Keyzer et al. |
| 6,664,309 B2 | 12/2003 | Svenningsen et al. |
| 6,664,436 B2 | 12/2003 | Topolkaraev et al. |
| 6,673,857 B1 | 1/2004 | Knoll et al. |
| H2100 H | 4/2004 | Hansen et al. |
| 6,722,910 B2 | 4/2004 | Kajinuma |
| 6,746,433 B1 | 6/2004 | Shimoe et al. |
| 6,759,454 B2 | 7/2004 | Stephens et al. |
| 6,759,481 B2 | 7/2004 | Tong |
| 6,790,911 B2 | 9/2004 | Perevosnik et al. |
| 6,818,093 B1 | 11/2004 | Taal et al. |
| 6,827,806 B2 | 12/2004 | Uitenbroek et al. |
| 6,844,383 B2 | 1/2005 | Hoshi et al. |
| 6,887,916 B2 | 5/2005 | Zhou et al. |
| 6,933,421 B2 | 8/2005 | Topolkaraev et al. |
| 6,939,906 B2 | 9/2005 | Hoshi et al. |
| 6,946,172 B2 | 9/2005 | Munn et al. |
| 6,967,178 B2 | 11/2005 | Zhou et al. |
| 6,969,441 B2 | 11/2005 | Welch et al. |
| 6,978,486 B2 | 12/2005 | Zhou et al. |
| 7,015,155 B2 | 3/2006 | Zhou et al. |
| 7,056,411 B2 | 6/2006 | Desai et al. |
| 7,074,484 B2 | 7/2006 | Topolkaraev et al. |
| 7,087,287 B2 | 8/2006 | Curro et al. |
| 7,223,261 B2 * | 5/2007 | Mueller et al. ........... 604/385.19 |
| 7,316,840 B2 | 1/2008 | Neculescz et al. |
| 7,316,842 B2 | 1/2008 | Zhou et al. |
| 7,717,893 B2 | 5/2010 | Hird |
| 7,905,872 B2 | 3/2011 | McKiernan |
| 2001/0004689 A1 | 6/2001 | Otsubo |
| 2002/0056384 A1 | 5/2002 | Fujimoto et al. |
| 2002/0096072 A1 | 7/2002 | Fujimoto et al. |
| 2002/0115744 A1 | 8/2002 | Svenningsen et al. |
| 2002/0115772 A1 | 8/2002 | Topolkaraev et al. |
| 2002/0115977 A1 | 8/2002 | Topolkaraev et al. |
| 2002/0143313 A1 | 10/2002 | Tsuji et al. |
| 2002/0147273 A1 | 10/2002 | Patel et al. |
| 2002/0165516 A1 | 11/2002 | Datta et al. |
| 2003/0088228 A1 | 5/2003 | Desai et al. |

(56) References Cited

U.S. PATENT DOCUMENTS

| | | |
|---|---|---|
| 2003/0091807 A1 | 5/2003 | Desai et al. |
| 2003/0111166 A1 | 6/2003 | Uitenbroek et al. |
| 2003/0120240 A1 | 6/2003 | Buell et al. |
| 2003/0233082 A1 | 12/2003 | Kline et al. |
| 2004/0005832 A1 | 1/2004 | Zhou et al. |
| 2004/0005834 A1 | 1/2004 | Zhou et al. |
| 2004/0005835 A1 | 1/2004 | Zhou et al. |
| 2004/0006324 A1 | 1/2004 | Zhou et al. |
| 2004/0013852 A1 | 1/2004 | Curro et al. |
| 2004/0092900 A1 | 5/2004 | Hoffman et al. |
| 2004/0092902 A1 | 5/2004 | Hoffman |
| 2004/0123938 A1 | 7/2004 | Zhou et al. |
| 2004/0127881 A1 | 7/2004 | Stevens et al. |
| 2004/0162536 A1 | 8/2004 | Becker |
| 2004/0162538 A1 | 8/2004 | Mueller |
| 2004/0167486 A1 | 8/2004 | Busam |
| 2004/0181200 A1 | 9/2004 | Desai et al. |
| 2004/0182499 A1 | 9/2004 | Zhou et al. |
| 2004/0193134 A1 | 9/2004 | Mueller et al. |
| 2004/0222553 A1 | 11/2004 | Desai et al. |
| 2004/0236020 A1 | 11/2004 | Tsuji et al. |
| 2005/0095942 A1 | 5/2005 | Mueller |
| 2005/0096416 A1 | 5/2005 | Zhou et al. |
| 2005/0170729 A1 | 8/2005 | Stadelman et al. |
| 2005/0171499 A1 | 8/2005 | Nigam et al. |
| 2005/0177123 A1 | 8/2005 | Catalan |
| 2005/0196612 A1 * | 9/2005 | Flood et al. ............ 428/364 |
| 2005/0211368 A1 | 9/2005 | McGuire |
| 2005/0215963 A1 | 9/2005 | Autran et al. |
| 2005/0215972 A1 | 9/2005 | Roe et al. |
| 2005/0215973 A1 | 9/2005 | Roe et al. |
| 2005/0256476 A1 | 11/2005 | Mirle et al. |
| 2005/0273071 A1 * | 12/2005 | McKiernan et al. ..... 604/385.24 |
| 2005/0273072 A1 * | 12/2005 | Hird et al. .............. 604/385.24 |
| 2006/0003656 A1 | 1/2006 | Morman |
| 2006/0004342 A1 | 1/2006 | Sawyer et al. |
| 2006/0058765 A1 | 3/2006 | Mueller |
| 2006/0078042 A1 | 4/2006 | Lee |
| 2006/0083900 A1 | 4/2006 | Ashraf |
| 2006/0155255 A1 | 7/2006 | Mckiernan et al. |
| 2006/0167434 A1 | 7/2006 | Ashton et al. |
| 2006/0246803 A1 | 11/2006 | Smith et al. |
| 2006/0264858 A1 | 11/2006 | Roe et al. |
| 2007/0037907 A9 | 2/2007 | Zhou et al. |
| 2007/0088307 A1 | 4/2007 | Arizti |
| 2007/0093771 A1 | 4/2007 | Arizti |
| 2007/0191806 A1 | 8/2007 | Mueller |
| 2007/0197993 A1 | 8/2007 | Arizti |
| 2007/0197994 A1 | 8/2007 | Arizti |
| 2007/0280983 A1 | 12/2007 | Strickler et al. |
| 2008/0033388 A1 | 2/2008 | Mueller |
| 2008/0108963 A1 | 5/2008 | Ashton et al. |
| 2008/0195070 A1 | 8/2008 | Ponomarenko |
| 2008/0311419 A1 | 12/2008 | Ramdatt et al. |
| 2009/0134049 A1 | 5/2009 | Melik |

FOREIGN PATENT DOCUMENTS

| | | |
|---|---|---|
| EP | 0119827 | 7/1988 |
| EP | 0316671 | 11/1988 |
| EP | 0433951 | 6/1991 |
| EP | 0591647 | 4/1994 |
| EP | 0597331 | 5/1994 |
| EP | 0451919 | 2/1995 |
| EP | 0650714 | 5/1995 |
| EP | 0703068 | 3/1996 |
| EP | 0847738 | 6/1998 |
| EP | 1351815 | 2/2005 |
| EP | 1013291 | 6/2005 |
| EP | 1226018 | 10/2005 |
| GB | 2997473 | 8/1995 |
| GB | 2287888 | 10/1995 |
| GB | 2328158 | 2/1999 |
| GB | 2329842 | 4/1999 |
| JP | 62241944 | 10/1987 |
| JP | 63238153 | 10/1988 |
| JP | 3160083 | 7/1991 |
| JP | 3160084 | 7/1991 |
| JP | 3239738 | 10/1991 |
| JP | 4153288 | 5/1992 |
| JP | 7157738 | 6/1995 |
| JP | 8060120 | 3/1996 |
| JP | 8060121 | 3/1996 |
| JP | 8277382 | 10/1996 |
| JP | 8281764 | 10/1996 |
| JP | 9291265 | 11/1997 |
| JP | 9302319 | 11/1997 |
| JP | 2000282006 | 5/1999 |
| JP | 11279521 | 10/1999 |
| JP | 2001040302 | 2/2001 |
| JP | 2001279212 | 10/2001 |
| JP | 2001293789 | 10/2001 |
| WO | WO 94/14395 | 7/1994 |
| WO | WO 95/16746 | 6/1995 |
| WO | WO 96/11236 | 4/1996 |
| WO | WO 96/23823 | 8/1996 |
| WO | WO-97/01584 | 1/1997 |
| WO | WO 98/08476 | 3/1998 |
| WO | WO 99/13016 | 3/1999 |
| WO | WO 00/12645 | 3/2000 |
| WO | WO 00/22061 | 4/2000 |
| WO | WO 00/30581 | 6/2000 |
| WO | WO 00/69834 | 11/2000 |
| WO | WO 01/87589 | 11/2001 |
| WO | WO 02/083786 | 10/2002 |
| WO | WO 03/047488 | 6/2003 |
| WO | WO 03/082571 | 10/2003 |
| WO | WO 2006/074481 | 7/2006 |
| WO | WO 2009/066268 | 5/2009 |

OTHER PUBLICATIONS

Ziabicki, *Fundamentals of Fibre Formation*, John Wiley & Sons, New York (1976), Chapter 6.

J.H. Briston, *Plastic Films*, $2^{nd}$ Edition, Longman Inc., New York (1983), pp. 83-85.

I.M. Ward, *Mechanical Properties of Solid Polymers*, Wiley-Interscience, New York (1971), p. 278.

All Office Actions and Responses for U.S. Appl. No. 13/293,555.

All Office Actions and Responses for U.S. Appl. No. 13/293,571.

All Office Actions and Responses for U.S. Appl. No. 13/293,583.

All Office Actions and Responses for U.S. Appl. No. 13/293,604.

All Office Actions and Responses for U.S. Appl. No. 13/293,611.

All Office Actions and Responses for U.S. Appl. No. 13/293,619.

All Office Actions, Responses and Claims for U.S. Appl. No. 13/293,555.

All Office Actions, Responses and Claims for U.S. Appl. No. 13/293,571.

All Office Actions, Responses and Claims for U.S. Appl. No. 13/293,583.

All Office Actions, Responses and Claims for U.S. Appl. No. 13/293,604.

All Office Actions, Responses and Claims for U.S. Appl. No. 13/293,611.

All Office Actions, Responses and Claims for U.S. Appl. No. 13/293,619.

* cited by examiner

ELASTOMERIC COMPOSITIONS THAT RESIST FORCE LOSS AND DISINTEGRATION

CROSS REFERENCE TO RELATED APPLICATIONS

This application claims the benefit of U.S. Patent No. 61/412,843, filed Nov. 12, 2011, which is hereby incorporated by reference in its entirety.

FIELD OF THE INVENTION

This invention is directed to absorbent articles such as diapers, training pants, adult incontinence articles, feminine hygiene articles, and the like comprising a slow recovery stretch laminate.

BACKGROUND OF THE INVENTION

It may be desirable to construct absorptive devices, such as disposable diapers with fasteners, pull-on diapers, training pants, sanitary napkins, pantiliners, incontinence briefs, and the like, with stretch laminates to improve the ease of motion and maintenance of a sustained fit. Furthermore, stretch laminates allow the diaper to accommodate a range of different sized wearers. A diaper may have stretch laminates in a number of its article elements including the waist band, leg cuffs, side panels, elasticized topsheets, backsheet, ears, outercover, and fastening system.

As disclosed in U.S. Pat. No. 7,717,893 and U.S. Pub. No. US 2005-0273071, there is a need for an absorbent product comprising a stretch laminate that retracts slowly upon being released from a stretched state, thus facilitating application and positioning of the product correctly onto the wearer. U.S. Pat. No. 7,717,893 and U.S. Pub. No. US 2005-0273071 further disclose various embodiments of slow recovery polymers, films, and/or laminates for the purpose of meeting said need, as well as meeting various other needs and desires.

A problem that can exist in filling the need for a slow recovery stretch laminate is that the manufacture and packaging of an absorbent article comprising a slow recovery stretch laminate may result in the slow recovery stretch laminate being held under strain while the absorbent article is stored within its distribution package. That is, the slow recovery stretch laminate may not be in its fully relaxed state during storage. This strain lock can lead to a loss in performance as the product ages, for example, a drop in the unload force of the slow recovery stretch laminate at 37° C. which could result in poor fit. Depending on the placement of the slow recovery stretch laminate(s) within an absorbent article and on the particular absorbent article, poor fit can lead to, for example, increased urine or bowel movement leakage during use, sagging or drooping of the absorbent article during use, or increased discomfort in wearing the absorbent article. The level to which the unload force is reduced can depend on the level of strain lock (aging strain), the aging time, and the thermal history of the slow recovery stretch laminate during aging.

Another problem that can exist in filling the need for a slow recovery stretch laminate is that during the use of an absorbent article comprising a slow recovery stretch laminate comprising an elastic member, certain baby oils, lotions, gels, cremes, and the like, that are spread on the wearer's skin before application of the article, may be absorbed to some extent by the elastic member. This absorption may lead to a swelling or breakage of the elastic member and may result in reduced performance. Swelling may lead to (1) a sticky feeling slow recovery stretch laminate that may cause discomfort to the wearer of the absorbent article, and/or (2) a reduction in the unload force of the slow recovery stretch laminate at 37° C., which may result in poor fit and may lead to, for example, increased urine or bowel movement leakage during use, sagging or drooping of the absorbent article during use, and/or increased discomfort in wearing the absorbent article. Breakage of the elastic member may lead to poor fit if it is localized, but if widespread may lead to catastrophic failure of the slow recovery stretch laminate which may lead to the failure of the absorbent article comprising the slow recovery stretch laminate. The degree to which absorption may occur may depend on the particular construction of the slow recovery stretch laminate, for example, on the type and basis weight of the substrate and on the type and basis weight of any adhesive used to join the elastic member to the substrate, as well as where it is located within the absorbent article. For example, the use of a slow recovery stretch laminate as a waist feature or side panel is in an area of an absorbent article that is less likely to encounter residual baby oil, lotions, gels, and the like, as compared to the use of the slow recovery stretch laminate as an elasticized topsheet. It is an object of the present disclosure to provide various embodiments that offer solutions to said problems, while still also meeting the needs and desires of using a slow recovery polymer, film, and/or laminate as disclosed in U.S. Pat. No. 7,717,893 and U.S. Pub. Nos. 2005-0273071, 2006-0155255, 2006-0167434, and 2009-0134049.

Further, it is an object of the present disclosure to provide various embodiments of slow recovery elastomers, films, and laminates comprising an hydrogenated block copolymer useful for overcoming the problems expressed in the previous paragraphs. Still further, it is an object of the present disclosure to provide various properties of slow recovery polymers, films, and laminates that in combination with an hydrogenated block copolymer are useful for overcoming the problems expressed in the previous paragraphs including (1) an order-disorder transition temperature of greater than about 135° C., (2) a hard phase glass transition temperature of greater than about 60° C., (3) a combination of one or more hard block associating ingredients that maintain or increase the glass transition temperature of at least one equivalent hard block polymer of the hydrogenated block copolymer, (4) a force retention factor of greater than about 2, (5) aromatic substitution of either or both the soft block and the hard block, and (6) certain combinations thereof. Additionally, it is an object of the present disclosure to provide various embodiments of slow recovery polymers, films, and laminates that in combination with a block copolymer are useful for overcoming the problems expressed in the previous paragraphs including (1) hard blocks with a solubility parameter of greater than about 9.1 $(cal/cm^3)^{1/2}$, and (2) compositions that remain extendable to at least 50% engineering strain after exposure to isopropyl palmitate for 30 hours at room temperature.

SUMMARY OF THE INVENTION

In response to the problems identified above, the present disclosure provides an embodiment of an absorbent article comprising a topsheet, a backsheet joined with the topsheet, an absorbent core interposed between the topsheet and backsheet, and an article element. The article element may comprise a slow recovery stretch laminate exhibiting an unload force at 37° C. of about 0.16 N/(g/m) or greater, and a percent of initial strain after 15 seconds of recovery at 22° C. of about 10% or greater. Additionally, the slow recovery stretch laminate may comprise an elastic member comprising an hydrogenated block copolymer comprising at least one soft block and at least two hard blocks, and the elastic member may have an order-disorder temperature of greater than about 135° C.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising an hydrogenated block copolymer comprising at least one soft block and at least two hard blocks. Further, the elastic member may comprise one or both of the following: (a) a hard phase having a glass transition temperature of greater than about 60° C.; (b) one or more hard block associating ingredients that, when combined with a polymer that is an equivalent hard block polymer to said at least two hard blocks of said hydrogenated block copolymer, maintain or increase the glass transition temperature of the equivalent hard block polymer.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising an hydrogenated block copolymer comprising at least one soft block and at least two hard blocks. Further, the elastic member may exhibit an order-disorder temperature of greater than about 135° C. and may comprise one or both of the following: (a) a hard phase having a glass transition temperature of greater than about 60° C.; (b) one or more hard block associating ingredients that, when combined with a polymer that is an equivalent hard block polymer to said at least two hard blocks of said hydrogenated block copolymer, maintain or increase the glass transition temperature of the equivalent hard block polymer.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising an hydrogenated block copolymer comprising at least one soft block and at least two hard blocks. Further, the slow recovery stretch laminate may exhibit a force retention factor of greater than about 2 for at least two of the maximum four hold strains.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising a block copolymer comprising at least one soft block and at least two hard blocks, wherein the soft block backbone is hydrogenated. Further, the hydrogenated block copolymer comprises one or both of the following: (a) one or more hard blocks comprising substituted polystyrene; (b) one or more soft blocks comprising substituted polystyrene.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising a block copolymer comprising at least one soft block and at least two hard blocks. Further, the solubility parameter of the at least two hard blocks may be greater than about 9.1 $(cal/cm^3)^{1/2}$.

Further, the present disclosure provides an embodiment of an absorbent article comprising a topsheet, a backsheet joined with the topsheet, an absorbent core interposed between the topsheet and backsheet; and an article element. The article element may comprise a slow recovery stretch laminate exhibiting an unload force at 37° C. of about 0.16 N/(g/m) or greater and a percent of initial strain after 15 seconds of recovery at 22° C. of about 10% or greater. Additionally, the slow recovery stretch laminate may comprise an elastic member comprising a block copolymer comprising at least one soft block and at least two hard blocks. Further, the elastic member may be extendable to at least 50% engineering strain after exposure to mineral oil for 30 hours at room temperature and the elastic member may be extendable to at least 50% engineering strain after exposure to isopropyl palmitate for 30 hours at room temperature.

DETAILED DESCRIPTION OF THE PRESENT DISCLOSURE

Figure 1:
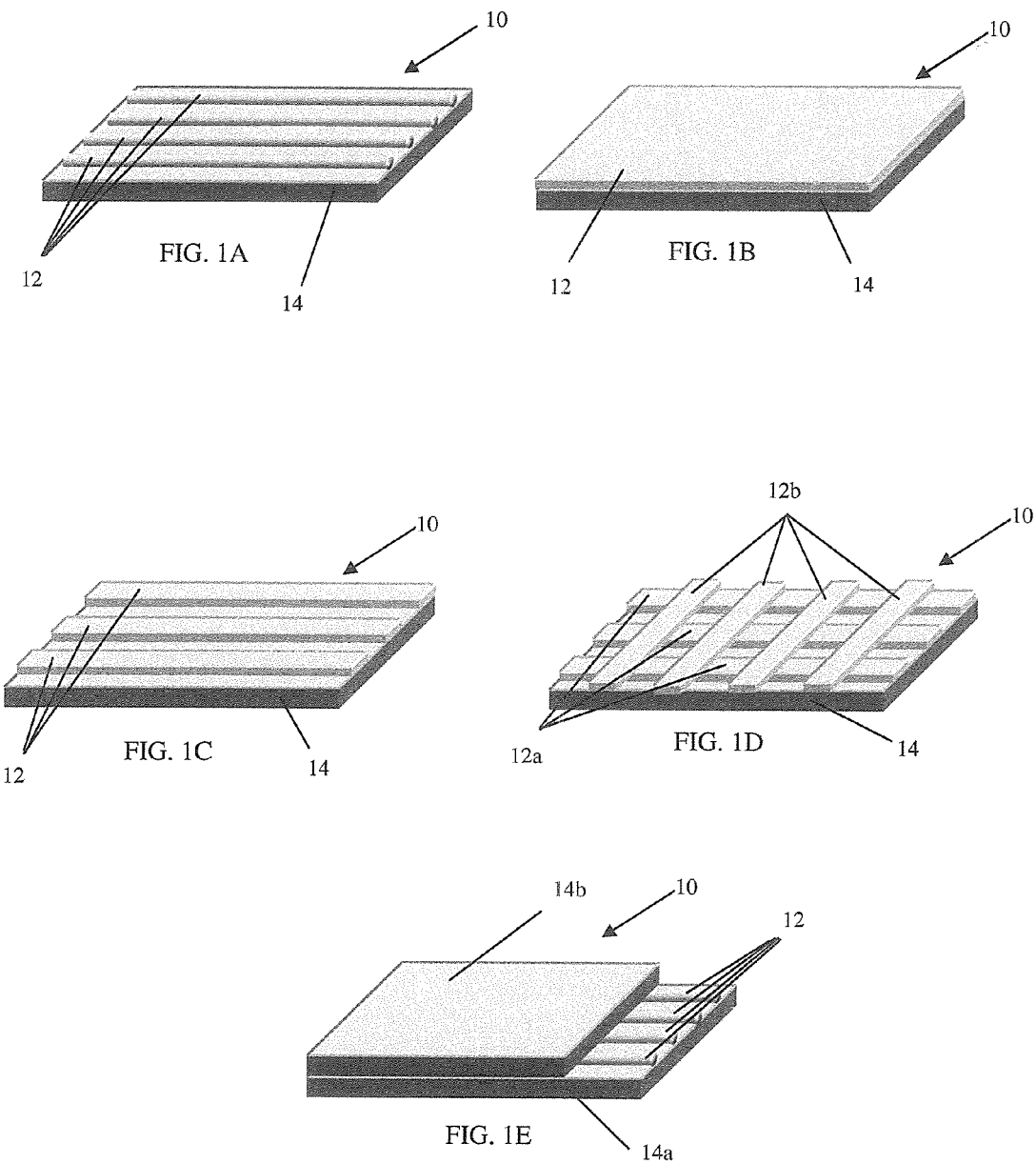
FIGS. 1A-E are perspective views of embodiments of a slow recovery stretch laminate.

As used herein, the term "absorbent article" or "article" refers to a wearable device that absorbs and/or contains liquid and, more specifically, refers to a device that is placed against or in proximity to the body of the wearer to absorb and contain the various exudates discharged from the body. Suitable examples include diapers, training pants, pull-on garments, adult incontinence products and feminine care products such as sanitary napkins. Furthermore, "absorbent article" includes "disposable absorbent article" which is intended to be discarded and not laundered or otherwise restored after no more than ten uses (although certain components may be recycled, reused, or composted).

As used herein, the term "stretch laminate" generally refers to an elastomer which is attached to at least one material such as a polymeric film, a nonwoven, a woven, or a scrim. The elastomer may be attached to the material by any of a number of bonding methods known to those skilled in the art, including adhesive bonding, thermal bonding, pressure bonding, ultrasonic bonding, and the like, or any combination thereof.

As used herein, the term "laminate" refers to a material comprising two or more layers. The term includes stretch laminates and non-stretch laminates.

As used herein, the term "diaper" refers to an absorbent article generally worn by infants and incontinent persons about the lower torso.

As used herein, the term "substrate" refers to a material that is laminated to the elastic member to form the stretch laminate. Suitable substrates include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof.

As used herein, the term "longitudinal" generally means a direction running parallel to the longitudinal axis, of the article and includes directions within 45° of the longitudinal direction.

As used herein, the term "length" of the article or component thereof generally refers to the size/distance of the maximum linear dimension, or the size/distance of the longitudinal axis, or an article or part thereof.

As used herein, the terms "lateral" or "transverse" refer to a direction generally orthogonal to the longitudinal direction and parallel to the transverse axis.

As used herein, the term "width" of the article or of a component thereof refers to the size/distance of the dimension orthogonal to the longitudinal direction of the article or component thereof, e.g., orthogonal to the length of the article or component thereof, and may refer to the distance/size of the dimension parallel to the transverse axis of the article or component.

As used herein, the term "attached" encompasses configurations whereby an element is directly secured to another element by affixing the element directly to the other element.

As used herein, the term "joined" or "connected" encompasses configurations whereby a first element is directly secured to second element by affixing the first element directly to the second element and configurations whereby a first element is indirectly secured to a second element by affixing the first element to intermediate member(s), which in turn are affixed to the second element. "Joined" or "connected" elements may be affixed either continuously or intermittently.

As used herein, "relaxed" or "relaxed state" means the state where no forces are applied to an article (other than naturally occurring forces such as gravity).

As used herein, the terms "extendibility" and "extensible", e.g., extendibility of the elastomer, mean that the width or length of the item in the relaxed position can be extended or increased.

As used herein, "elasticated" or "elasticized" means that the component comprises at least a portion made of elastic material.

As used herein, the terms "elastic," "elastomer," and "elastomeric" refer to a material which generally is able to extend to a strain of at least 50% without breaking or rupturing, and is able to recover substantially to its original dimensions after the deforming force has been removed.

As used herein, the term "medical product" means surgical gowns and drapes, face masks, head coverings, shoe coverings, wound dressings, bandages and sterilization wraps as disclosed in U.S. Pat. No. 5,540,976.

As used herein, the term "copolymer" refers to a polymer synthesized from two or more monomers with different chemical structures.

As used herein, the terms "temperature responsive" and "temperature responsiveness" refer to a slow recovery stretch laminate exhibiting less post elongation strain after a specified amount of time at higher temperatures than at lower temperatures.

As used herein, the term "conventional stretch laminate" refers to a stretch laminate that exhibits a minimal percent of initial strain after 15 seconds of recovery at 22° C. as measured by the Post Elongation Recovery Test. Conventional stretch laminates exhibit a percent of initial strain after 15 seconds of recovery at 22° C. of less than 10%, as measured by the Post Elongation Recovery Test.

As used herein, the term "percent of initial strain remaining" refers to the percentage of initial strain remaining after some period of time after release from that initial strain as measured by the Post Elongation Recovery Test. "Percent of initial strain remaining" is calculated by dividing the percent strain at a given time after release from an initial strain by the initial percent strain; the quotient is multiplied by 100 to yield a percentage.

As used herein, the terms "stress," "engineering stress," and "nominal stress" refer to the load divided by the initial undeformed cross-sectional area of the sample on which a deformation force acts.

As used herein, the terms "strain" and "engineering strain" refer to the change in sample length divided by the initial undeformed length of the sample on which a deformation force acts, usually expressed as a percent.

As used herein, the term "yield point" refers to the point on an engineering stress versus strain curve beyond which deformation is not completely recoverable, the term "yield stress" refers to the engineering stress value at the yield point, and the term "yield strain" refers to the level of strain at the yield point usually expressed as a percent strain. Some materials may also exhibit a "yield drop," i.e., a decrease in engineering stress with increasing strain.

As used herein, the terms "strain at break," "strain at failure," and "ultimate strain" refer to the maximum tensile strain to which a material can be subjected before it breaks, and may be expressed as the percentage strain.

As used herein, the term "hard block" refers to the block or blocks in a block copolymer that have a glass transition temperature (or melt temperature if the block is crystallizable) above use temperature.

As used herein, the term "hard phase" refers to the phase or phases in a block copolymer composition that are uniform in chemical composition and physical state and that have a glass transition temperature (or melt temperature if the block is crystallizable) above use temperature. The hard phase may comprise multiple hard blocks of a block copolymer and any hard block associating ingredients including, but not limited to, processing oils and modifying resins.

As used herein, the term "soft block" refers to the block or blocks in a block copolymer that have a glass transition temperature (or melt temperature if the block is crystallizable) below use temperature.

As used herein, the term "soft phase" refers to the phase or phases in a block copolymer composition that are uniform in chemical composition and physical state and that have a glass transition temperature (or melt temperature if the block is crystallizable) below use temperature. The soft phase may comprise multiple soft blocks of a block copolymer and any soft block associating ingredients including, but not limited to, processing oils and modifying resins.

As used herein, the term "block copolymer composition" refers to a polymer blend comprising a block copolymer.

As used herein, the term "force retention factor" is a measure of the unload force retained by an elastomer or laminate aged according to the Elastomer and Laminate Aging Method. The unload forces for elastomers are measured according to the Two Cycle Hysteresis Test for Elastomer Samples, and the unload forces for laminates are measured according to the Two Cycle Hysteresis Test For Laminate Samples. The force retention factor is computed according to one of the following formulas at each hold strain:

a) $\text{Force Retention Factor} = \frac{\text{(Non-Aged Unload Force)}}{[\text{(Non-Aged Unload Force)} - \text{(Aged Unload Force)}]}$, for an aged unload force less than or equal to the non-aged unload force; or b) Force Retention Factor=10, for an aged unload force greater than the non-aged unload force.

A larger force retention factor at a given hold strain corresponds to materials that show a lower relative decrease in the unload force after aging. In certain embodiments of the present disclosure, the magnitude of the force retention factor may be greater than about 2 for at least two of the maximum four hold strains, or may be greater than about 2.5 for at least two of the maximum four hold strains, or may be greater than about 3 for at least two of the maximum four hold strains, or may be greater than about 5 for at least two of the maximum four hold strains, or may be greater than about 10 for at least two of the maximum four hold strains.

As used herein, the term "morphology" refers to the shape, appearance, or form of phase domains in substances, such as polymers, polymer blends, composites, and crystals. The morphology describes the structures and shapes observed, including by microscopy or scattering techniques, of the different phase domains present within the substance. For example, for block copolymers and block copolymer compositions, common morphologies include spherical and cylindrical such as described in *Thermoplastic Elastomers*, $2^{nd}$ Edition, Chapters 3, 4, 11, and 12, G. Holden, et al. (Editors), Hanser Publishers, New York (1996).

As used herein, the term "phase domain" or "phase" refers to the region of a material that is uniform in chemical composition and physical state. In a multiphase material, each phase may form domains differing in size, chemical composition, or physical state from the other phases. For example, block copolymer compositions may comprise soft phase and hard phase regions that are uniform in chemical composition and physical state within each phase region, but the hard and soft phases generally differ from each other in size, chemical composition, and physical state. Further, for example, semi-crystalline homopolymers like polypropylene may comprise crystalline and amorphous phases differing only in size and physical state.

As used herein, the term "hysteresis" refers to the dissipation of energy in a cyclic process. For example, in a tensile hysteresis experiment where the stress is plotted against strain as the strain is increased to a target strain less than the strain at break in a load cycle, followed by decreasing the strain in an unload cycle, the two curves do not coincide but form a hysteresis loop with the unload cycle having a lower stress at a given strain compared to the load cycle.

As used herein, the term "order-disorder temperature" (ODT) refers to the temperature at which the morphology transitions from an ordered state at temperatures below the ODT to a disordered state at temperatures above the ODT. The order-disorder transition of a block copolymer, block copolymer composition, semi-crystalline polymer, or semi-crystalline polymer composition may occur over a range of temperatures. For the present disclosure, the order-disorder temperature of block copolymers and block copolymer compositions is determined according to the Order-Disorder Temperature Method.

As used herein, the term "tensile modulus of elasticity" or "Young's modulus" is a measure of the stiffness of a material. For thin materials (less than about 1.0 millimeter in thickness), the tensile modulus of elasticity can be determined according to ASTM D 882; while for thick materials (greater that about 1.0 millimeter and less than about 14 millimeters in thickness), the tensile modulus of elasticity can be determined according to ASTM D 638.

As used herein, the term "EHB polymer" or "Equivalent Hard Block polymer" refers to a polymer having essentially the same repeat unit composition and composition distribution as a hard block of a block copolymer composition. For example, for a block copolymer composition comprising a styrene-ethylene/propylene-styrene (SEPS) block copolymer, an equivalent hard block polymer is polystyrene. Additionally, a block copolymer composition may be characterized by more than one equivalent hard block polymer. For example, for a block copolymer composition comprising a SEPS block copolymer and an alphamethylstyrene-ethylene/propylene-alphamethylstyrene block copolymer, the EHB polymers for this composition would be polystyrene and poly (alphamethylstyrene). In certain embodiments of the present disclosure, the ratio of the number average molecular weight of each EHB polymer to the number average molecular weight of its corresponding hard block in the block copolymer composition may range from about 0.5 to about 100, or may range from about 1 to about 50, or may range from about 1 to about 20.

As used herein, the term "ESB polymer" or "Equivalent Soft Block polymer" refers to a polymer having essentially the same repeat unit composition and composition distribution as a soft block of a block copolymer composition. For example, for a block copolymer composition comprising a styrene-ethylene/propylene-styrene (SEPS) block copolymer, an equivalent soft block polymer is poly(ethylene/propylene). Additionally, a block copolymer composition may be characterized by more than one equivalent soft block polymer. For example, for a block copolymer composition comprising a SEPS block copolymer and a styrene-ethylene/butylene-styrene (SEBS) block copolymer, the ESB polymers for this composition would be poly(ethylene/propylene) and poly(ethylene/butylene). In certain embodiments of the present disclosure, the number average molecular weight of each ESB polymer may range from about 0.3 to about 150 kilo Daltons.

As used herein, the term "hard block associating" or "hard phase associating" refers to ingredients of a block copolymer composition that phase mix with the hard block of the block copolymer. Generally, hard block or hard phase associating ingredients have a solubility parameter similar to the solubility parameter of the hard block. In certain embodiments of the present disclosure, the solubility parameter of the hard block or hard phase associating ingredients may be within about 0.5 $(cal/cm^3)^{1/2}$ of the solubility parameter of the hard block. Further, in certain embodiments of the present disclosure, the hard block or hard phase associating ingredients may raise or lower the glass transition temperature of the hard phase from its value in the pure block copolymer. Examples of hard block associating ingredients include, but are not limited to, modifying resins, processing oils, and hard phase modifiers.

As used herein, the term "skin layer" refers to an outer layer of a coextruded, multilayer film that acts as an outer surface of the film during its production and subsequent processing.

Embodiments of absorbent articles of the present disclosure may comprise a slow recovery stretch laminate (SRSL). The SRSL may be used within the absorbent article wherever elastic properties are desired. The SRSL may comprise an elastic member joined to a substrate. The SRSL may be formed discretely and joined with the absorbent article. Conversely, the SRSL may be integral to the absorbent article (e.g., an elastic member is joined to an existing substrate in the absorbent article such as the topsheet to form a stretch laminate). The elastic member may be prepared from a composition comprising an elastomeric polymer, optionally at least one modifying resin, and optionally one or more additives. The SRSL may exhibit a normalized unload force at 37° C. of at least about 0.16 N/(g/m) as measured by the Two Cycle Hysteresis Test described below. The SRSL may exhibit a percent of initial strain after 15 seconds of recovery at 22° C. of about 10% or greater, as measured by the Post Elongation Recovery Test as described below.

In another embodiment of the present disclosure, the SRSL may be incorporated into a medical product such as a surgical gown, a face mask, a head covering, a shoe covering, a wound dressing, a bandage, or a sterilization wrap. The SRSL may be used in the medical products at locations where an elastic character is desired.

As shown in FIGS. 1A-E, the SRSL 10 may comprise an elastic member 12 joined to a substrate 14. Joining of the elastic member 12 and the substrate 14 may be conducted by a variety of bonding methods such as heat bonds, pressure bonds, ultrasonic bonds, mechanical bonds, adhesive bonds, or any other suitable attachment means or combinations of these attachment means. In certain embodiments, the elastic member 12 may exhibit sufficient tack to join the elastic member 12 and the substrate 14.

The elastic members 12 having a variety of forms may be used in the SRSL 10. Suitable focus for the elastic members 12 include, but are not limited to, films, bands, strands, individualized fibers, scrims, cross-hatch arrays, foams, or combinations thereof.

FIGS. 1A-E depict several suitable embodiments of the SRSL 10. FIG. 1A depicts an SRSL 10 having one or more elastic members 12 in the form of bands or ribbons joined with a substrate 14. FIG. 1B depicts an SRSL 10 having a sheet-like elastic member 12 joined with a sheet-like substrate 14. The elastic member 12 and the substrate 14 are shown as being coterminous; however, either layer may have dimensions differing from the other layer. FIG. 1C depicts an SRSL 10 having one or more elastic members 12 in the form of strands joined with a substrate 14.

FIG. 1D depicts an SRSL 10 having one or more elastic members in the form of a cross-hatch array joined with a substrate 14. A cross-hatch array may be formed in one instance by joining a plurality of elastic members 12a in parallel to the substrate 14. A second plurality of elastic members 12b may be joined in parallel to the substrate. The second plurality 12b may be joined in a non-parallel configuration to the first plurality 12a. A cross-hatch array may also be formed by hot needle punching of an elastomeric film. A cross-hatch array may also be formed from a porous, macroscopically-expanded, three-dimensional elastomeric web as described in U.S. Patent Application Publication No. 2004/0013852. The publication describes how the cross-hatch array can be achieved by forming the film on a porous forming structure and applying a fluid pressure differential across the thickness of the film. The fluid pressure differential causes the film to conform to the supporting structure and rupture thereby creating a cross-hatch array. FIG. 1E depicts an SRSL 10 having one or more elastic members 12 joined to two or more substrates: first substrate 14a and second substrate 14b. The particular order of the SRSL 10 layers can vary; however, in the embodiment depicted, the elastic members 12 are disposed between the first substrate 14a and the second substrate 14b, and may be bonded to one or both. The first and second substrate 14a, 14b may comprise the same material or may be distinct.

Other suitable embodiments of the SRSL 10 include using the stretch zones as disclosed in co-pending U.S. application Ser. No. 11/145,353 filed on Jun. 3, 2005 in the name of McKiernan et al., which claims the benefit of U.S. Provisional Application No. 60/643,920, filed Jan. 10, 2005.

The techniques for the formation of stretch laminates as disclosed in U.S. Pat. No. 7,717,893 and U.S. Pub. Nos. 2005-0273071, 2006-0155255, 2006-0167434, and 2009-0134049 may be applicable in the formation of the SRSL 10 of the present disclosure. One technique for creating a stretch laminate, which is commonly known as "stretch bonding," involves an elastic member such as elastic strands, bands, ribbons, films, or the like being joined to a substrate while the elastic member is in a stretched configuration. The elastic member may be stretched to at least 25% of its relaxed length. After joining, the elastic member is allowed to relax thereby gathering the substrate and creating a stretch laminate.

Another technique for creating a stretch laminate, which is commonly known as "neck bonding," involves an elastic member being bonded to a substrate while the substrate is extended and necked. In certain embodiments, the substrate may be a non-elastic substrate. Examples of neck-bonded laminates are described in U.S. Pat. Nos. 5,226,992; 4,981,747; 4,965,122; and 5,336,545. A variant of "neck bonding" is "neck stretch bonding." Neck stretch bonding refers to an elastic member being bonded to a substrate while the substrate is extended and necked and the elastic member is extended. Examples of necked stretch bonded laminates are described in U.S. Pat. Nos. 5,114,781 and 5,116,662.

In another technique for forming a stretch laminate, elastic members can be attached to a substrate in either a relaxed configuration or partially stretched configuration. The resulting laminate can be made stretchable (or more stretchable in the case of partially stretched strands or film) by subjecting the laminate to an elongation process which elongates the substrate permanently, but elongates the elastic members only temporarily. Such processes are known in the art as "zero strain" stretch laminate formation, and the elongation of such laminates may be accomplished with suitable means such as rollers, engaging teeth, or the like. Examples of zero strain activation processing and formations of resulting stretch laminates are described in U.S. Pat. Nos. 5,167,897 and 5,156,793.

Another technique for the formation of a stretch laminate is disclosed in U.S. Patent Application Publication Nos. 2003/0088228A1, 2003/0091807A1, and 2004/0222553A1. The technique disclosed in these publications involves forming the elastic member by hot melt application of one or more thermoplastic elastomers onto a substrate, followed by incremental stretching of the substrate that confers the stretch properties of the elastomer to the substrate. Suitable application methods include, for example, direct gravure, offset gravure, and flexographic printing. Each of these methods allows deposition of an amount of elastomer in any shape and direction, thus providing substantial flexibility in the stretch character exhibited by the stretch laminate. Other conventional methods for stretch laminate formation are within the scope of this description.

Additionally, to produce reliable SRSLs, it is important to achieve a relatively uniform strain profile throughout the stretch zone. Materials exhibiting a yield drop may have stability problems during stretching, such as variations in thickness, and thereby generally result in laminates with a high level of property variation. Increasing the stretching temperature, decreasing the strain rate, and/or prestretching the elastic member can make the yield drop less pronounced, thereby improving the chances for achieving a more uniform strain profile. Such results in the fabrication of more reliable stretch laminates. Production of SRSLs may be found in U.S. Pub. No. 2005-0273071.

The elastic member 12 may comprise an elastomeric polymer, optionally at least one modifying resin, and optionally one or more additives. A number of elastomeric polymers, either alone or in combination, can be used to prepare the elastic member 12. Elastomeric polymers include, but are not limited to, homopolymers (e.g., cross-linked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like. Other suitable block copolymers include, but are not limited to, polyolefin based block copolymers such as described in *Thermoplastic Elastomers, $2^{nd}$ Edition*, Chapter 5, G. Holden, et al. (Editors), Hanser Publishers, New York (1996)

In one embodiment, the elastomeric polymer may be a block copolymer. A number of block copolymers may be used including multi-block, tapered block and star block copolymers. Block copolymers suitable for use in embodiments of the present disclosure may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. The hard block may have a Tg greater than about 35° C. or is crystalline or semicrystalline with a Tm above about 35° C. The hard block portion may be derived from vinyl monomers including vinyl arenes such as styrene and alpha-methylstyrene, methacrylates, acrylates, acrylamides, methacrylamides, polyolefins including polypropylene and polyethylene, or combinations thereof. For hard blocks comprising substantially polystyrene, the hard block molecular weight may range from about 4 to about 20 kilo Daltons, or may range from about 6 to about 16 kilo Daltons, or may range from about 7 to about 14 kilo Daltons, or may range from about 8 to about 12 kilo Daltons. The weight percent of the hard block in the pure block copolymer may range from about 10 to about 40 weight percent, or may range from about 20 to about 40 weight percent, or may range from about 25 to about 35 weight percent. Further, the slow recovery stretch laminate embodiments of the present disclosure may comprise a block copolymer that comprises at least two hard blocks. It is possible that block copolymers comprising only one hard block may result in block copolymer compositions that behave more like a viscous liquid than an elastomer. Further, it is possible that block copolymers comprising at least two hard blocks may result in block copolymer compositions that behave like an elastomer.

Glass transition temperatures referred to herein are determined by tensile dynamic mechanical analysis performed in the linear elastic region of the material at a frequency of 1 Hz using a temperature ramp method such as described in ASTM D 5026, unless specified otherwise. Suitably, film samples with a uniform thickness of about 0.3 mm may be used with a temperature ramp rate of about 1° C./min or slower. The loss modulus peak temperature is taken as the Tg of a particular material or phase.

Crystalline melting temperatures referred to herein are determined by Differential Scanning calorimetry using a temperature ramp rate of 10° C./min. The melting endothermic peak temperature on the second heat is taken as the Tm of the particular crystalline region, such as described in ASTM D 3418.

The block copolymers may comprise a soft block (or segment). The soft block may exhibit a sufficiently low glass transition temperature and/or melting temperature so as not to form glassy or crystalline regions at the use temperature of the copolymer. In one embodiment, the use temperature may be between about room temperature (about 22° C.) and about body temperature (about 37° C.). However, other use temperatures are feasible and within the scope of this invention. Such soft blocks are generally physically incompatible with the hard blocks and form separate regions, domains, or phases. The slow recovery stretch laminate embodiments of the present disclosure may comprise a block copolymer that comprises at least one soft block. It is possible that block copolymers comprising at least one soft block may result in block copolymer compositions that behave like an elastomer.

The soft block portion may be a polymer derived from conjugated aliphatic diene monomers. The monomers used to synthesize the soft block may contain fewer than about 6 carbon atoms. Suitable diene monomers include butadiene, isoprene, and the like. Further, it is envisioned that the soft block may be modified to tailor the Tg of the soft block. For example, a random copolymer of styrene and dienes, where the Tg of the soft block may be controlled by the ratio of styrene to diene may be used. Additionally, for example, high 1,2 diene polymers known to have high glass transition temperatures may be used or a graft of styrene onto poly(isoprene) may be used. In such cases, lower amounts of the modifying resin may be used. Additionally, such tailored soft blocks may be hydrogenated. Further, in certain embodiments of the present disclosure, the soft block portion may be a polymer derived from acrylates, silicones, polyesters and polyethers including, but not limited to, poly(ethylene adipate) glycol, poly(butylene-1,4 adipate) glycol, poly(ethylene butylene-1,4 adipate) glycol, poly(hexamethylene 2,2-dimethylpropylene adipate) glycol, polycaprolactone glycol, poly(diethylene glycol adipate) glycol, poly(1,6-hexanediol carbonate) glycol, poly(oxypropylene)glycol, and poly(oxytetramethylene)glycol.

Suitable block copolymers for use in embodiments of the present disclosure may comprise at least two hard blocks (A) and at least one soft block (B). The block copolymers may have multiple blocks. In one embodiment, the block copolymer may be an A-B-A triblock copolymer, an A-B-A-B tetrablock copolymer, or an A-B-A-B-A pentablock copolymer. Also, useful herein are triblock copolymers having hard blocks A and A', wherein A and A' may be derived from different vinyl compounds. Also, useful in embodiments of the present disclosure are block copolymers having more than one hard block and/or more than one soft block, wherein each hard block may be derived from the same or different monomers and each soft block may be derived from the same or different monomers. It should be noted that where the copolymer contains residual olefinic double bonds, the copolymer may be partially or fully hydrogenated if desired. Saturation may yield beneficial effects in the elastomeric properties of the copolymer.

Suitable star block copolymers may be comprised of multiple arms connected at the center and whose arms are constituted of at least one soft and at least one hard block where the hard block is chosen from either a) blocks of monoalkenyl aromatic hydrocarbons or b) blocks of random copolymers of monoalkenyl aromatic hydrocarbons and conjugated diolefin monomers with glass transition temperatures above 20° C., and the soft block is chosen from either c) blocks of random copolymers of monoalkenyl aromatic hydrocarbons and conjugated diolefin monomers with glass transition temperatures below 10° C., or d) blocks of conjugated diolefins. These star block polymers can be based on a-c blocks, b-c blocks, a-d blocks or b-d blocks. In certain embodiments of the present disclosure, the number of arms may be 100 or less, or the number of aims may be 50 or less, or the number of arms may be 10 or less, or the number of arms may be 5 or less.

The elastic member 12 may comprise the elastomeric polymer in amounts from about 20% to about 100%, by weight. In other suitable embodiments, the elastic member 12 may comprise the elastomeric polymer in amounts from about 20% to about 80%, or may comprise the elastomeric polymer in amounts from about 30% to about 65%, or may comprise the elastomeric polymer in amounts from about 40% to about 60% Alternatively, the elastic member 12 may comprise the elastomeric polymer in amounts from about 45% to about 60%.

In certain embodiments, elastomeric polymers include styrene-olefin-styrene triblock copolymers such as styrene-ethylene/butylene-styrene (S-EB-S), styrene-ethylene/propylene-styrene (S-EP-S), styrene-ethylene-ethylene/proplyene-styrene (S-EEP-S), and mixtures thereof. The block copolymers may be employed alone or in a blend of block copolymers, and may be partially or fully hydrogenated.

In particular embodiments, the elastomeric polymers include styrene-ethylene/butylene-styrene (S-EB-S), styrene-ethylene/propylene-styrene (S-EP-S), styrene-ethylene-ethylene/proplyene-styrene (S-EEP-S), and hydrogenated styrene-isoprene/vinyl isoprene-styrene. Such linear block copolymers are commercially available under the trade designation Kraton from Kraton Polymers, Houston, Tex., and under the trade designations Septon™ and Hybrar™ from Kuraray America, Inc., Pasedena, Tex.

The elastic member 12 may comprise one or more modifying resins. Suitable modifying resins may associate or phase mix with the soft blocks of the elastomeric polymer. Modifying resins may have a sufficiently high molecular weight average such that the glass transition temperature of the soft phase is increased resulting in an increase of post elongation strain at 22° C. after 15 seconds of recovery. While not intending to be bound by this theory, it is believed that the modifying resins raise the Tg of the soft phase to the point where molecular relaxation at use temperatures is slowed. This is evidenced by a relatively high post elongation strain. In certain embodiments of the present disclosure, the glass transition temperature of the soft phase may range from about −50° C. to about 35° C. In other embodiments of the present disclosure, the glass transition temperature of the soft phase may range from about −40° C. to about 25° C., while in other embodiments the glass transition temperature of the soft phase may be range from about −30° C. to about 20° C. Further, in still other embodiments of the present disclosure, the glass transition temperature of the soft phase may range from about −20° C. to about 15° C., while in other embodiments the glass transition temperature of the soft phase may range from about −10° C. to about 10° C. The glass transition temperature of the soft phase influences the percent of initial strain after 15 seconds of recovery at 22° C., the level of temperature responsiveness, and the unload force at 37° C.

The elastic member 12 may comprise modifying resins in amounts from about 0% to about 60% by weight. In other embodiments, the elastic member 12 may comprise modifying resins in amounts from about 10% to about 55%, or may comprise modifying resins in amounts from about 20% to about 55%, or may comprise modifying resins in amounts from about 30% to about 50%. In certain embodiments, the elastic member 12 may comprise modifying resins in amounts from about 40% to about 50%.

Suitable modifying resins useful herein may have glass transition temperatures ranging from about 60° C. to about 180° C., from about 70° C. to about 150° C., and from about 90° C. to about 130° C.

Suitable modifying resins may be soft block associating. A solubility parameter is useful in determining whether the modifying resin will phase mix with the soft block of the block copolymer. Generally, modifying resins are selected so that the solubility parameter of the modifying resin is similar to the solubility parameter of the soft block phase. For example in the case where the solubility parameter of the soft block phase is about 8 $(cal/cm^3)^{1/2}$, the solubility parameter of the modifying resin may be from about 7.5 $(cal/cm^3)^{1/2}$ to about 8.5 $(cal/cm^3)^{1/2}$. The solubility parameters of the modifying resins may also approximate the solubility of the hard block. However, so long as the modifying resin phase mixes with the soft block, hard block phase mixing should not be read as limiting. A list of solubility parameters for common polymers or resins, along with methods for determining or approximating the solubility parameters can be found in the *Polymer Handbook, Third Edition;* Wiley Interscience; Section VII pages 519-559.

Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. The resin may be selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Modifying resins may also include alicyclic terpenes, hydrocarbon resins, cycloaliphatic resins, poly-beta-pinene, terpene phenolic resins, and combinations thereof. "C5 hydrocarbon resins" and "C9 hydrocarbon resins" are disclosed in U.S. Pat. No. 6,310,154.

The elastic member 12 may comprise a variety of additives. Suitable additives including, for example, stabilizers, antioxidants, and bacteriostats may be employed to prevent thermal, oxidative, and bio-chemical degradation of the elastic member 12. Additives may account for about 0.01% to about 60% of the total weight of the elastic member 12. In other embodiments, the composition comprises from about 0.01% to about 25%. In other suitable embodiments, the composition comprises from about 0.01% to about 10% by weight, of additives.

Various stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Proprietary commercial stabilizers and/or antioxidants are available under a number of trade names including a variety of Wingstay®, Tinuvin® and Irganox® products.

The elastic member 12 may comprise various bacteriostats that are known in the art. Examples of suitable bacteriostats include benzoates, phenols, aldehydes, halogen containing compounds, nitrogen compounds, and metal-containing compounds such as mercurials, zinc compounds and tin compounds. A representative example is available under the trade designation Irgasan Pa. from Ciba Specialty Chemical Corporation, Tarrytown, N.Y.

Other optional additives include thermoplastic polymers or thermoplastic polymer compositions which preferentially associate with the hard blocks or segments of the block copolymers. It is possible that these thermoplastic polymers become incorporated into the entangled three-dimensional network structure of the hard phase. This entangled network structure can provide improved tensile, elastic and stress relaxation properties of the elastomeric composition. When the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, may be useful in embodiments the present disclosure because they are generally considered to be chemically compatible with the styrenic hard blocks of the block copolymer.

The elastic member 12 may comprise viscosity modifiers, processing aids, slip agents or anti-block agents. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. Mineral oil may be used as a processing oil. Viscosity modifiers are also well known in the art. For example, petroleum derived waxes can be used to reduce the viscosity of the slow recovery elastomer in thermal processing. Suitable waxes include low number-average molecular weight (e.g., 0.6-6.0 kilo Daltons) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives within the composition that forms the elastic member 12. Colorants can include dyes and pigments such as titanium dioxide. Fillers may include such materials as talc and clay. Other additives may include dyes, UV absorbers, odor control agents, perfumes, fillers, desiccants, and the like.

In certain embodiments of the present disclosure, the elastomeric compositions may be microphase separated and it may be desired that the soft phase be substantially continuous while comprising specific anchoring points that include, but are not limited to, one or both of the following: (1) chemical cross-links, and (2) physical cross-links including, but not limited to, one or more of the following—crystalline domains, phase separated blocks, and ionic groups. It is possible that maintaining the soft phase as substantially continuous ensures a relatively high unload force at 37° C. and a relatively high post elongation strain at 22° C. after 15 seconds of recovery.

In certain embodiments of the present disclosure, it has been found that the unload force of the slow recovery stretch laminate at 37° C. can drop substantially after being held at moderate strain levels for prolonged periods of time, especially at elevated temperatures. Those trained in the art will appreciate that this behavior may lead to poor product performance in those cases where a slow recovery stretch laminate component of an absorbent article is held under strain while stored in its distribution package. Depending on the placement of the slow recovery stretch laminate(s) within an absorbent article and on the particular absorbent article, a substantial drop in the unload force at 37° C. can lead to, for example, increased urine or bowel movement leakage during use, sagging or drooping of the absorbent article during use, or increased discomfort in wearing the absorbent article.

It is possible that for slow recovery stretch laminates comprising an elastic member comprising a block copolymer composition that a drop in the unload force at 37° C. after being held at moderate strain levels for prolonged periods of time is a result of hard blocks being pulled out of the hard phase domains, retracting to some degree, and then reintegrating into different hard phases. This behavior is believed to lead to a rearrangement of the physical cross-links (hard phases), i.e., a loss of "memory" as those trained in the art may characterize this process, and thereby an increase in permanent set and it is the increase in permanent set that results in the reduction of the unload force at 37° C. Additionally, it is possible that for slow recovery stretch laminates comprising an elastic member comprising a block copolymer composition that strengthening the physical cross-links or introducing chemical cross-links may represent approaches for reducing or minimizing any drop in the unload force at 37° C. that may occur after being held at moderate strain levels for prolonged periods of time. For slow recovery stretch laminates comprising an elastic member comprising a block copolymer composition:

(1) The soft block of the block copolymer may be hydrogenated. In certain embodiments of the present disclosure, the degree of hydrogenation may be greater than about 70 mole percent of the soft block, or the degree of hydrogenation may be greater than about 80 mole percent of the soft block, or the degree of hydrogenation may be greater than about 90 mole percent of the soft block, or the degree of hydrogenation may be greater than about 95 mole percent of the soft block, or the degree of hydrogenation may be greater than about 99 mole percent of the soft block. It is possible that hydrogenation of the soft block creates a higher energy barrier for the hard block to overcome in order to be pulled out of its hard phase domain. A measure of this behavior is the order-disorder temperature (ODT) of the block copolymer which generally goes up with hydrogenation (in some embodiments more than 50° C.). The ODT of an hydrogenated block copolymer may be further increased through nitration (in some embodiments more than 50° C.). Further, for hydrogenated block copolymers comprising a hard block comprising polystyrene, nitration may be most beneficial when the hard block is preferentially nitrated. In certain embodiments of the present disclosure, the degree of nitration may be greater than about 10% and less than about 100%, or the degree of nitration may be greater than about 20% and less than about 70%, or the degree of nitration may be greater than about 30% and less than about 60%, where a degree of nitration of 50% refers to an average of 1 nitro group per two aromatic rings of the hydrogenated block copolymer, a degree of nitration of 100% refers to an average of 1 nitro group per aromatic ring, a degree of nitration of 200% refers to an average of 2 nitro groups per aromatic ring, and a degree of nitration of 300% refers to an average of 3 nitro groups per aromatic ring. Further, to minimize chain scission within the soft block during nitration, the degree of hydrogenation of the soft block backbone may be greater than about 70 mole percent of the soft block backbone, or the degree of hydrogenation may be greater than about 80 mole percent of the soft block backbone, or the degree of hydrogenation may be greater than about 90 mole percent of the soft block backbone, or the degree of hydrogenation may be greater than about 95 mole percent of the soft block backbone, or the degree of hydrogenation may be greater than about 99 mole percent of the soft block backbone. Further, for hydrogenated block copolymers comprising a hard block comprising polystyrene, it may be possible to increase the ODT through aromatic substitution with (1) chlorine, bromine, or nitrile groups, (2) ketone groups of various structures including methyl, ethyl, propyl, and butyl ketones, (3) ester groups of various structures including methyl, ethyl, propyl, butyl, pentyl and hexyl esters, (4) mono- and di-substituted amide groups of various structures including methyl, ethyl, propyl, butyl, phenyl, and benzyl amides, or (5) combinations thereof, including combinations with nitro groups, where the preference for hard block substitution as well as the degree of substitution and soft block hydrogenation may be similar to that for nitration described above.

For slow recovery stretch laminates comprising an elastic member comprising a block copolymer composition comprising an hydrogenated block copolymer, the block copolymer composition ODT may be greater than about 135° C., or the block copolymer composition ODT may be greater than about 150° C., or the block copolymer composition ODT may be greater than about 170° C. Those trained in the art will recognize that there may be a desired upper limit for the ODT of a block copolymer composition because of processing difficulties that may arise including, but not limited to, rheological considerations, e.g., viscosity is too high, or stability concerns. It is not uncommon for block copolymer compositions to begin degrading at high process temperatures. When processing a block copolymer composition comprising an hydrogenated block copolymer at or above its ODT, an upper ODT limit may be about 300° C., or an upper ODT limit may be about 275° C., or an upper ODT limit may be about 250° C. Further, when processing a block copolymer composition comprising an hydrogenated block copolymer below its ODT, an upper processing temperature limit may be about 300° C., or an upper processing temperature limit may be about 275° C., or an upper processing temperature limit may be about 250° C. Additionally, those trained in the art will recognize that slow recovery stretch laminates that use adhesive bonds to join the elastic member and substrate may result in chemical species of one migrating into the other, e.g., adhesives may contain oil and modifying resins that may migrate into the elastic member especially if the levels are higher in the adhesive composition than in the elastic member. Further, such migration of chemical species can alter the properties of the slow recovery stretch laminate from the time it is produced to the time it is used in a product by the consumer, e.g., the unload force at 37° C. and the percent of initial strain at 22° C. after 15 seconds, as well as alter properties of the elastic member, including the order-disorder temperature. Consequently, when measuring the ODT of an elastic member from a consumer product comprising a block copolymer composition, those trained in the art will be cognizant that this ODT may be different and may be lower than that of the as produced elastic member.

(2) The glass transition temperature of the hard phase may be greater than about 60° C., or may be greater than about 80° C., or may be greater than about 100° C., or may be greater than about 120° C. The glass transition temperature is a measure of the hard phase strength, where a higher Tg generally corresponds to higher strength within a given chemical family of hard blocks, e.g., polystyrene. Those trained in the art will appreciate that certain ingredients in block copolymer compositions, e.g., modifying resins and processing oils, may associate with the hard blocks and may lower the glass transition temperature of the hard phase from its value in the pure block copolymer. Consequently, the ingredients of block copolymer compositions may be chosen so as to minimize any depression in the glass transition temperature of the hard phase. In certain embodiments of the present disclosure, any combination of ingredients and added percentages may be chosen as long as the glass transition temperature of a polymer blend consisting of an equivalent hard block (EHB) polymer and the added ingredients is greater than or about equal to the glass transition temperature of the neat EHB polymer, as described in the Hard Block Glass Transition Method.

Possible means of increasing the glass transition temperature of the hard phase within a block copolymer composition include, but are not limited to, one or more of the following:

(i) Adding a high glass transition temperature hard phase modifier or a combination of high glass transition temperature hard phase modifiers to the block copolymer composition. For example, poly(2,6-dimethyl-1,4-phenylene oxide) or tetramethyl bisphenol-A polycarbonate (TMBAPC) for hard blocks comprising substantially polystyrene. The glass transition temperature of a hard phase modifier may be greater than about 80° C., or may be greater than about 100° C., or may be greater than about 120° C., or may be greater than about 140° C. Further, in certain embodiments of the present disclosure, any combination of high glass transition temperature hard phase modifiers and added percentages may be suitable for embodiments of the present disclosure as long as the glass transition temperature of a polymer blend consisting of an EHB polymer and the hard phase modifiers is greater than the Tg of the neat EHB polymer, as described in the Hard Block Glass Transition Temperature Method. In certain embodiments of the present disclosure, TMBAPC modified with benzyl end groups (mTMBAPC) may provide greater miscibility with a substantially polystyrene hard block, and mTMBAPC may provide a higher increase in the glass transition temperature of the hard phase than TMBAPC at the same added weight percent.

(ii) Using particular synthetic processing oils instead of or in combination with natural processing oils, e.g., mineral oil. In certain embodiments of the present disclosure, suitable synthetic processing oils may be those disclosed in U.S. Pat. No. 7,468,411.

(iii) Nitration of the hard block. For hydrogenated block copolymers comprising a hard block comprising polystyrene, the degree of nitration may be greater than about 10% and less than about 100%, or the degree of nitration may be greater than about 20% and less than about 70%, or the degree of nitration may be greater than about 30% and less than about 60%. Further, to minimize chain scission within the soft block during nitration, the degree of hydrogenation of the soft block backbone may be greater than about 70 mole percent of the soft block backbone, or the degree of hydrogenation may be greater than about 80 mole percent of the soft block backbone, or the degree of hydrogenation may be greater than about 90 mole percent of the soft block backbone, or the degree of hydrogenation may be greater than about 95 mole percent of the soft block backbone, or the degree of hydrogenation may be greater than about 99 mole percent of the soft block backbone. Further, for hydrogenated block copolymers comprising a hard block comprising polystyrene, it may be possible to increase the Tg through aromatic substitution with (1) chlorine, bromine, or nitrile groups, (2) ketone groups of various structures including methyl, ethyl, propyl, and butyl ketones, (3) ester groups of various structures including methyl, ethyl, propyl, butyl, pentyl and hexyl esters, (4) mono- and di-substituted amide groups of various structures including methyl, ethyl, propyl, butyl, phenyl, and benzyl amides, or (5) combinations thereof, including combinations with nitro groups, where the degree of substitution and soft block hydrogenation may be similar to that for nitration described above.

The glass transition temperature of the hard phase may depend on the chemistry and molecular weight of the hard blocks comprising the block copolymer composition and on the type and amount of hard phase associating ingredients of the block copolymer composition including, but not limited to, modifying resins, processing oils, and hard phase modifiers. In certain embodiments of the present disclosure, the block copolymer composition may be characterized by one EHB polymer, and in this case any combination of hard phase associating ingredients and added percentages may be blended into the block copolymer composition as long as the glass transition temperature of a polymer blend consisting of the EHB polymer and the hard phase associating ingredients is greater than or about equal to the glass transition temperature of the neat EHB polymer, as described in the Hard Block Glass Transition Method. Further, in certain embodiments of the present disclosure, the block copolymer composition may be characterized by more than one EHB polymer. In those instances, there is a glass transition temperature for each EHB polymer and a glass transition temperature for each polymer blend consisting of one of the EHB polymers and the hard phase associating ingredients of the block copolymer composition. Additionally, in this case, at least one of the blend glass transition temperatures may be greater than or about equal to the glass transition temperature of the corresponding neat EHB polymer (3) The block copolymer composition may comprise equivalent hard block (EHB) polymers. For example, the addition of homopolymer polystyrene for block copolymers comprising substantially polystyrene hard blocks. It is possible that the addition of EHB polymers may provide a reinforcing benefit to the block copolymer composition. Further, it is possible that the degree of interaction between the hard block of the block copolymer and the EHB polymer is dependent on the molecular weight of each species. The ratio of the number average molecular weight of the EHB polymer to the number average molecular weight of the hard block of the block copolymer may range from about 0.5 to about 100, or may range from about 1 to about 100, or may range from about 1 to about 50, or may range from about 1 to about 20. Further, it is possible that the reinforcing benefit may result in increased strength and decreased force relaxation. In certain embodiments of the present disclosure, block copolymer compositions comprising EHB polymers may result in a tensile strength increase of greater than about 5% over the block copolymer composition without the EHB polymer, or greater than about 10%, or greater than about 20%, or greater than about 30%. For thin materials (less than about 1.0 millimeter in thickness), the tensile strength can be determined according to ASTM D 882; while for thick materials (greater that about 1.0 millimeter and less than about 14 millimeters in thickness), the tensile strength can be determined according to ASTM D 638. Further, block copolymer compositions comprising EHB polymers may result in a force relaxation decrease over the block copolymer composition without the EHB polymer. In certain embodiments of the present disclosure, the percentage force loss in tensile mode after 1 hour of relaxation at 37° C. and 50% engineering strain of a block copolymer composition comprising a EHB polymer may be less than about 0.99× the block copolymer composition without an EHB polymer, or may be less than about 0.95×, or may be less than about 0.9×, or may be less than about 0.8×, where the percentage force loss can be determined according to ASTM D 6048.

For certain embodiments of the present disclosure comprising block copolymer compositions, it may be desirable to have the hard phase form a spherical morphology which may minimize hysteresis. Many commercially available block copolymers suitable for the present disclosure may contain from about 20% by weight to about 40% by weight hard block and may possess cylindrical or lamellar morphologies. To achieve a spherical morphology, it may be advantageous to blend in soft phase associating ingredients that adjust the composition leading to a spherical morphology, e.g., by decreasing the weight percentage of the hard phase in the block copolymer composition. In addition to modifying resins that may raise the soft phase Tg and processing oils that may lower the soft phase Tg, another type of soft phase modifier is an equivalent soft block (ESB) polymer. For example, the addition of poly(ethylene/propylene) for block copolymers comprising an ethylene/propylene soft block such as SEPS, or the addition of a poly(styrene-isoprene) random copolymer of similar repeat unit composition to a polystyrene block copolymer composition comprising a random styrene-isoprene soft block. It is possible that the addition of ESB polymers may provide a hard phase dilution benefit to the block copolymer composition, e.g., leading to a hard phase spherical morphology, and may provide a benefit in maintaining or increasing the order-disorder temperature as compared to other soft block associating ingredients such as modifying resins and processing oils that may reduce the order-disorder temperature. Further, it is possible that the molecular weight of the equivalent soft block polymer may influence the rheology of the ESB polymer and may affect the rheology of the block copolymer composition. In certain embodiments of the present disclosure, the number average molecular weight of an ESB polymer may range from about 0.3 to about 150 kilo Daltons. Further, in certain embodiments of the present disclosure, any combination of soft phase associating ingredients and percentages may be chosen as long as (1) the slow recovery stretch laminate exhibits a percent of initial strain after 15 seconds of recovery at 22° C. of about 10% or greater and an unload force at 37° C. of about 0.16 N/(g/m) or greater, and comprises a hard phase exhibiting spherical morphology, or (2) the slow recovery elastomer exhibits a percent of initial strain after 15 seconds of recovery at 22° C. of about 10% or greater and a normalized unload force at 37° C. and 60% hold strain of greater than about 0.07 N, and comprises a hard phase exhibiting spherical morphology.

In certain embodiments of the present disclosure, it has been found that during the use of an absorbent article comprising a slow recovery stretch laminate comprising an elastic member, certain baby oils, lotions, gels, cremes, and the like, that are spread on the wearer's skin before application of the article, may be absorbed to some extent by the elastic member. It is possible that this behavior may lead to a swelling or breakage of the elastic member and may result in reduced performance. Swelling may lead to (1) a sticky feeling slow recovery stretch laminate that may cause discomfort to the wearer of the absorbent article, and/or (2) a reduction in the unload force of the slow recovery stretch laminate at 37° C., which may result in poor fit and may lead to, for example, increased urine or bowel movement leakage during use, sagging or drooping of the absorbent article during use, and/or increased discomfort in wearing the absorbent article. Breakage of the elastic member may lead to poor fit if it is localized, but if widespread may lead to catastrophic failure of the slow recovery stretch laminate which may lead to the failure of the absorbent article comprising the slow recovery stretch laminate.

It is possible that for slow recovery stretch laminates comprising an elastic member comprising a block copolymer composition that certain ingredients of baby oils, lotions, gels, cremes, and the like, may weaken or solubilize the hard block or hard phase domains of the elastic member. In certain embodiments of the present disclosure, this behavior is believed to lead to a dissolution of physical cross-links (hard phases) and thereby a weakening or breakage of the elastic member. The solubility parameter of the hard block is useful for determining whether the hard block may be susceptible to solubilization by ingredients of baby oils, lotions, gels, cremes, and the like. In certain embodiments of the present disclosure, the solubility parameter of the hard block may be greater than about 9.1 $(cal/cm^3)^{1/2}$, or may be greater than about 9.3 $(cal/cm^3)^{1/2}$, or may be greater than about 9.5 $(cal/cm^3)^{1/2}$, where the solubility parameter of the hard block is determined according to the method described by L. H. Sperling in *Introduction to Physical Polymer Science*, Wiley-Interscience (New York, 1992). For example, according to the method described by Sperling, the solubility parameter for polystyrene hard blocks is determined to be 8.96 $(cal/cm^3)^{1/2}$. Further, in certain embodiments of the present disclosure, it has been found that exposure of an elastic member comprising substantially polystyrene hard blocks to baby oils containing ingredients like, but not limited to, isopropyl palmitate may lead to disintegration of the elastic member wherein the elastic member becomes fragile and may deteriorate into stringy-like pieces. According to the method described by Sperling, the solubility parameter of isopropyl palmitate is determined to be 8.12 $(cal/cm^3)^{1/2}$, indicating that negative effects may occur to an elastic member exposed to ingredients like isopropyl palmitate when the solubility parameter differences between the hard block and such ingredients is about 0.84 $(cal/cm^3)^{1/2}$ or less. Further, in certain embodiments of the present disclosure, it has been found that elastic members which survive exposure to mineral oil and ispropyl palmitate, as described in the Oil Exposure Method, may be considered resistant to baby oils, lotions, gels, cremes, and the like, when spread on the wearer's skin before application of an absorbent article comprising a slow recovery stretch laminate comprising the elastic member. Still further, in contrast to the high glass transition temperature hard block modifiers described above, ingredients of baby oils, lotions, gels, cremes, and the like, that may cause a negative impact on elastic members may have a glass transition temperature well below room temperature, e.g., may be liquid at room and use temperatures, and it is possible that exposure of the elastic member to such ingredients may result in a hard phase glass transition temperature below use temperature and may result in a weakening and possible dissolution of the elastic member. Additionally, it is possible that ingredients of baby oils, lotions, gels, cremes, and the like, which are liquid at use temperature may require a larger difference between the solubility parameter of such ingredients and the solubility parameter of the hard block in order for the hard block to remain intact after exposure to such ingredients as compared to the difference between the solubility parameter of modifying resins, which are typically solid at use temperature, and the solubility parameter of the soft block in order for the modifying resin to be soft block associating, as described above.

For slow recovery stretch laminates comprising an elastic member comprising a block copolymer composition comprising a hard block comprising polystyrene, possible means of increasing the resistance of the elastic member to certain ingredients of baby oils, lotions, gels, cremes, and the like include, but are not limited to, aromatic substitution with nitro, chlorine, bromine, or nitrile groups, ketone groups of various structures including methyl, ethyl, propyl, and butyl ketones, ester groups of various structures including methyl, ethyl, propyl, butyl, pentyl and hexyl esters, mono- and di-substituted amide groups of various structures including methyl, ethyl, propyl, butyl, phenyl, and benzyl amides, and combinations thereof. For block copolymers comprising a hard block comprising polystyrene, the degree of substitution may be greater than about 10% and less than about 300%, or the degree of substitution may be greater than about 10% and less than about 200%, or the degree of substitution may be greater than about 10% and less than about 100%, or the degree of substitution may be greater than about 20% and less than about 70%, or the degree of substitution may be greater than about 30% and less than about 60%, where a degree of substitution of 50% refers to an average of 1 substituted group per two aromatic rings of the block copolymer, a degree of substitution of 100% refers to an average of 1 substituted group per aromatic ring, a degree of substitution of 200% refers to an average of 2 substituted groups per aromatic ring, and a degree of substitution of 300% refers to an average of 3 substituted groups per aromatic ring. Further, to minimize chain scission within the soft block during aromatic substitution, the degree of hydrogenation of the soft block backbone may be greater than about 70 mole percent of the soft block backbone, or the degree of hydrogenation may be greater than about 80 mole percent of the soft block backbone, or the degree of hydrogenation may be greater than about 90 mole percent of the soft block backbone, or the degree of hydrogenation may be greater than about 95 mole percent of the soft block backbone, or the degree of hydrogenation may be greater than about 99 mole percent of the soft block backbone.

Further, it is possible to increase the resistance of the elastic member to certain ingredients of baby oils, lotions, gels, cremes, and the like, through the use of polymer skin layers on the elastic member, e.g., an A-B-A (3-layer) film construction where the A layers represent the polymer skins and the B layer an elastomer, e.g., a slow recovery elastomer. For certain embodiments of the present disclosure, the polymer skin layers may comprise thermoplastic elastomers based on, but not limited to, polyurethanes, polyesters, polyether amides, elastomeric polyolefins including polyethylenes and polypropylenes, elastomeric polyolefin blends, and combinations thereof. In other embodiments of the present disclosure, the polymer skin layers may comprise thermoplastic polymers based on, but not limited to, polyolefin polymers including polyethylenes and polypropylenes, and combinations thereof. Further, for certain embodiments of the present disclosure, the polymer skin layers may comprise combinations of thermoplastic elastomers and thermoplastic polymers. Additionally, other multilayer film constructions are also within the scope of the present disclosure including, but not limited to, A-B-C, A-B-A-B-A, and A-B-C-B-A type constructions. Further, the use of polymer skins may also provide an antiblock benefit, reducing the tendency of the elastic member to stick to itself, to substrates, or to processing equipment.

Further, it is possible to increase the resistance of the elastic member to certain ingredients of baby oils, lotions, gels, cremes, and the like, through the use of particulate materials incorporated onto the outer surfaces of the elastic member. For certain embodiments of the present disclosure, suitable particulate materials include, but are not limited to, inorganic minerals such as talc, calcium carbonate, clays, titanium dioxide, tricalcium phosphate, and silica, e.g., Aerosil® 90 available from Evonik Degussa Corporation, Piscataway, N.J., organic particulates such as starch and cellulose, and combinations thereof. Further, the use of particulate materials may also provide an antiblock benefit, reducing the tendency of the elastic member to stick to itself, to substrates, or to processing equipment.

Further, it is possible to increase the resistance of the elastic member to certain ingredients of baby oils, lotions, gels, cremes, and the like, through the use of antiblock agents applied in a fluid or molten state to the outer surfaces of the elastic member. For certain embodiments of the present disclosure, suitable antiblock agents and suitable processes for applying the antiblock agents are disclosed in U.S. application Ser. Nos. 11/413,483 and 11/413,545 filed on Apr. 28, 2006 in the name of Arman Ashraf and Daniel Steven Wheeler which claims the benefit of U.S. Provisional Application Nos. 60/676,755 and 60/676,275, respectively, filed on Apr. 29, 2005.

Suitable substrates 14 (shown in FIGS. 1A-E) for use in an SRSL 10 include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof. For use in absorbent articles and particularly in diapers and like products, the substrate 14 is generally compliant, soft-feeling, and non-irritating to a wearer's skin. In certain embodiments, substrates 14 may include nonwoven webs such as spunbond webs, meltblown webs, carded webs, and combinations thereof (e.g., spunbond-meltblown composites and variants).

The dimensions of the substrate 14 are generally limited only by the requisite end-use of the SRSL 10.

The SRSL 10 embodiments of the present disclosure may exhibit unique elastic and recovery characteristics. The SRSL 10 may exhibit a normalized unload force of greater than about 0.16 N/(g/m) at 37° C. as measured by the Two Cycle Hysteresis Test. Normalized unload forces of less than about 0.12 N/(g/m) at 37° C. may not be sufficient for use as an elastomer within absorbent articles. Laminates having normalized unload forces less than 0.12 N/(g/m) at 37° C. may be unable to keep an absorbent article in snug, close contact to the wearer's skin. In certain embodiments, the SRSL 10 may exhibit a normalized unload force of greater than about 0.24 N/(g/m) at 37° C., or may exhibit a normalized unload force of greater than about 0.36 N/(g/m) at 37° C., or may exhibit a normalized unload force of greater than about 0.48 N/(g/m) at 37° C., or may exhibit a normalized unload force of greater than about 0.60 N/(g/m) at 37° C.

Conventional stretch laminates (i.e., such as those commonly found in absorbent articles including diapers) may exhibit minimal post elongation strain at 22° C. after 15 seconds of recovery. Qualitatively, conventional stretch laminates exhibit "snap back" (i.e., contracts relatively quickly after being released from a stretched state). In contrast, the SRSL 10 of the current invention may exhibit a percent of initial strain of about 10% or greater after 15 seconds of recovery at 22° C., as measured by the Post Elongation Recovery Test. In other embodiments, the SRSL 10 may exhibit a percent of initial strain of about 20% or greater after 15 seconds of recovery at 22° C. In other suitable embodiments, the SRSL 10 may exhibit a percent of initial strain of about 30% or greater after 15 seconds of recovery at 22° C. In other suitable embodiments, the SRSL 10 may exhibit a percent of initial strain of about 40% or greater after 15 seconds of recovery at 22° C.

Furthermore, the SRSL 10 embodiments of the present disclosure may exhibit a specified percent of initial strain at 22° C. after 30 seconds, 60 seconds, or three minutes of recovery. In certain embodiments, the SRSL 10 may exhibit a percent of initial strain at 22° C. after 30 seconds of recovery of about 10% or greater. In other embodiments, the SRSL 10 may exhibit a percent of initial strain at 22° C. after 30 seconds of recovery about 15% or greater. In other embodiments, the SRSL 10 may exhibit a percent of initial strain at 22° C. after 60 seconds of recovery of about 10% or greater.

The SRSL 10 may exhibit temperature responsiveness. In certain embodiments, the SRSL 10 may exhibit a percent of initial strain at 37° C. after a specified amount of recovery time that is less than the percent of initial strain exhibited at 22° C. after the same recovery time. In one embodiment, a temperature responsive SRSL 10 may exhibit a reduction in a percent of initial strain after 15 seconds at 37° C. as compared to the percent of initial strain exhibited after 15 seconds at 22° C. (i.e., [percent of initial strain after 15 seconds of recovery at 22° C.]–[percent of initial strain after 15 seconds of recovery at 37° C.]). In some embodiments, the difference is equal to or greater than 5%. In other embodiments, the SRSL 10 may exhibit a difference in the percent of initial strain after 15 seconds at 22° C. compared to after 15 seconds at 37° C. equal to or greater than 10%, 20%, 30%, or 40%. It is believed that an SRSL 10 exhibiting temperature responsiveness may further facilitate diaper application. When the diaper is applied at about room temperature (i.e., approximately 22° C.), the SRSL 10 may exhibit a relatively high percent of initial strain for a prescribed period of time, which allows the caregiver or wearer to apply the diaper. Upon application of the diaper, the temperature of the SRSL 10 will rise as a result of being in close proximity to the wearer's skin. As the temperature of the SRSL 10 increases and nears body temperature (i.e., approximately 37° C.), the percent of initial strain is reduced. Temperature responsiveness allows for application of the diaper without "snap-back" while providing for increased recovery after application.

The SRSL 10 may be utilized in a variety of consumer and commercial products. However, the SRSL 10 has particular benefit within absorbent articles, particularly disposable absorbent articles such as diapers and the like. The SRSL 10 may be used in a variety of regions or in a variety of article elements to provide elastic character to the absorbent article. It may be desirable to incorporate the SRSL 10 embodiments of the present disclosure into the absorbent articles disclosed in U.S. Pub. Nos. 2005-0273071, 2005-0171499, 2007-0191806, 2004-0162538, and 2005-0095942.

Another embodiment of the present disclosure is directed toward a method of applying any of the absorbent articles as disclosed above. The absorbent article may be provided to a caregiver for application onto a wearer. The absorbent article may be in a compacted state such that a stretch laminate comprising an SRSL is in a relaxed, substantially untensioned state. The caregiver may stretch the absorbent article thereby expanding and tensioning the stretch laminate. The article is generally stretched in preparation for application. The absorbent article can maintain a functionally elongated state for an effective period of time. In one embodiment, the article may maintain an elongated state for a sufficient amount of time necessary for the caregiver to apply the article to the wearer. With conventional diapers (not comprising SRSL), upon release of the diaper after stretching, the diaper often contracts and/or folds before it can be successfully applied to a wearer. In one embodiment, SRSL may exhibit a percent of initial strain after 15 seconds of recovery at 22° C. of greater than or equal to 10%. After application, the article may continue to contract so as to provide a snug, ideal fit.

In another embodiment, a plurality of absorbent articles as disclosed above may be packaged in a kit. Generally, the kit allows for a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous absorbent articles bound together as an entity and covered by a thermoplastic film overwrap as disclosed in U.S. Pat. No. 5,934,470. The thermoplastic film cover may contain an opening means to allow removal of a portion of the thermoplastic film cover and access to the articles. An opening means may include a substantially continuous line of weakness, including perforations within the thermoplastic film cover. An opening means that may be used is presented in U.S. Pat. No. 5,036,978.

While one kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of absorbent articles. Other useful packages and methods for packaging are disclosed in U.S. Pat. Nos. 5,050,742 and 5,054,619. Furthermore, a kit may contain multiple overwraps. For example, a plurality of absorbent articles of the present disclosures may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Test Methods
Post Elongation Recovery

This method is used to determine the post elongation strain of a stretch laminate as a function of temperature and time, and with certain variations as described below is used to determine the post elongation strain of an elastomer as a function of temperature and time. The measurement is done at 22° C. (72° F.) or at 37° C. (99° F.). The measurement at 22° C. (72° F.) is designed to simulate the recovery of the stretch laminate (or elastomer) at room temperature, while the measurement at 37° C. (99° F.) is designed to measure the recovery of the stretch laminate (or elastomer) near body temperature. Other test temperatures are within the scope of this method including, but not limited to, the recovery of the stretch laminate (or elastomer) near skin temperature (32° C.). A two-step analysis, Stretch and Recovery, is performed on the samples. The method employs a Dynamic Mechanical Analyzer. A TA Instruments DMA Q800 (hereinafter "DMA Q800"), available from TA Instruments, Inc., of New Castle, Del.; equipped with a film clamp, Thermal Advantage/Thermal Solutions software for data acquisition, and Universal Analysis 2000 software for data analysis was used herein. Many other types of DMA devices exist, and the use of dynamic mechanical analysis is well known to those skilled in the art of polymer and copolymer characterization.

Methods of operation, calibration and guidelines for using the DMA Q800 are found in TA Instruments DMA Q800 Getting Started Guide issued July 2007, Thermal Advantage Q Series™ Getting Started Guide issued February 2004 and Universal Analysis 2000 guide issued May 2004. To those skilled in the use of the DMA Q800, the following operational run conditions should be sufficient to replicate the stretch and recovery of the samples.

The DMA Q800 was configured to operate in the Controlled Force Mode with the film clamp. The film clamp is mounted onto the DMA Q800 and calibrated according to the User's Reference Guide. The stretch laminate (or elastomer) to be tested is cut into samples of substantially uniform dimension. For the DMA Q800, suitable sample dimensions are approximately 20 mm×6.4 mm×1.0 mm (length×width×thickness). The sample thickness of the stretch laminate is dependent on the materials and structure of the stretch laminate and on the confining pressure used to measure the thickness. TA Instruments recommends the sample thickness, when securely mounted within the film clamps, to be less than or equal to about 2.0 mm. The lower film clamp of the DMA Q800 is adjusted and locked in a position which provides approximately 10 mm between the clamping surfaces. The sample is mounted in the film clamps and the lower clamp is allowed to float to determine the gauge length between the film clamps. It should be understood that the sample referenced in this method is one where the SRSL must run from the upper clamp to the lower clamp. The sample ID and dimensions are recorded. The film clamp is locked in position and the furnace is closed.

Stretch Method—For the sample dimensions specified above, the DMA Q800 is configured as follows: Preload force applied to sample in clamp (0.01N); auto zero displacement (on) at the start of the test; furnace (close), clamp position (lock), and temperature held at $T_i$ (22° C. or 37° C.) at the end of the stretch method. Data acquisition rate is set at 0.5 Hz (1 point per 2 seconds). The stretch method is loaded onto the DMA Q800. The method segments are (1) Initial Temperature T; (22° C. or 37° C.), (2) Equilibrate at $T_i$ (3) Data Storage ON, and (4) Ramp Force 5.0 N/min to 18.0 N.

Upon initiation of the test, the temperature ramps to the specified $T_i$, (22° C. or 37° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 0.8 N/min per millimeter of initial sample width (e.g., for the sample dimensions specified above, the applied ramp force is 5 N/minute) to approximately 30 mm in length. The gradual increase in force more closely simulates application of the article and prevents sample breakage. The sample is locked in place at the stretched length of approximately 30 mm and maintained at $T_i$. The force required to stretch the laminate to a length of approximately 30 mm and the percent strain of the laminate at this length are recorded manually from the digital readout on the instrument. The percent strain is calculated by subtracting the gauge length from the stretched length, then dividing the result by the gauge length and multiplying by 100. The initial percent strain is described by the equation below:

Initial Percent Strain=% Strain$_i$=100*[(Ls–$L_g$)/$L_g$]

where $L_g$ is the gathered length of the relaxed stretch laminate (or elastomer) between the film clamps at the beginning of the stretch step, and Ls is the length of the stretched laminate (or elastomer) between the film clamps at the end of the stretch step of the analysis (~30 mm). The % Strain$_i$ is the percent strain of the stretch laminate (or elastomer) at the start of the recovery method (i.e., after the stretch part of the method is complete). A sample stretched from a gauge length of 10 mm to a length of 30 mm results in a percent strain of 200%.

Stretch laminates may be unable to exhibit extensibility of 200% strain without incurring irreversible deformation, delamination, tearing, or a significant percent set (i.e., set of greater than about 10%). This is particularly true for stretch laminates obtained from commercially available products such as the side panels, leg cuffs and waistbands of diapers. For example, a stretch laminate (~6.4 mm wide) may be easily stretched to 100% strain or 150% strain when relatively low forces (<4N) are applied. However, if the applied force continues to increase to achieve 200% strain, the percent strain of the stretch laminate plateaus and further extension may be difficult and/or may result in irreversible deformation, delamination, tearing, or significant percent set (i.e., set of greater than 5%) of the stretch laminate. For stretch laminates, the initial percent strain (% Strain$_i$) is taken as 70% of the average maximum percent strain determined according to the Maximum Laminate Strain Test rounded up to the nearest multiple of five if the value does not result in a target strain that is divisible by five when rounded to the nearest percent. For example, if 70% of the average maximum percent strain is equal to 187.1%, this value is not divisible by 5 when rounded to the nearest percent (187%), so the initial percent strain would be taken as 190%. Also, for example, if 70% of the average maximum percent strain is equal to 180.1%, this value is divisible by 5 when rounded to the nearest percent (180%), so the peak strain would be taken as 180%. For laminates with an average maximum percent strain of greater than 536%, an initial percent strain of 375% is used. For elastomers or elastomeric films (or stretch films), the initial percent strain is 400%. The required gathered length of the relaxed laminate (or elastomer) between the film clamps at the beginning of the stretch step can be approximated from the initial percent strain determined above using the initial percent strain equation above.

For samples of different dimensions, the applied force to stretch the sample is adjusted to achieve an applied ramp force of 0.8 N/min per millimeter of initial sample width. For example, a force ramp of 2.5 N/min is applied to a sample with an initial width of 3.2 mm.

Recovery Method—The Recovery Method is loaded onto the instrument and initiated approximately 15 seconds after reaching the desired initial percent strain (% Strain$_i$) in the Stretch Method. The four segments of the recovery method are (1) Data Storage ON, (2) Force 0.01N, (3) Ramp to $T_i$, and (4) Isotherm for 3.0 minutes. The following DMA Q800 parameter setting is changed from the Stretch Method: auto zero displacement is changed to (OFF). The Recovery Method measures the length of the sample over a 3 minute time period at the specified temperature ($T_i$=either 22° C. or 37° C.). The sample length, percent strain, and test temperature are recorded as a function of recovery time. The post elongation strain is reported as the percent of the initial percent strain after different times of recovery (15 seconds, 30 seconds, 60 seconds, and 3 minutes). For example, if the initial percent strain is 400% and the percent strain after 15 seconds of recovery at 22° C. is 50%, then the percent of initial strain after 15 seconds of recovery at 22° C. is reported as 12.5% (=100×50%/400%).

For samples of different dimensions, the force applied to the sample during recovery (segment 2 above) is adjusted to achieve an applied force of 0.0016 N per millimeter of initial sample width (0.01N for 6.4 mm wide sample). For example, a force of 0.005 N is applied to a sample 3.2 mm wide.

Order-Disorder Temperature

The order-disorder temperature (ODT) is determined using a parallel plate rheometer to measure the shear storage modulus (G'), the shear loss modulus (G"), and the loss tangent (G"/G') as a function of temperature in oscillatory shear mode. In the examples, the materials are tested on a TA instruments (New Castle, Del.) AR-G2 stress-controlled rheometer equipped with an environmental test chamber (ETC) and using the "dynamic temperature ramp test" in controlled strain mode. Other rheometers, including both strain and stress controlled, are satisfactory as long as (i) the material is analyzed in the linear viscoelastic region, (ii) if the instrument is stress controlled and operated in the controlled strain mode, the electronic feedback rate is sufficiently fast compared to the temperature ramp rate, and (iii) standard methods and setup for the testing rheometer are followed, for example for the AR-G2 these include calibrating the instrument inertia, bearing friction correction, and geometry inertia, as well as geometry mapping (3 iterations in precision mapping mode) at the start of each testing session (at least daily). The basic environment and testing conditions are as follows: (i) nitrogen atmosphere, (ii) 25 millimeter diameter parallel plates (steel preferred), (iii) angular frequency of 1.0 radians per second, (iv) starting temperature of 40° C., and (v) temperature ramp rate of 3° C. per minute. Other test conditions are within the scope of this method.

Sample loading. After setting up the rheometer per the manufacturer's instructions, the 25 mm parallel plates are brought together and zeroed at an equilibrated temperature of 40° C. The temperature of the plates are increased to 100° C., the ETC is opened and the upper plate is raised to allow a sample disc to be placed on the lower plate, the upper plate is then lowered until it contacts the sample with a slight normal force (3-5 Newton's), and finally the ETC is closed. The sample starting thickness is about 1.0-1.5 millimeters and the starting diameter is about 27 millimeters, where the sample disc is cut from a compression molded sample using a round hole arch punch with a diameter of 1 1/16 inches (molded samples can be prepared according to the film preparation method given in the Example 1). After about 1 minute, the ETC is opened, the sample is trimmed to remove any excess material extending beyond the edge of the parallel plates, and then the ETC is closed. If necessary, before the ETC is closed, the gap is narrowed to ensure that the sample bulges out slightly from the edge of the plates. The sample temperature is lowered back to 40° C. utilizing the auto-tension (hold) function to ensure constant contact between the plates and sample while the temperature is decreased (a 0.5 Newton normal force is often sufficient). Some materials may not be sufficiently soft at 100° C. to allow trimming of the sample. In these cases, it is recommended to increase the temperature in 10° C. increments until the sample is soft enough to trim. After trimming, the temperature is then lowered to 40° C. following the procedure above.

Determining test strain for dynamic temperature ramp test. After sample loading, and once the temperature is equilibrated at 40° C., an oscillatory strain (or stress) sweep is carried out at an angular frequency of 1.0 radians per second to determine the percent strain that is achieved at an oscillatory stress of about 2000 Pascal's. If this percent strain is within the linear viscoelastic region at these test conditions, this is the test strain used in the dynamic temperature ramp test to determine the ODT of this sample. If this strain is beyond the linear viscoelastic range at these test conditions, then the highest strain within the linear region is used as the test strain in the dynamic temperature ramp test. For certain embodiments of the present disclosure, an oscillatory stress of about 2000 Pascal's may not be high enough to avoid unacceptable noise in the system response, e.g., as evidenced by large scatter in either the shear storage or shear loss modulus as the oscillatory stress approaches and exceeds 2000 Pascal's. In those cases, a higher oscillatory stress may be necessary, and as long as the sample remains within the linear viscoelastic range higher applied stresses are within the scope of this method.

Figure 2:
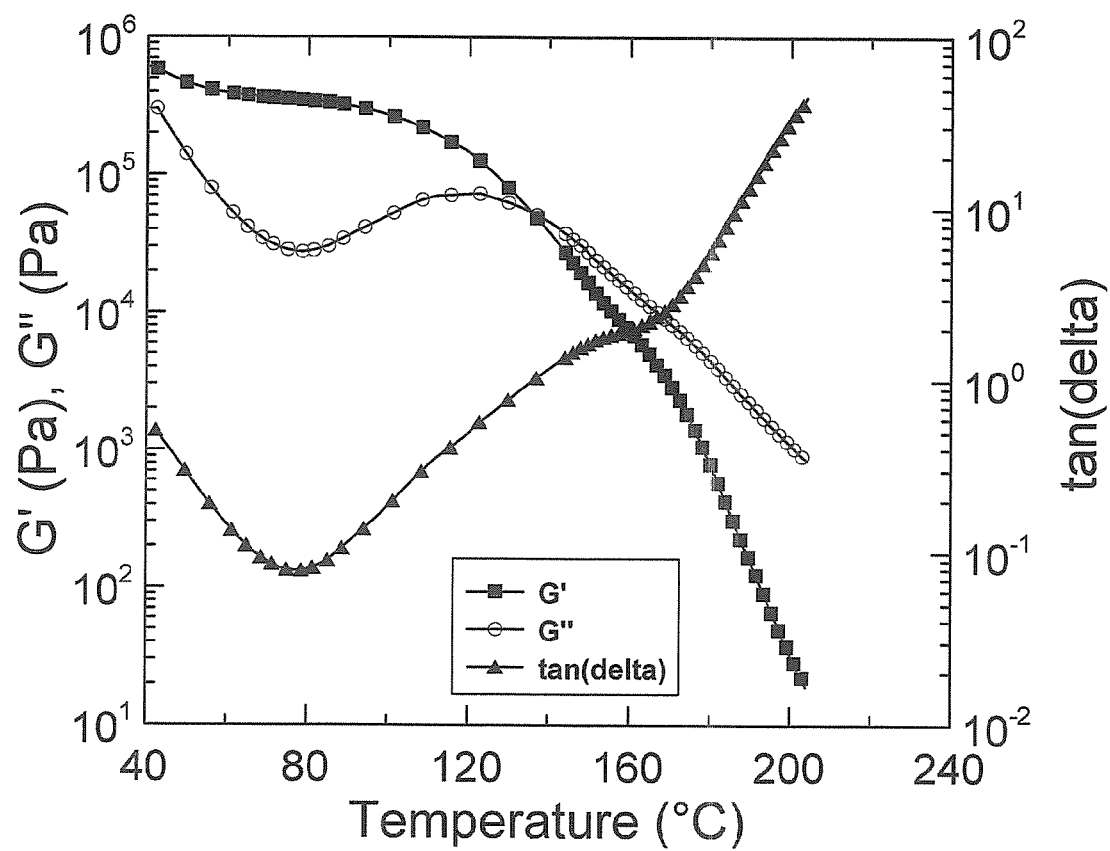
FIG. 2 shows the shear storage modulus (G'), the shear loss modulus (G"), and the loss tangent for an embodiment of an elastic member of the present disclosure.

Determining order-disorder temperature from a dynamic ramp test. Using the same loaded sample as used in determining the test strain, a dynamic temperature ramp test is initiated at 40° C. and the temperature is increased by 3° C. per minute until either the storage modulus drops below about 20 Pascal's or the test temperature exceeds 250° C. Test temperatures should be limited to a maximum of 250° C. as block copolymer based materials can start to degrade around this temperature (even with a nitrogen atmosphere). Measurements are taken about every 3° C. while the upper plate is rotated in a sinusoidal manner at an angular frequency of 1.0 radians per second and the degree of deformation applied to the material (strain) is set to the percent strain determined from the oscillatory strain (stress) sweep described above. Outputs of the test versus temperature are the shear storage modulus (G'), shear loss modulus (G"), and loss tangent (G"/G' or tan δ, where δ is the mechanical loss angle). An example of an inventive material (Film Sample F3, Table 2) is shown in FIG. 2. Within the present disclosure, the ODT is taken as the temperature at which the loss tangent is equal to 2.0 as determined using the test conditions and methods delineated within this experimental method. As a secondary check of the ODT, the storage modulus may be less than $10^4$ Pascal's and may be around a few thousand Pascal's at this temperature. For materials that do not exhibit an ODT of less than or equal to 250° C., the ODT is designated as "greater than 250° C." (>250° C.). A minimum of two samples of each material is measured for its ODT, and the arithmetic average is reported as the ODT.

Hard Block Glass Transition Temperature

Differential Scanning calorimetry (DSC) is a well known method for thermal measurements. This method is capable of determining the temperature ranges at which phase changes of materials occur, e.g., glass transition temperatures or crystalline melt temperatures. Here, for example, the glass transition temperature (Tg) is useful for (i) selecting hard phase modifiers that may increase the hard phase glass transition temperature of a block copolymer composition, (ii) determining whether ingredients such as modifying resins and processing oils may depress the hard phase glass transition temperature, or (iii) determining whether the net effect of the hard phase associating ingredients such as modifying resins, processing oils, and hard phase modifiers may lead to an increase, decrease, or no change in the hard phase glass transition temperature. Within the scope of this method are the glass transitions temperatures for hard blocks, hard phases, soft blocks, and soft phases.

The measurements are performed using a Model 822 DSC from Mettler, Columbus, Ohio or a System 7 DSC from Perkin-Elmer, Shelton, Conn. or equivalent instrumentation. The instrument is interfaced with a computer for controlling the heating/cooling rates and other test parameters, and for collecting, calculating and reporting the data. The test procedure follows that of ASTM D3418 generally. The procedure is as follows:

(1) calibrate the instrument according to the manufacture's instructions;

(2) for single materials, for example an equivalent hard block (EHB) polymer, e.g., a polystyrene homopolymer with a weight average molecular weight of about 35 kilo Daltons and a narrow molecular distribution available for example as a polystyrene molecular weight standard from Sigma-Aldrich, Inc., St. Louis, Mo., or from Polysciences, Inc., Warrington, Pa., a sample material (ca. 15 mg) is placed into a clean aluminum pan, capped, crimped and placed into the instrument according to manufacturer's instructions.

(3) for polymer blends, for example a blend of an EHB polymer and a hard phase modifier, the EHB polymer, e.g., the polystyrene homopolymer as described above is blended with a hard phase modifier, e.g., tetramethyl bisphenol-A polycarbonate (TMBAPC), in a weight ratio of EHB polymer to hard phase modifier equivalent to the weight ratio of hard block to hard phase modifier in the block copolymer composition. The blending can be accomplished by any standard means known in the art including, but not limited to, melt blending, e.g., such as described in Example 1 in the Examples Section, or solution blending using a solvent suitable for dissolving both the EHB polymer and the hard phase modifiers, e.g., such as described in Example 15 in the Examples Section. A sample of the blended material (ca. 15 mg) is placed into a clean aluminum pan, capped, crimped and placed into the instrument according to manufacturer's instructions.

(3) if testing a new material or blend, for example, a new EHB polymer, hard phase modifier, or other hard phase or soft phase associating ingredients, it may be necessary to perform one or more trial scans to determine an appropriate temperature range for the measurements, which should provide sufficient baseline before and after the observed transition; a temperature scan may range from −50° C. to about 50° C. above the highest phase transition temperature of the sample being tested; for hard phase associating ingredients of the present disclosure, a DSC scan may range from −50° C. to 250° C.

(4) program the instrument as follows: the sample temperature is set to the lower limit of desired test range; the temperature is held at the lower limit for 5 minutes and then it is increased at a rate of 10° C./min until reaching the upper limit; the temperature is held at the upper limit for 5 minutes and then the sample is cooled to the lower limit at 10° C./min; the temperature is held at the lower limit for 5 minutes and then the sample is heated at 10° C./min to the upper limit for a second heating scan;

(5) start the test and collect data simultaneously;

The results are analyzed using the procedure described in ASTM D 3418, Standard Test for Transition Temperatures of Polymers by Differential Scanning calorimetry. The results are reported from the second heating cycle. The midpoint temperature of the glass transition is determined according to the procedure of ASTM D 3418 and is taken as the glass transition temperature.

Other polymer blends are within the scope of this method including, but not limited to, blends of the EHB polymer with ingredients such as modifying resins and processing oils, and blends of the EHB polymer with hard phase modifiers, modifying resins and processing oils. Additionally, EHB polymers other than polystyrene and hard phase modifiers other than TMBAPC are also within the scope of this method. Further, for this method, the number average molecular weight of the EHB polymer ranges from about 0.5× to about 5× the number average molecular weight of the corresponding hard block of the block copolymer composition.

Maximum Laminate Strain

The maximum laminate strain is that strain above which a stretch laminate may sustain irreversible deformation, delamination, tearing, or a significant percent set (i.e., set of greater than 5%). In a tensile test, such as described in ASTM D 882, the maximum laminate strain may be associated with a relatively steep rise in the tensile force with increasing tensile strain (not including the initial rise that occurs at very low strains, often at less than about 15 percent engineering strain).

The tensile test is performed at room temperature (about 22° C.). The stretch laminate to be tested is cut into a sample of substantially rectilinear dimensions. Sample dimensions are selected to achieve the required strain with forces appropriate for the instrument. Suitable instruments for this test include tensile testers from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 16 millimeters wide by approximately 75 millimeters long.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The width of the grips used for the test is greater than or equal to the width of the sample. 1 inch (2.54 cm) wide grips may be used. The grips are air actuated grips designed to concentrate the entire gripping force along a single line perpendicular to the direction of testing stress having one flat surface and an opposing face from which protrudes a half round (radius=6 mm) to minimize slippage of the sample.

The load cell is selected so that the forces measured will be between 10% and 90% of the capacity of the load cell or the load range used. A 25 Newton load cell may be appropriate. The fixtures and grips are installed. The instrument is calibrated according to the manufacturer's instructions. The distance between the lines of gripping force (gage length) is 1.0 inch (25.4 millimeters), which is measured with a steel ruler held beside the grips. The load reading on the instrument is zeroed to account for the mass of the fixture and grips. The specimen is equilibrated a minimum of 1 hour at about 22° C. before testing. The specimen is mounted into the grips in a manner such that there is no slack and the load measured is between 0.00 Newton's and 0.02 Newton's. The instrument is located in a temperature-controlled room for measurements performed at about 22° C. and a crosshead speed of 20 inches per minute. The test is initiated and the specimen is extended at 20 in/min until it breaks. The data acquisition rate is 200 Hertz for strains up to about 40% engineering strain, and 50 Hertz for strains above about 40%.

Figure 3:
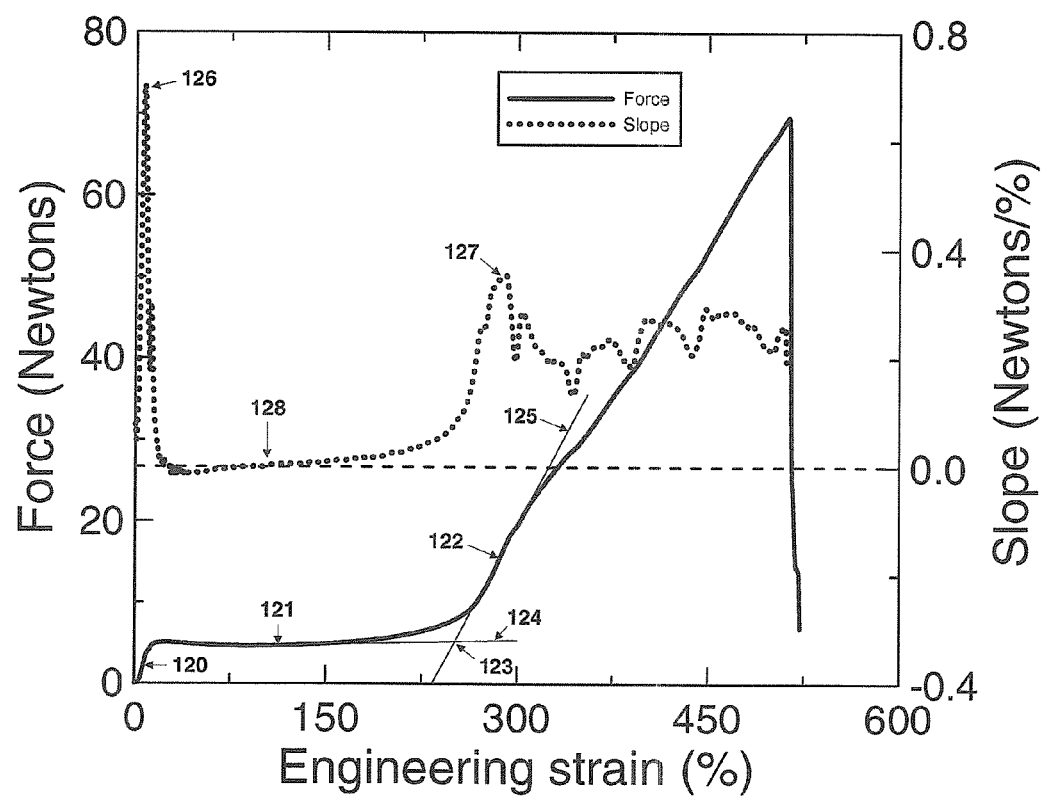
FIG. 3 shows a force-engineering strain curve for a stretch laminate embodiment and illustrates the approach for determining the maximum laminate strain.

Outputs of the tensile test include the sample strain (engineering strain) and the corresponding tensile force, where an example of an inventive material (Laminate Sample L2, Table 5) is shown in FIG. 3. There may be a small rise 120 in the force at low strains, followed by a relatively flat plateau region 121 corresponding to the primary stretch region of the laminate, and then past the stretch region there is a steep rise 122 in the measured force with increasing sample strain. The maximum laminate strain is taken as the intersection 123 of two linear lines drawn on the tensile force-strain curve: (i) the plateau region 124, and (ii) the steep rise region 125. For samples that exhibit a yield drop (such as shown in FIG. 3), line 124 is the tangent line to the force-strain curve at the highest strain value 128 between the initial rise 120 and steep rise 122 regions where the slope of the force-strain curve is equal to zero. For samples that don't exhibit a yield drop, line 124 is the tangent line to the force-strain curve at the strain value between the initial rise 120 and steep rise 122 regions where the slope of the force-strain curve reaches its minimum value. Line 125 is the tangent line at strain point 127 where the slope of the force-strain curve reaches its first peak value in the steep rise region 122, e.g., where the second derivative of the force-strain curve is equal to zero. For the crosshead speed and data acquisition rates mentioned above, the tangent line at each strain point is taken as the slope of a linear regression line through the following seven force-strain data points—(i) the force-strain value at the specific strain, (ii) the force-strain values at the three strain points before the specific strain, and (iii) the force-strain values at the three strain points after the specific strain. The number of data points per regression line are chosen such that there is less than a 5% change in the strain value at the intersection 123 upon increasing and decreasing the number of data points per regression line in increments of two, e.g., increasing the number of data points from seven points per regression line to nine points per regression line, where in all cases the regression is set up so there is an equal number of data points before and after the specific strain included in the linear regression analysis. A minimum of five samples of each stretch laminate is measured for its maximum laminate strain, and the arithmetic average is reported as the maximum laminate strain.

Elastomer and Laminate Aging Method

In this method elastic films or laminates are held under stretched conditions for 1 week at 40° C.±2° C. to simulate extended product storage. The relative humidity can be anywhere within the 20-80% range, but should be maintained at the same relative humidity (±5%) throughout the aging test. The aging strain applied to the elastomeric film is 100% engineering strain after a 300% engineering prestrain, and the aging strain applied to the stretch laminate is 50% engineering strain with no prestrain (as the elastomeric component of the stretch laminate is generally prestretched during the manufacturing of the laminate, such as described in the Laminate Preparation section of Example 3). In the examples, tested films have a starting width of about 20 millimeters and a starting gage length 133 (FIG. 4A) of about 2.5 inches, while tested laminates have a starting width of about 16 millimeters and a starting gage length of about 2.5 inches. In addition, the overall lengths of the tested films and laminates are about 4.5 inches to help hold the samples in a stretched state and for gripping the sample during property testing (e.g., two-cycle hysteresis), where the approximately 1.0 inch sample areas outside the gage area are covered with masking tape 131 to help keep these areas from stretching during the setup and aging process. Further, a reference line 132 is drawn on the film or laminate sample along the interface between the tape 131 and stretch 130 areas. A ball point ink pen is recommended for the marking, but other types of markers are acceptable as long as they do not interact with the sample to cause premature failure or other negative reactions. Other test forms including, but not limited to, elastomer fibers, strands, and nonwovens, and other test form dimensions are within the scope of this method.

In the examples, wood boards covered with double-sided silicone release paper are used to hold the samples in a stretched state, and the boards are sized to hold up to ten samples side-by-side with about a 1.0 inch spacing. The samples are stretched and mounted to the board at room temperature. For films, one taped end of the test sample is stapled to the board, the other taped end is then stretched to a length that results in 300% engineering strain within the non taped stretch area (e.g., stretched 7.5 inches based on a 2.5 inch gage length), held for 10 seconds, and stapled to the board at a distance that results in 100% engineering strain within the non taped stretch area (e.g., to 5.0 inches based on a 2.5 inch gage length). For laminates, one taped end of the test sample is stapled to the board, the other taped end is stretched to a length that results in 50% engineering strain within the non taped stretch area (e.g., 3.75 inches based on a 2.5 inch gage length) and then stapled to the board. Also for films, a light coating of talc or particulate starch may be applied to help keep the film samples from sticking to themselves or to the release paper.

This procedure is continued until all the samples to be aged are mounted on the board. Then, on each of the taped ends, a steel bar about 1.0 inch wide and 0.25 inches thick is placed across the taped areas, making sure not to touch any of the bare film or laminate. A steel shim about 1.0 inch wide and about 0.7 millimeters thick is placed under the board, even with the bar above, and then C-clamps are used to hold the three pieces together (bar+board+shim). A total of 3 C-clamps are used per side. The bars help distribute the sample tension force over a larger area than the staples, and help minimize damage to the samples during the aging. The board with the stretched samples is then placed in a constant temperature constant humidity room for 1.0 week (40° C.±2° C., 75%±5% relative humidity). A minimum of five samples of each material is tested.

Figures 4A, 4B, 4C:
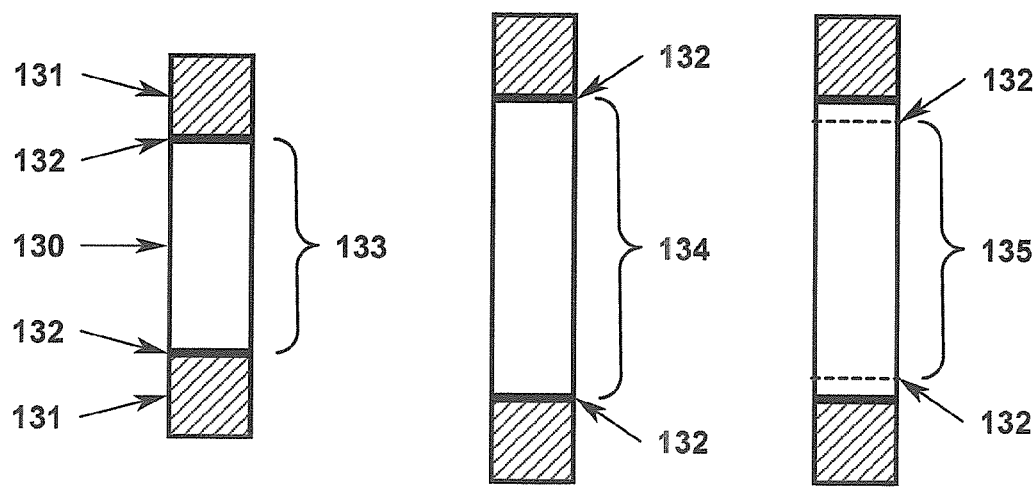
FIGS. 4A-C show a representative illustration of the Elastomer and Laminate Aging method test samples.
Figure 5A:
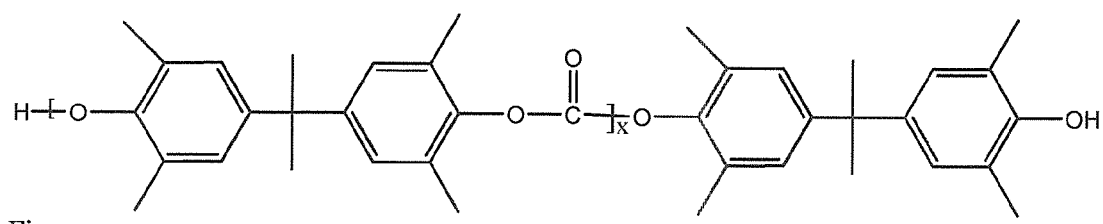
FIG. 5a shows the structure of tetramethyl bisphenol-A polycarbonate (TMBAPC).
Figure 5B:
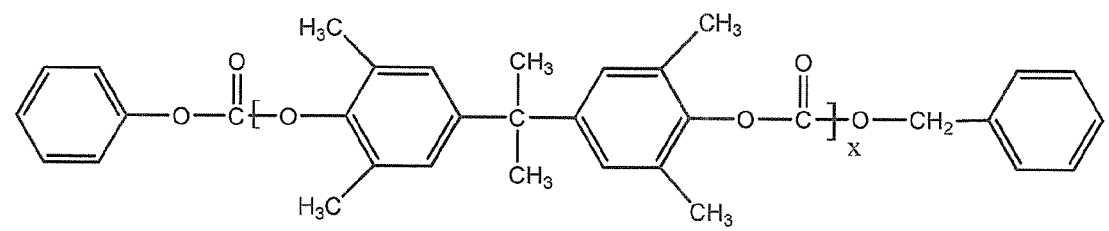
FIG. 5b shows the structure of TMBAPC with benzyl end groups.
Figure 6:
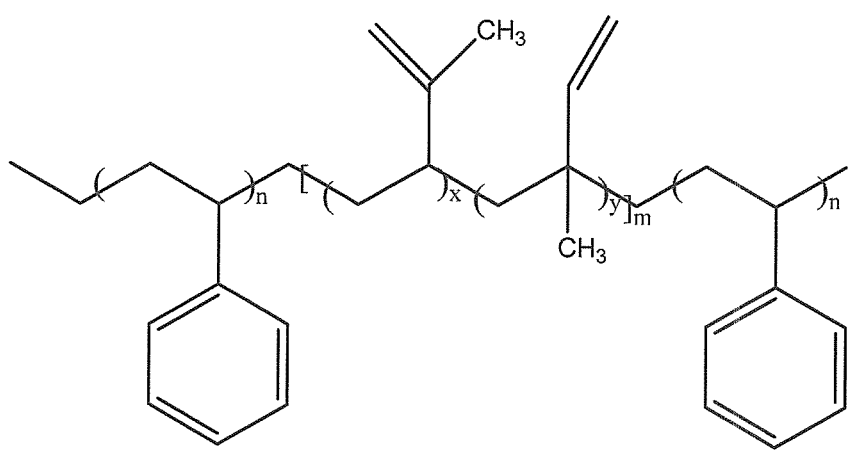
FIG. 6 shows the structure of a polystyrene block copolymer with a high 1,2- and 3,4-isoprene soft block.
Figure 7A:
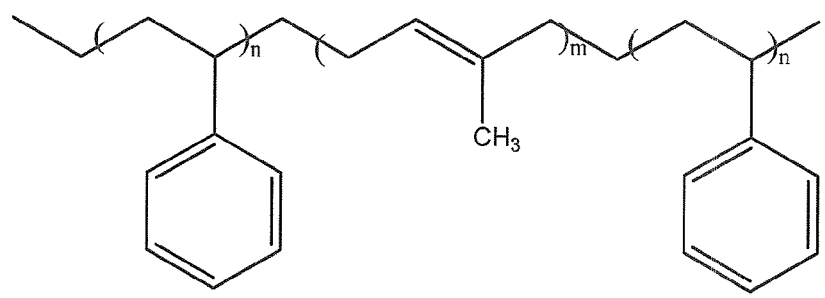
FIG. 7a shows the structure of a polystyrene block copolymer with an isoprene soft block.
Figure 7B:
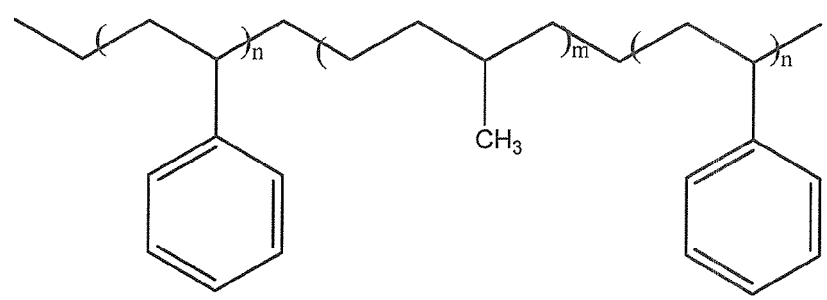
FIG. 7b shows the structure of a polystyrene block copolymer with an ethylene/propylene soft block.
Figure 7C:
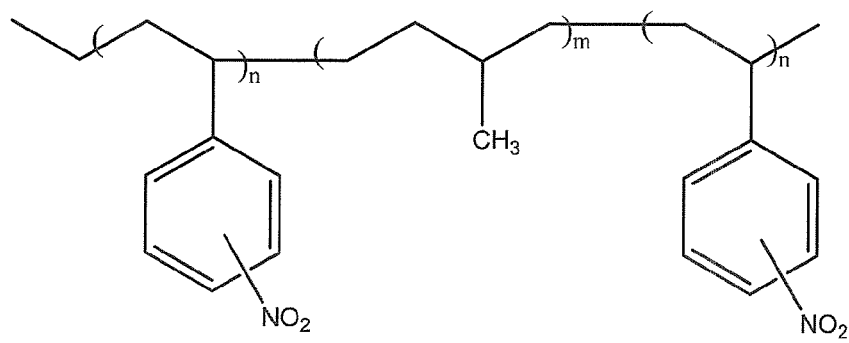
FIG. 7c shows the structure of a polystyrene block copolymer with an ethylene/propylene soft block and a nitrated hard block where the degree of nitration depicted is 100%.
Figure 8A:
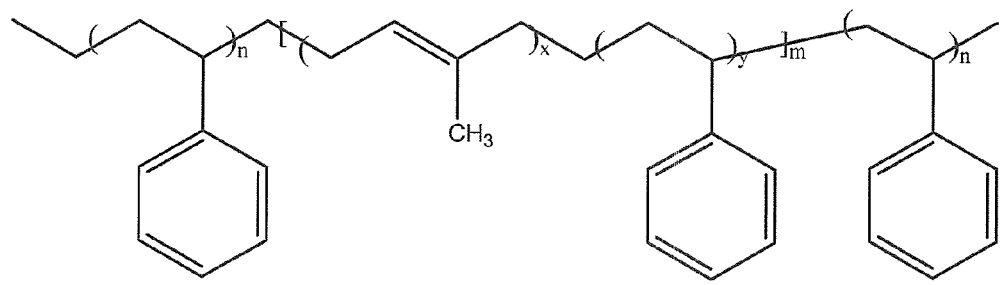
FIG. 8a shows the structure of a polystyrene block copolymer with a random styrene-isoprene soft block.
Figure 8B:
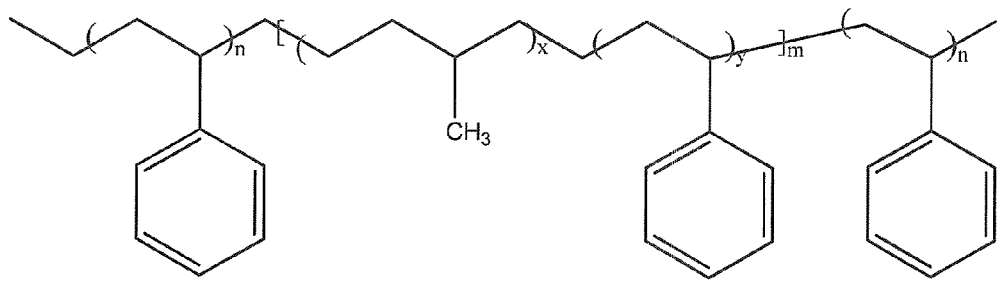
FIG. 8b shows the structure of a polystyrene block copolymer with an random styrene-ethylene/propylene soft block.
Figure 8C:
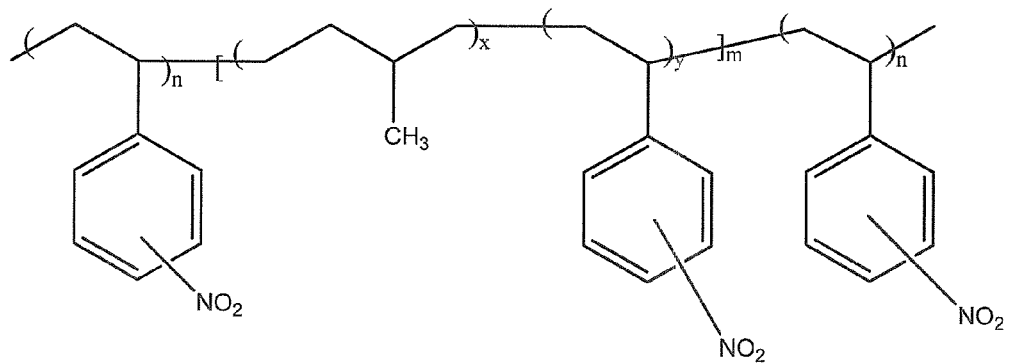
FIG. 8c shows the structure of a polystyrene block copolymer with a random nitrated styrene-ethylene/propylene soft block and a nitrated hard block where the degree of nitration depicted is 100%.
Figure 9A:
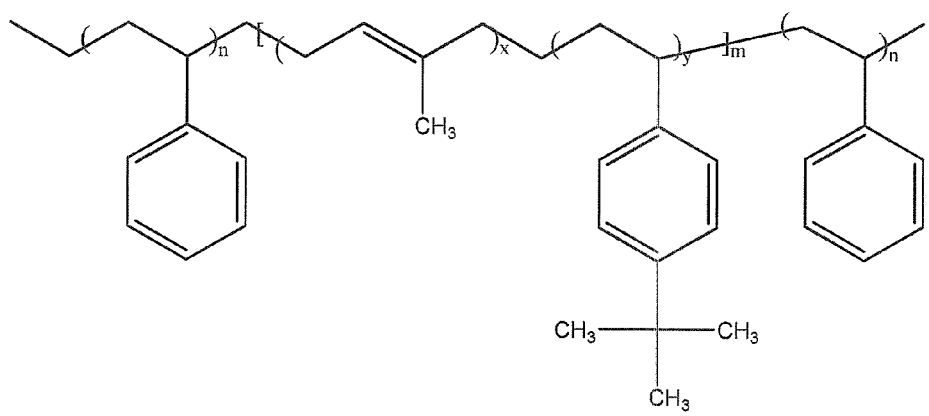
FIG. 9a shows the structure of a polystyrene block copolymer with a random t-butyl styrene-isoprene soft block.
Figure 9B:
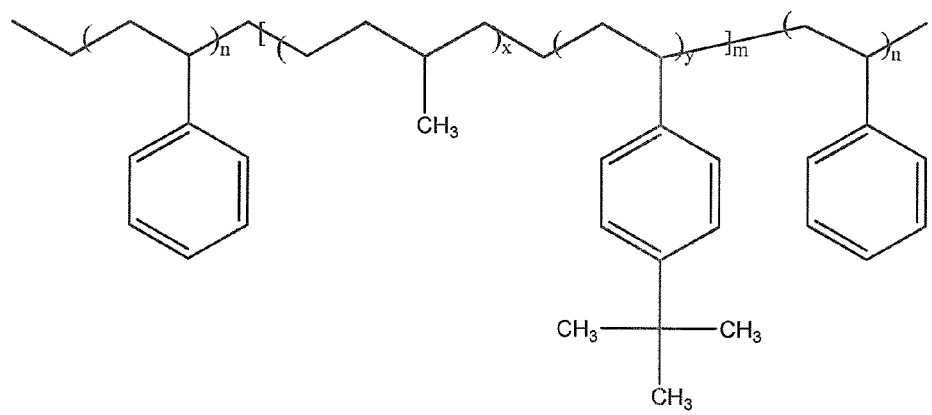
FIG. 9b shows the structure of a polystyrene block copolymer with an random t-butyl styrene-ethylene/propylene soft block.
Figure 9C:
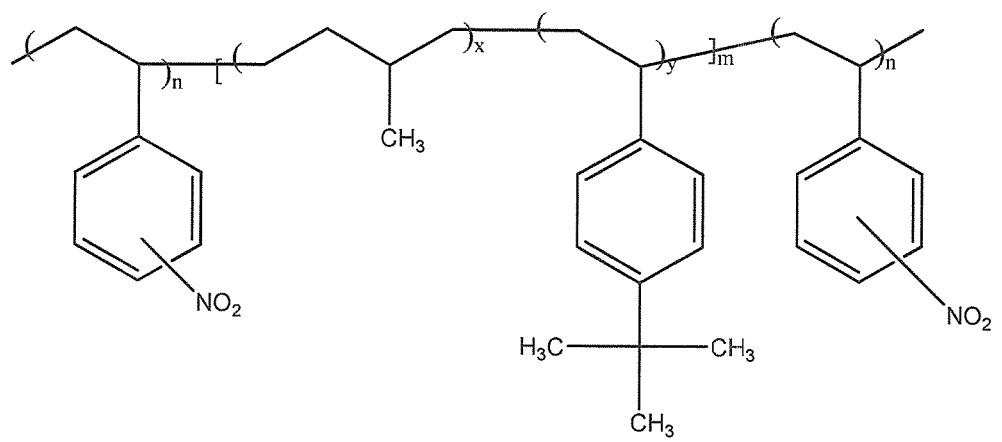
FIG. 9c shows the structure of a polystyrene block copolymer with a random t-butyl styrene-ethylene/propylene soft block and a nitrated hard block where the degree of nitration depicted is 100%.

Once the aging process is complete, the samples are removed from the board and immediately allowed to recover for 10 minutes at room temperature (about 22° C.) hanging vertically, followed by another 10 minutes of recovery at 40° C. laying flat on release paper. The length of the stretch zone 134 (FIG. 4B) is then measured to determine the percent permanent set. In certain embodiments of the present disclosure, the position of one or both of the reference lines 132 may move during the aging process, e.g., as a result of material being pulled from under the masking tape 131 (FIG. 4C). In this circumstance, the length of the stretch zone 135 is taken as the distance between the new positioned reference lines 132 (FIG. 4C). Further, the new positioned reference lines 132 may not be parallel with the tape/sample interface (as illustrated in FIG. 4C). In this situation, the length of the stretch zone 135 is taken as the average distance between the new positioned reference lines 132. The samples are then allowed to fully recover by placing them in a 30° C. oven and measuring the length of the stretch zone about every 12 hours. Complete recovery is considered less than a 5% change in length in a 12 hour time period. After recovery is complete, the samples are stored securely for at least 12 hours at room temperature before testing.

For sample evaluation by either the Two Cycle Hysteresis Test For Elastomers or the Two Cycle Hysteresis Test For Laminates, the distance between the lines of gripping force, i.e., the two-cycle hysteresis test gage length, is equal to the starting gage length 133 of the samples before aging. The sample is mounted into the grips such that the line of gripping force is centered on the reference lines 132, irrespective of whether the reference lines 132 have remained at the tape/sample interface (FIG. 4B) or have moved during the aging process (FIG. 4C). Further, for elastomer or laminate samples that sustain any permanent set after the aging and recovery protocol described above, there may be some slack in the mounted sample. In these cases, the tensile tester crosshead may have to move some distance before a sustainable finite force is observed during the first load cycle. This procedure is intended to simulate the permanent set and resulting force loss that may occur with a full product during storage in its compressed package.

For elastomer films, the corresponding non-aged control samples are prestrained to 300% engineering strain and allowed to recover according to the method described above. For laminates, the corresponding non-aged control samples are generally either an "as received" laminate, e.g., a laminate obtained from a commercial product, or an "as produced" laminate, e.g., a laminate produced according to the Laminate Preparation Method disclosed in Example 3.

Two Cycle Hysteresis Test for Elastomers

This method is used to determine properties of slow recovery elastomers, including the form of flat films, which may correlate with the forces experienced by the consumer during application of the product containing the elastomeric composition and how the product fits and performs once it is applied. Other sample forms including, but not limited to, fibers, strands, and nonwovens are within the scope of this method.

The two cycle hysteresis test method is performed at room temperature (22° C./70° F.) or at body temperature (37° C./99° F.). The material to be tested is cut into a substantially rectilinear shape. Sample dimensions should be selected to achieve the required strain with forces appropriate for the instrument. Suitable instruments for this test include tensile testers from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 0.13 mm thick, approximately 20 mm wide by approximately 100 mm long.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are wider than the sample. 1 inch (2.54 cm) wide grips may be used. The grips are air actuated grips designed to concentrate the entire gripping force along a single line perpendicular to the direction of testing stress having one flat surface and an opposing face from which protrudes a half round (radius=6 mm) to minimize slippage of the sample.

The load cell is selected so that the forces measured will be between 10% and 90% of the capacity of the load cell or the load range used. A 25 Newton load cell may be used. The fixtures and grips are installed. The instrument is calibrated according to the manufacturer's instructions. The distance between the lines of gripping force (gauge length) is 2.50 inches (63.5 mm), which is measured with a steel ruler held beside the grips, unless specified otherwise. The load reading on the instrument is zeroed to account for the mass of the fixture and grips. The mass, thickness, and basis weight of the specimen are measured before testing. The specimen is mounted into the grips in a manner such that there is no slack and the load measured is between 0.00 Newton and 0.02 Newton, unless specified otherwise. The instrument is located in a temperature-controlled room for measurements performed at 22° C. A suitable environmental chamber is used to maintain the testing temperature for measurements performed at 37° C.; the sample is mounted in the grips and equilibrated for 5 minutes at 37° C. before starting the test.

For elastomer samples that have been aged according to the Elastomer and Laminate Aging Method, the distance between the lines of gripping force, i.e., the two-cycle hysteresis test gage length, is equal to the starting gage length 133 of the samples before aging (FIG. 4A). The sample is mounted into the grips such that the line of gripping force is centered on the reference lines 132, irrespective of whether the reference lines 132 have remained at the tape/sample interface (FIG. 4B) or have moved during the aging process (FIG. 4C), as described in the Elastomer and Laminate Aging Method. Further, for elastomer samples that sustain any permanent set after the aging and recovery protocol, there may be some slack in the mounted sample. In these cases, the tensile tester crosshead may have to move some distance before a sustainable finite force is observed during the first load cycle. This procedure is intended to simulate the permanent set and resulting force loss that may occur with a full product during storage in its compressed package.

The two cycle hysteresis test method for film samples involves the following steps (all strains are engineering strains):

(1) Strain the sample to 375% at a constant crosshead speed of 20 inches per minute (50.8 cm per minute) with no hold.
(2) Reduce strain to 0% strain (i.e., return grips to original gage length of 2.50 inches) at a constant crosshead speed of 3 inches per minute (7.62 cm per minute) with no hold.
(3) Strain the sample to 375% at a constant crosshead speed of 20 inches per minute (50.8 cm per minute) with no hold.
(4) Reduce strain to 200% strain at a constant crosshead speed of 3 inches per minute (7.62 cm per minute).
(5) Hold at 200% strain for 2 minutes.
(6) Reduce strain to 150% strain at a constant crosshead speed of 3 inches per minute (7.62 cm per minute).
(7) Hold at 150% strain for 2 minutes.
(8) Reduce strain to 100% strain at a constant crosshead speed of 3 inches per minute (7.62 cm per minute).
(9) Hold at 100% strain for 2 minutes.
(10) Reduce strain to 60% strain at a constant crosshead speed of 3 inches per minute (7.62 cm per minute).
(11) Hold at 60% strain for 5 minutes.
(12) G0 to 0% strain at a constant crosshead speed 3 inches per minute (7.62 cm per minute).

The measured unload forces are (i) the force at 200% strain after the 2 minute hold in step 5, (ii) the force at 150% strain after the 2 minute hold in step 7, (iii) the force at 100% strain after the 2 minute hold in step 9, and (iv) the force at 60% strain after the 5 minute hold in step 11. For test samples with a rectangular or square cross section, the unload forces are normalized to Newton's per 20 millimeter width per 100 grams per square meter basis weight as follows: Normalized unload force=[measured unload force×20 mm×100 grams per square meter]÷[initial sample width in mm×initial basis weight in grams per square meter], where the initial width and initial basis weight are determined before the sample is stretched. A minimum of five samples for each material is tested, and the arithmetic average of the normalized unload force at each hold strain is reported.

For test samples with a cross section that is neither rectangular nor square, an equivalent initial sample width $w_e$ and an equivalent initial basis weight $BW_e$ are used to normalize the unload force. The equivalent width $w_e$ is the width of a rectangle with the same area as the sample cross section, while maintaining the aspect ratio of the equivalent rectangle ($=w_e/h_e$) equal to the aspect ratio of a circumscribed rectangle that bounds the sample cross section, where $h_e$ is the equivalent height of the rectangle with $w_e \geq h_e$, and where the circumscribed rectangle is the smallest (by area) rectangle that can be drawn around the sample cross section. For example, if the sample cross section is circular with a diameter D, the area of the equivalent rectangle ($=w_e h_e$) is equal to $\pi D^2/4$, the circumscribed rectangle has an area equal to $D^2$ and an aspect ratio of 1 ($=w_e/h_e$), and the equivalent width is given by $w_e = \pi^{1/2} D/2 = 0.89D$. Further, for example, if the sample cross section is elliptical with a major axis equal to 2a and a minor axis equal to 2b, the area of the equivalent rectangle is equal to $\pi ab$, the circumscribed rectangle has an area equal to 4ab and an aspect ratio of a/b, and the equivalent width is given by $w_e = \pi^{1/2} a = 1.77a$. The corresponding equivalent basis weight is determined from the equivalent width and the measured mass per unit length $m_1$ of the test sample, namely $Bw_e = m_1/w_e$. The measured unload forces are normalized to Newton's per 20 millimeter width per 100 grams per square meter basis weight as follows: Normalized unload force=[measured unload force×20 mm×100 grams per square meter]÷[initial equivalent sample width $w_e$ in mm×initial equivalent basis weight $BW_e$ in grams per square meter], where the equivalent initial width and equivalent initial basis weight are determined before the sample is stretched. A minimum of five samples for each material is tested, and the arithmetic average of the normalized unload force at each hold strain is reported.

For different sample dimensions, the crosshead speed is adjusted to maintain the appropriate strain rate for each portion of the test. For example, a crosshead speed of 10 inches per minute (25.4 cm per minute) would be used in Steps 1 and 3 for a sample gage length of 1.25 inches (31.7 mm). For film samples that can not be strained to 375% without failure, the loading strain used in steps 1 and 3 should be taken as 70% of the arithmetic average strain at break determined from a standard tensile test, such as described in ASTM D 882, using a crosshead speed of 20 inches per minute, a gage length of 2.5 inches, and a sample width of 1 inch. The average strain at break should be determined from a minimum of five samples for each material. Additionally, if any of the hold strains in steps 5, 7, 9, and 11 are above the loading strain in steps 1 and 3, that hold step and the preceding strain reduction step are skipped.

Two Cycle Hysteresis Test for Laminates

This method is used to determine laminate properties that may correlate with the forces experienced by the consumer during application of the product containing a slow recovery stretch laminate and how the product fits and performs once it is applied.

The two cycle hysteresis test method is performed at room temperature (about 22° C.) and also at body temperature (37° C.). The stretch laminate to be tested is cut into a sample of substantially rectilinear dimensions.

Sample dimensions are selected to achieve the required strain with forces appropriate for the instrument. Suitable instruments for this test include tensile testers from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 16 millimeters wide by approximately 75 millimeters long. The sample thickness is dependent on the materials and structure of the stretch laminate and on the confining pressure used to measure the thickness. The thicknesses of samples may be 0.5 millimeters to 5 millimeters thick measured with 0.2 pounds per square inch confining pressure. However, testing of stretch laminates with different thicknesses (e.g., less than 0.5 millimeters or greater than 5 millimeters) is within the scope of this method.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The width of the grips used for the test is greater than or equal to the width of the sample. 1 inch (25.4 millimeter) wide grips may be used. The grips are air actuated grips designed to concentrate the entire gripping force along a single line perpendicular to the direction of testing stress having one flat surface and an opposing face from which protrudes a half round (radius=6 mm) to minimize slippage of the sample.

The load cell is selected so that the forces measured will be between 10% and 90% of the capacity of the load cell or the load range used. A 25 Newton load cell may be used. The fixtures and grips are installed. The instrument is calibrated according to the manufacturer's instructions. The distance between the lines of gripping force (gauge length) is 2.50 inches (63.5 millimeters), which is measured with a steel ruler held beside the grips, unless specified otherwise. The load reading on the instrument is zeroed to account for the mass of the fixture and grips. The specimen is equilibrated a minimum of 1 hour at 22° C. before testing. The specimen is mounted into the grips in a manner such that there is no slack and the load measured is between 0.00 Newton's and 0.02 Newton's, unless specified otherwise. The instrument is located in a temperature-controlled room for measurements performed at 22° C. A suitable environmental chamber is used to maintain the testing temperature for measurements performed at 37° C.; the sample is mounted in the grips and equilibrated for 5 minutes at 37° C. before starting the test.

Stretch laminates from different sources may have different strains above which irreversible deformation, delamination, tearing, or a significant percent set (i.e., set greater than 5%) begins to occur. This is true for stretch laminates obtained from commercially available products such as the side panels, leg cuffs, and waistbands of diapers, and for stretch laminates made internally, for example stretch laminates made according to the Laminate Preparation Method disclosed in the Examples. For the purposes of the Two Cycle Hysteresis Test for Laminate Samples, the peak test strain (% $Strain_{peak}$) is taken as 70% of the average maximum percent strain determined according to the Maximum Laminate Strain Test rounded up to the nearest multiple of five if the value does not result in a target strain that is divisible by five when rounded to the nearest percent. For example, if 70% of the average maximum percent strain is equal to 187.1%, this value is not divisible by 5 when rounded to the nearest percent (187%), so the peak strain would be taken as 190%. Also, for example, if 70% of the average maximum percent strain is equal to 180.1%, this value is divisible by 5 when rounded to the nearest percent (180%), so the peak strain would be taken as 180%. For laminates with an average maximum percent strain of greater than 536%, a peak strain of 375% is used.

For laminates that have been aged according to the Elastomer and Laminate Aging Method, the peak strain is determined from a set of equivalent laminate samples that have not been aged according to the Elastomer and Laminate Aging Method. For example, laminates produced according to the Laminate Preparation Method in Example 3, line made stretch laminates, or those obtained from commercially available products that have not been subjected to any additional aging beyond the history they undergo in production and in typical storage and transportation conditions (e.g., strain, pressure, temperature). The intention is to make a comparison in the hysteresis curves before and after the aging process, so care should be taken not to subject the starting laminate samples to any further aging unless specifically performing the Elastomer and Laminate Aging Method.

Additionally, for laminate samples that have been aged according to the Elastomer and Laminate Aging Method, the distance between the lines of gripping force, i.e., the two-cycle hysteresis test gage length, is equal to the starting gage length 133 of the samples before aging (FIG. 4A). The laminate is mounted into the grips such that the line of gripping force is centered on the reference lines 132, irrespective of whether the reference lines 132 have remained at the tape/sample interface (FIG. 4B) or have moved during the aging process (FIG. 4C), as described in the Elastomer and Laminate Aging Method. Further, for laminate samples that sustain any permanent set after the aging and recovery protocol, there may be some slack in the mounted sample. In these cases, the tensile tester crosshead may have to move some distance before a sustainable finite force is observed during the first load cycle. This procedure is intended to simulate the permanent set and resulting force loss that may occur with a full product during storage in its compressed package.

The two cycle hysteresis test method for laminate samples involves the following steps (all strains are engineering strains):

(1) Strain the sample to the specified peak percent strain (% $Strain_{peak}$) at a constant crosshead speed of 20 inches per) minute (50.8 centimeters per minute) with no hold.

(2) Reduce the strain to 0% strain (i.e., return grips to the original gage length of 2.50 inches) at a constant crosshead speed of 3 inches per minute (7.62 centimeters per minute) with no hold.
(3) Strain the sample to % $Strain_{peak}$ at a constant crosshead speed of 20 inches per minute (50.8 centimeters per minute) with no hold.
(4) Reduce the strain at a constant crosshead speed of 3 inches per minute (7.62 centimeters per minute) to the first hold strain listed in Table 1 for the specified % $Strain_{peak}$.
(5) Hold the sample at the strain in step (4) for the first hold time listed in Table 1 for the specified % $Strain_{peak}$.
(6) Reduce the strain at a constant crosshead speed of 3 inches per minute (7.62 centimeters per minute) to the second hold strain listed in Table 1 for the specified % $Strain_{peak}$.
(7) Hold the sample at the strain in step (6) for the second hold time listed in Table 1 for the specified % $Strain_{peak}$.
(8) Reduce the strain at a constant crosshead speed of 3 inches per minute (7.62 centimeters per minute) to the third hold strain listed in Table 1 for the specified % $Strain_{peak}$.
(9) Hold the sample at the strain in step (8) for the third hold time listed in Table 1 for the specified % $Strain_{peak}$.
(10) Reduce the strain at a constant crosshead speed of 3 inches per minute (7.62 centimeters per minute) to the fourth hold strain listed in Table 1 for the specified % $Strain_{peak}$.
(11) Hold the sample at the strain in step (10) for the fourth hold time listed in Table 1 for the specified % $Strain_{peak}$.
(12) G0 to 0% strain at a constant crosshead speed of 3 inches per minute (7.62 centimeters per minute).

For laminates in which the test % $Strain_{peak}$ is greater than or equal to 60%, and where one of the hold strains in steps (5), (7), (9), or (11) is equal to 60%, the reported unload force is the measured unload force of the stretch laminate (SL) at 60% after the hold period, normalized to Newton's per meter width of SL per grams per square meter basis weight of elastomer plus adhesive (E+A) in the SL, N/(m·gsm)=N/(g/m), as shown in the equation below. The basis weight of the elastic and adhesive in the SL is calculated by dividing the grams of elastomer plus adhesive in the SL by the area of the SL fully extended. The area of the fully extended stretch laminate ($A_{FESL}$) is defined as the area of the substrate of the stretch laminate in the absence of elastic and adhesive. The normalized unload force in $$N/(m \cdot gsm) = N/(g/m) = \frac{\text{measured unload force in Newtons}}{\{[\text{width of } SL \text{ in meters}] \times [(\text{grams of } E + A) \div (A_{FESL} \text{ in square meters})]\}}$$

A minimum of five samples for each material is tested, and the arithmetic average of the normalized unload force at 60% strain is reported.

For laminates in which the test % $Strain_{peak}$ is greater than or equal to 60%, and where none of the hold strains in steps (5), (7), (9), or (11) is equal to 60%, the reported unload force is the interpolated unload force of the stretch laminate at 60% strain obtained by interpolating linearly between the unload forces at adjacent strains and then normalizing according to the equation above. For example, if % $Strain_{peak}$=180%, then according to Table 1, the hold strains for steps (5), (7), (9), and (11) are 100%, 75%, 50%, and 30%, respectively, and the unload force at 60% would be determined by interpolating linearly between the unload forces obtained in steps (7) and (9) after the hold period, using for example the following relationship:

$$UL_{60} = UL_{60+} - (UL_{60+} - UL_{60-})\left[\frac{HS_{60+} - 60\%}{HS_{60+} - HS_{60-}}\right]$$

Where $UL_{60}$ is the unload force at 60% strain after the hold period, $UL_{60+}$, and $UL_{60-}$ are the unload forces at hold strains just above and just below 60% strain after the hold period, respectively, and $HS_{60+}$, and $HS_{60-}$, are the hold strains just above and just below 60% strain, respectively. Therefore, for the example above, if the unload force in step (7) at 75% strain after the hold is 1.04 Newton's and the unload force in step (9) at 50% strain after the hold is 0.78 Newton's, the interpolated unload force at 60% strain after the hold period is 0.88 Newton's:

$$UL_{60} = 1.04 \text{ N} - (1.04 \text{ N} - 0.78 \text{ N})\left[\frac{75\% - 60\%}{75\% - 50\%}\right] = 0.88 \text{ N}$$

The interpolated unload force is then normalized according to the equation above. A minimum of five samples for each material is tested, and the arithmetic average of the normalized interpolated unload force at 60% strain is reported.

For laminates in which the test % $Strain_{peak}$ is less than 60%, the reported unload force is the measured unload force of the stretch laminate in step (5) after the hold period, normalized according to the equation above. A minimum of five samples for each material is tested, and the arithmetic average of the normalized unload force from step (5) after the hold period is reported.

For different sample dimensions, the crosshead speed is adjusted to maintain the appropriate strain rate for each portion of the test. For example, for a sample gauge length of 1.25 inches (31.7 millimeters), a crosshead speed of 10 inches per minute (25.4 centimeters per minute) would be used in Steps 1 and 3, and a crosshead speed of 1.5 inches per minute (3.81 centimeters per minute) would be used in Steps 4, 6, 8, 10 and 12.

TABLE 1

Hold Strains and Times for Two Cycle Hysteresis Test for Laminate Samples

| Peak Percent Strain | First Hold Percent Strain (Steps 4 and 5) | First Hold Time (Minutes) (Step 5) | Second Hold Percent Strain (Steps 6 and 7) | Second Hold Time (Minutes) (Step 7) | Third Hold Percent Strain (Steps 8 and 9) | Third Hold Time (Minutes) (Step 9) | Fourth Hold Percent Strain (Steps 10 and 11) | Fourth Hold Time (Minutes) (Step 11) |
|---|---|---|---|---|---|---|---|---|
| 375% | 200% | 2.0 | 150% | 2.0 | 100% | 2.0 | 60% | 5.0 |
| 370% | 200% | 2.0 | 150% | 2.0 | 100% | 2.0 | 60% | 5.0 |
| 365% | 195% | 2.0 | 150% | 2.0 | 100% | 2.0 | 60% | 5.0 |
| 360% | 195% | 2.0 | 145% | 2.0 | 100% | 2.0 | 60% | 5.0 |
| 355% | 190% | 2.0 | 145% | 2.0 | 95% | 2.0 | 60% | 5.0 |

TABLE 1-continued

Hold Strains and Times for Two Cycle Hysteresis Test for Laminate Samples

| Peak Percent Strain | First Hold Percent Strain (Steps 4 and 5) | First Hold Time (Minutes) (Step 5) | Second Hold Percent Strain (Steps 6 and 7) | Second Hold Time (Minutes) (Step 7) | Third Hold Percent Strain (Steps 8 and 9) | Third Hold Time (Minutes) (Step 9) | Fourth Hold Percent Strain (Steps 10 and 11) | Fourth Hold Time (Minutes) (Step 11) |
|---|---|---|---|---|---|---|---|---|
| 350% | 190% | 2.0 | 140% | 2.0 | 95% | 2.0 | 60% | 5.0 |
| 345% | 185% | 2.0 | 140% | 2.0 | 95% | 2.0 | 60% | 5.0 |
| 340% | 185% | 2.0 | 140% | 2.0 | 95% | 2.0 | 55% | 5.0 |
| 335% | 180% | 2.0 | 135% | 2.0 | 90% | 2.0 | 55% | 5.0 |
| 330% | 180% | 2.0 | 135% | 2.0 | 90% | 2.0 | 55% | 5.0 |
| 325% | 175% | 2.0 | 130% | 2.0 | 90% | 2.0 | 55% | 5.0 |
| 320% | 175% | 2.0 | 130% | 2.0 | 90% | 2.0 | 55% | 5.0 |
| 315% | 170% | 2.0 | 130% | 2.0 | 85% | 2.0 | 55% | 5.0 |
| 310% | 170% | 2.0 | 125% | 2.0 | 85% | 2.0 | 50% | 5.0 |
| 305% | 165% | 2.0 | 125% | 2.0 | 85% | 2.0 | 50% | 5.0 |
| 300% | 160% | 2.0 | 120% | 2.0 | 80% | 2.0 | 50% | 5.0 |
| 295% | 160% | 2.0 | 120% | 2.0 | 80% | 2.0 | 50% | 5.0 |
| 290% | 155% | 2.0 | 120% | 2.0 | 80% | 2.0 | 50% | 5.0 |
| 285% | 155% | 2.0 | 115% | 2.0 | 80% | 2.0 | 50% | 5.0 |
| 280% | 150% | 2.0 | 115% | 2.0 | 75% | 2.0 | 45% | 5.0 |
| 275% | 150% | 2.0 | 110% | 2.0 | 75% | 2.0 | 45% | 5.0 |
| 270% | 145% | 2.0 | 110% | 2.0 | 75% | 2.0 | 45% | 5.0 |
| 265% | 145% | 2.0 | 110% | 2.0 | 75% | 2.0 | 45% | 5.0 |
| 260% | 140% | 2.0 | 105% | 2.0 | 70% | 2.0 | 45% | 5.0 |
| 255% | 140% | 2.0 | 105% | 2.0 | 70% | 2.0 | 45% | 5.0 |
| 250% | 135% | 2.0 | 100% | 2.0 | 70% | 2.0 | 40% | 5.0 |
| 245% | 135% | 2.0 | 100% | 2.0 | 70% | 2.0 | 40% | 5.0 |
| 240% | 130% | 2.0 | 100% | 2.0 | 65% | 2.0 | 40% | 5.0 |
| 235% | 130% | 2.0 | 95% | 2.0 | 65% | 2.0 | 40% | 5.0 |
| 230% | 125% | 2.0 | 95% | 2.0 | 65% | 2.0 | 40% | 5.0 |
| 225% | 120% | 2.0 | 90% | 2.0 | 60% | 2.0 | 40% | 5.0 |
| 220% | 120% | 2.0 | 90% | 2.0 | 60% | 2.0 | 40% | 5.0 |
| 215% | 115% | 2.0 | 90% | 2.0 | 60% | 2.0 | 35% | 5.0 |
| 210% | 115% | 2.0 | 85% | 2.0 | 60% | 2.0 | 35% | 5.0 |
| 205% | 110% | 2.0 | 85% | 2.0 | 55% | 2.0 | 35% | 5.0 |
| 200% | 110% | 2.0 | 80% | 2.0 | 55% | 2.0 | 35% | 5.0 |
| 195% | 105% | 2.0 | 80% | 2.0 | 55% | 2.0 | 35% | 5.0 |
| 190% | 105% | 2.0 | 80% | 2.0 | 55% | 2.0 | 35% | 5.0 |
| 185% | 100% | 2.0 | 75% | 2.0 | 50% | 2.0 | 30% | 5.0 |
| 180% | 100% | 2.0 | 75% | 2.0 | 50% | 2.0 | 30% | 5.0 |
| 175% | 95% | 2.0 | 70% | 2.0 | 50% | 2.0 | 30% | 5.0 |
| 170% | 95% | 2.0 | 70% | 2.0 | 50% | 2.0 | 30% | 5.0 |
| 165% | 90% | 2.0 | 70% | 2.0 | 45% | 5.0 | 30% | 5.0 |
| 160% | 90% | 2.0 | 65% | 2.0 | 45% | 5.0 | 30% | 5.0 |
| 155% | 85% | 2.0 | 65% | 2.0 | 45% | 5.0 | 25% | 5.0 |
| 150% | 80% | 2.0 | 60% | 2.0 | 40% | 5.0 | 25% | 5.0 |
| 145% | 80% | 2.0 | 60% | 2.0 | 40% | 5.0 | 25% | 5.0 |
| 140% | 75% | 2.0 | 60% | 2.0 | 40% | 5.0 | 25% | 5.0 |
| 135% | 75% | 2.0 | 55% | 2.0 | 40% | 5.0 | 25% | 5.0 |
| 130% | 70% | 2.0 | 55% | 2.0 | 35% | 5.0 | 25% | 5.0 |
| 125% | 70% | 2.0 | 50% | 2.0 | 35% | 5.0 | 20% | 5.0 |
| 120% | 65% | 2.0 | 50% | 2.0 | 35% | 5.0 | 20% | 5.0 |
| 115% | 65% | 2.0 | 50% | 2.0 | 35% | 5.0 | 20% | 5.0 |
| 110% | 60% | 2.0 | 45% | 5.0 | 30% | 5.0 | 20% | 5.0 |
| 105% | 60% | 2.0 | 45% | 5.0 | 30% | 5.0 | 20% | 5.0 |
| 100% | 60% | 2.0 | 45% | 5.0 | 30% | 5.0 | 20% | 5.0 |
| 95% | 60% | 2.0 | 45% | 5.0 | 30% | 5.0 | 20% | 5.0 |
| 90% | 60% | 2.0 | 45% | 5.0 | 30% | 5.0 | 20% | 5.0 |
| 85% | 60% | 2.0 | 45% | 5.0 | 30% | 5.0 | 20% | 5.0 |
| 80% | 60% | 2.0 | 45% | 5.0 | 30% | 5.0 | 20% | 5.0 |
| 75% | 60% | 2.0 | 45% | 5.0 | 30% | 5.0 | 20% | 5.0 |
| 70% | 60% | 2.0 | 45% | 5.0 | 30% | 5.0 | 20% | 5.0 |
| 65% | 60% | 2.0 | 45% | 5.0 | 30% | 5.0 | 20% | 5.0 |
| 60% | 60% | 2.0 | 45% | 5.0 | 30% | 5.0 | 20% | 5.0 |
| 55% | 55% | 2.0 | 45% | 5.0 | 30% | 5.0 | 15% | 5.0 |
| 50% | 50% | 2.0 | 40% | 5.0 | 25% | 5.0 | 15% | 5.0 |
| 45% | 45% | 5.0 | 35% | 5.0 | 25% | 5.0 | 10% | 5.0 |
| 40% | 40% | 5.0 | 30% | 5.0 | 20% | 5.0 | 10% | 5.0 |
| 35% | 35% | 5.0 | 30% | 5.0 | 20% | 5.0 | 10% | 5.0 |
| 30% | 30% | 5.0 | 25% | 5.0 | 15% | 5.0 | 5% | 5.0 |
| 25% | 25% | 5.0 | 20% | 5.0 | 15% | 5.0 | 5% | 5.0 |
| 20% | 20% | 5.0 | 15% | 5.0 | 10% | 5.0 | 5% | 5.0 |
| 15% | 15% | 5.0 | 10% | 5.0 | 5% | 5.0 | Skip | Skip |
| 10% | 10% | 5.0 | 5% | 5.0 | Skip | Skip | Skip | Skip |
| 5% | 5% | 5.0 | Skip | Skip | Skip | Skip | Skip | Skip |

Oil Exposure Method

This method is used to determine the effect of exposing a slow recovery stretch laminate comprising an elastic member or a slow recovery elastomer to an excess of mineral oil and separately to an excess of isopropyl palmitate, a common ingredient in many baby oils, lotions, gels, cremes, and the like. A small sample (~0.1 grams) of either a stretch laminate or an elastic member is placed in each of two clean vials. To one vial is added about 10 ml of mineral oil (Britol® SOT available from Crompton Corporation, Petrolia, Pa.), and to a second vial is added about 10 ml of isopropyl palmitate (90+% grade available from Sigma-Aldrich, St. Louis, Mo.). It may be necessary to gently mix the contents in order to completely wet or submerge the sample into the mineral oil or isopropyl palmitate. The mixtures are allowed to sit for 30 hours at room temperature (22° C.). After 30 hours, a visual observation is made of each sample, and if any sample appears to remain intact, it is removed from the vial and its ability to be extended is approximated by hand, e.g., when clamped between the thumb and forefinger on each hand and then pulled apart. If the samples remain intact after 30 hours in both mineral oil and isopropyl palmitate, and if the samples after the 30 hours maintain an extension of greater than about 50% engineering strain from both mineral oil and isopropyl palmitate, then the laminate or elastomer samples are considered to have passed the Oil Exposure Method. Other mineral oils are within the scope of this method including commercial baby oils that list mineral oil as the primary ingredient, e.g., Johnson's Baby Oil which is available in the U.S. from Johnson & Johnson, New Brunswick, N.J.

EXAMPLES

Example 1

Slow recovery stretch films are prepared using varying amounts of elastomeric polymer, modifying resin, and mineral oil as shown in Table 2. The blending is accomplished either by extrusion of the blend (Sample Films F1a, F1b, and F2) or by small batch melt mixing and compression molding into a film on a heated Carver Press (Sample Films F3-F6). Sample Films F1a and F1b comprise a nonhydrogenated styrene-isoprene-styrene (SIS) triblock copolymer, commercially available under the trade designation Vector® 4211 from Dexco Polymers L.P., Houston, Tex. Sample Films F2 and F3 comprise an hydrogenated styrene-ethylene-ethylene/propylene-styrene (SEEPS) triblock copolymer, commercially available under the trade designation Septon™ 4033 from Kuraray America Inc., Pasedena, Tex. Sample Films F4-F6 comprise a combination of SEEPS triblock copolymers, commercially available under the trade designations Septon™ 4033 and Septon™ 4044, both from Kuraray America Inc., Pasedena, Tex., and where Septon™ 4044 is a higher molecular weight version of Septon™ 4033. Sample Films F1a and F1b include a modifying resin in the form of an alicyclic hydrocarbon resin under the trade designation Arkon P140, available from Arakawa Chemical Inc., Chicago, Ill. Sample Films F2-F6 include a modifying resin in the form of an hydrogenated aliphatic hydrocarbon resin under the trade designation Eastotac™ H-142R, available from Eastman Chemical Company, Kingsport, Tenn. Sample Films F1-F6 include white mineral oil, commercially available under the trade designation Britol® SOT from Crompton Corporation, Petrolia, Pa. Sample Films F2-F6 represent elastomer films of the present disclosure while Sample Films F1a and F1b represent comparative elastomer films.

TABLE 2

Slow Recovery Elastomer Compositions (weight percent)

| | Sample Film Number** | | | | | | |
|---|---|---|---|---|---|---|---|
| | F1a | F1b | F2 | F3 | F4 | F5 | F6 |
| Film Component* | | | | | | | |
| Vector 4211 (SIS, 29 wt % styrene) | 48.5% | 48.5% | | | | | |
| Septon 4033 (SEEPS, 30 wt % styrene) | | | 44.6% | 44.6% | 39.0% | 33.5% | 22.3% |
| Septon 4044 (SEEPS, 32 wt % styrene) | | | | | 5.6% | 11.2% | 22.3% |
| Arkon P140 | 48.5% | 48.5% | | | | | |
| Eastotac H-142R | | | 53.5% | 53.5% | 53.5% | 53.5% | 53.5% |
| Mineral Oil (White Britol 50T) | 3.0% | 3.0% | 1.9% | 1.9% | 1.9% | 1.9% | 1.9% |
| Film Property | | | | | | | |
| Film type (E = extruded, CM = compression molded) | E | E | E | CM | CM | CM | CM |
| Arithmetic average film basis weight (grams per square meter) | 131 | 140 | 88 | 157 | 151 | 173 | 167 |

*Weight percent styrene are nominal values based on manufacturer's technical data sheet. Component percentages are weight percent.
**Samples F1a and F1b are comparative examples, Samples F2-F6 are embodiments of the present invention.

Extruded films are prepared using a high torque co-rotating twin-screw extruder manufactured by Berstorff (a division of KraussMaffei Corporation, Florence, Ky.) under the name ZE25. This extruder has 25 millimeter screw diameters, a length-to-diameter ratio of 32, and six heating/cooling barrel zones along its length in addition to a cooled feeding zone. A dry blend of the elastomer, oil, and modifying resin is tumbled to achieve a relatively uniform mixture, and the dry blend is fed to the extruder via a vibratory gravity feeder. The first heating/cooling zone (barrel zone 2) is maintained at a sufficiently high temperature to initiate softening of the elastomer and modifying resin, and consists of conveying elements for transporting the materials forward. The second through fourth heating/cooling zones (barrel zones 3-5) are each equipped with a high shearing forward kneading element and forward conveying elements, while the fourth heating/cooling zone (barrel zone 5) is also equipped with a high shearing backward kneading element and the fifth heating/cooling zone (barrel zone 6) is equipped with a dispersion element and a reverse conveying seal element, all to facilitate increased pressure, shearing, and mixing of the low and high molecular weight components. The sixth and last heating/cooling zone (barrel zone 7) is equipped with forward conveying elements intended to build sufficient pressure behind a cast film die, and to facilitate extrusion through the die. For Sample Films F1a and F1b, the set temperature profile (barrel zones 2-7, transfer tube, die) is about 280° F., 315° F., 345° F., 365° F., 365° F., 360° F., 325° F., 325° F., with the screws being rotated at about 60 revolutions per minute. For Sample Film F2, the set temperature profile (barrel zones 2-7, transfer tube, die) is about 200° F., 275° F., 300° F., 315° F., 325° F., 325° F., 340° F., 340° F., with the screws being rotated at about 50 revolutions per minute. A 10 inch wide coat hanger cast film die is used to shape the compounded elastomer mixture into a thin film, and a film take-off unit is positioned to receive the extrudate which is collected on double sided silicone coated release paper and wound onto a cardboard roll. The film basis weight is adjusted by varying the linear speed of the take-off unit, and the film is stored at room temperature (about 22° C.) for at least 2 days before evaluating the properties of the film or before making laminates from the films. The width of the collected film from the 10 inch cast film die is about 7.5 inches, and the middle 5 inches is used for property testing or for laminate making. Additionally, for any given property test or laminate preparation, a minimum of five samples are cut and tested from the collected film, and the spacing in the machine direction of manufacture is about 80 inches between each cut and tested film sample. This spacing is intended to yield a representative sampling of the collected film.

Small batch melt mixed films are prepared using a Haake Rheomix 600 internal mixer fitted with double blades (Thermo Scientific, Newington, N.H.), and a compression molding press with 9 inch by 9 inch heated platens (Carver, Inc., Wabash, Ind., Model numbers 3853-0/3925). The metal temperatures of the mixer are set to about 185° C. (about 365° F.) for Sample Films F3 and F5, about 195° C. (about 383° F.) for Sample Film F4, and about 220° C. (about 428° F.) for Sample Film F6. After the metal temperatures are equilibrated, the blades are started rotating at about 25 revolutions per minute, and about 50 grams of a dry blend of the elastomer, oil, and modifying resin is added to the internal mixer, and the loading chute is closed. The rotation speed of the blades is then ramped up to about 85 revolutions per minute in intervals of about 10 revolutions per minute, allowing about 5 seconds of speed equilibration at each step before moving to the next higher speed. After about 5 minutes of mixing at 85 revolutions per minute, the loading chute is opened to check the uniformity of the mix. If the sample does not appear to be fully blended, the mixing temperature, time, and/or rotation speed is increased, taking care not to overheat the sample (generally denoted by a discoloration or tanning of the sample). Otherwise, the rotation speed is reduced to about 40 revolutions per minute and the metal set temperatures to about 120° C. After about 5 minutes, the rotation speed is further reduced to about 20 revolutions per minute. After an additional 5 minutes, the rotation of the blades is stopped, and the blend is removed from the internal mixer and allowed to cool to room temperature (about 22° C.).

The compression molding press is used along with a custom mold to prepare film samples from the melt mixed compositions. The mold is an assembly of two metal plates (about 9 inches wide and about 12 inches long), two sheets of Teflon® film (about 6 inches wide, about 12 inches long, and about 0.010 inches thick), and two metal shims (about 1 inch wide, about 12 inches long, and about 0.027 inches thick). The assembly forms a mold about 0.007 inches deep. The metal platens on the compression molding press are set to a temperature based on the order-disorder temperature of the melt mixed composition, and the metal plates are preheated by stacking them onto the lower platen. After the temperature of the platens and metal plates has reached the set temperature, about 3 grams of the melt mixed composition is placed on one of the Teflon® sheets, which is then placed on top of one of the preheated metal plates. The shims are placed on the outer edges of the metal plate, outside of the Teflon® sheets. The second Teflon® sheet and second preheated metal plate are then placed on top to finish assembly of the mold. The entire mold assembly is placed in the compression molding press and maintained at the set temperature with about 2500 pounds per square inch of pressure on the mold. After about 30 seconds, the pressure applied to the mold is increased to about 10,000 pounds per square inch and held for about 30 seconds. The pressed film, maintained between the Teflon® sheets, is removed from the mold and cooled to room temperature (about 22° C.). The film is removed from between the Teflon® sheets, folded and repressed according to the procedure outlined above with the exception that when the 10,000 pounds per square inch is applied to the mold, it is held for about 60 seconds instead of about 30 seconds. The film is removed from the mold after the second press, maintained between the Teflon® sheets, and cooled to room temperature (about 22° C.). The film is removed from between the Teflon® sheets, and stored at room temperature between double sided release paper for about 2 days before evaluating the properties of the film. For any given property test, a minimum of five random samples are cut and tested from at least two different compression molded films, and the number of test samples are split relatively evenly between the number of compression molded films. For example, if two compression molded film samples are produced, 3 random test samples are taken from one molded film and 2 random test samples are taken from the other molded film.

Compression molded samples for order-disorder temperature (ODT) analysis are produced following the procedure outlined above, with the following exceptions: (i) shims of about 1.5 millimeters thick are used on all four sides of the mold, (ii) the step where about 2500 pounds per square inch pressure is applied to the mold is skipped, and (iii) when about 10,000 pounds per square inch of pressure is applied to the mold, it is held for about 3 minutes at this pressure. When the film is removed from between the Teflon® sheets, it is inspected for air bubbles. If there are no observable bubbles within at least a 27 millimeter diameter area, the film is suitable for determining the ODT. If there is no area of about 27 millimeters in diameter without observable bubbles, the sample is folded and repressed. This procedure is repeated until an area of at least 27 millimeters is observed without bubbles, taking care not to repeat this procedure too many times with a given sample (generally denoted by the sample becoming discolored or slightly tanned in color). If necessary, the pressing procedure is followed with a new piece of the melt mixed composition. Additionally, if the elastomer film is extruded, it may be possible to stack multiple film samples to produce a sample for ODT analysis. In this case, it is recommended that the stack be further compressed in a compression molding press at room temperature and to make sure there is virtually no trapped air between any of the film layers.

Films of the elastomer compositions F1a and F2-F6 in Table 2 are measured according to the Order-Disorder Temperature and Post Elongation Recovery methods described in the Test Methods section above. The order-disorder temperature (ODT) and the percent of initial strain after 15 seconds recovery at 22° C. (72° F.) and 37° C. (99° F.) are shown in Table 3. Additionally, films of the elastomer compositions F1a and F2-F6 in Table 2 are aged according to the Elastomer and Laminate Aging method described in the Test Methods section above. The corresponding non-aged control films of elastomer compositions F1a and F2-F6 in Table 2 are pre-strained to 300% engineering strain and allowed to recover according to the Elastomer and Laminate Aging method described in the Test Methods section above. The unload forces of the aged and non-aged elastomer films are measured according to the Two-Cycle Hysteresis Test For Elastomers method described in the Test Methods section above. The normalized unload force at 37° C. (99° F.) and hold strains of 60%, 100%, 150%, and 200% engineering strain are shown in Table 3 along with the corresponding force retention factor at each hold strain. Table 3 shows the advantage of a slow recovery elastomer composition comprising an hydrogenated elastomer, and the advantage of a higher ODT within a given chemical family comprising an hydrogenated elastomer.

TABLE 4

Elastomer Compositions (weight percent) and Order-Disorder Temperature

| | Sample Film Number | | |
|---|---|---|---|
| | F3 | F7 | F8 |
| Film Component* | | | |
| Septon 4033 (SEEPS, 30 wt % styrene) | 44.6% | 37.0% | 29.4% |
| Eastotac H-142R | 53.5% | 44.4% | 35.3% |
| Mineral Oil (White Britol 50T) | 1.9% | 1.6% | 1.3% |
| H2861 adhesive | | 17.0% | 34.0% |
| Film Property | | | |
| Order-Disorder Temperature | 157° C. | 144° C. | 139° C. |

*Weight percent styrene are nominal values based on manufacturer's technical data sheet. Component percentages are weight percent.

TABLE 3

Elastomer Order-Disorder Temperature and Aging

| Film Property | Film Aged?* | Sample Film Number | | | | | |
|---|---|---|---|---|---|---|---|
| | | F1a | F2 | F3 | F4 | F5 | F6 |
| Order-Disorder Temperature (ODT) | No | 156° C. | 151° C. | 157° C. | 180° C. | 200° C. | 223° C. |
| Percent of initial strain after 15 seconds recovery at 22° C. (72° F.) | No | 34.9% | 52.9% | 39.5% | 45.7% | 44.3% | 42.3% |
| Percent of initial strain after 15 seconds recovery at 37° C. (99° F.) | No | 11.6% | 8.4% | 3.0% | 3.4% | 3.0% | 4.0% |
| Normalized unload force at 37° C. (99° F.) and 200% hold strain (Newtons) | No | 0.51 | 1.28 | 1.16 | 1.10 | 1.06 | 0.81 |
| | Yes | 0.20 | 0.92 | 1.00 | 0.96 | 0.96 | 0.76 |
| Force Retention Factor** | | 1.65 | 3.56 | 7.25 | 7.86 | 10.6 | 16.2 |
| Normalized unload force at 37° C. (99° F.) and 150% hold strain (Newtons) | No | 0.41 | 1.06 | 0.98 | 0.93 | 0.89 | 0.68 |
| | Yes | 0.14 | 0.75 | 0.83 | 0.80 | 0.81 | 0.63 |
| Force Retention Factor** | | 1.52 | 3.42 | 6.53 | 7.15 | 11.1 | 13.6 |
| Normalized unload force at 37° C. (99° F.) and 100% hold strain (Newtons) | No | 0.31 | 0.84 | 0.79 | 0.75 | 0.72 | 0.54 |
| | Yes | 0.05 | 0.54 | 0.63 | 0.61 | 0.63 | 0.48 |
| Force Retention Factor** | | 1.19 | 2.80 | 4.94 | 5.36 | 8.00 | 9.00 |
| Normalized unload force at 37° C. (99° F.) and 60% hold strain (Newtons) | No | 0.22 | 0.64 | 0.59 | 0.56 | 0.53 | 0.39 |
| | Yes | 0.01 | 0.31 | 0.40 | 0.39 | 0.42 | 0.32 |
| Force Retention Factor** | | 1.05 | 1.94 | 3.11 | 3.29 | 4.82 | 5.57 |

*Film aged according to Elastomer and Laminate Aging Method - 1 week at 40° C. and 100% engineering strain; films not aged for Two Cycle Hysteresis Test are prestrained to 300% engineering strain then allowed to recover according to the procedure outlined in the Elastomer and Laminate Aging Method.
**Force Retention Factor = (Non Aged Film Force)/(Non Aged Film Force – Aged Film Force)

Example 2

Compression molded films of elastomer compositions F7 and F8 listed in Table 4 are prepared according to the film preparation methods described in Example 1, where the metal temperatures of the mixer are set to about 195° C. and where H2861 is an adhesive commercially available from Bostik, Inc., Wauwatusa, Wis. The weight ratio of added elastomer (Septon 4033) to modifying resin (Eastotac H-142R) to mineral oil (White Britol 50T) in elastomer film samples F7 and F8 is equivalent to the control elastomer film F3 from Table 2. Films of the elastomer compositions in Table 4 are measured according to the Order-Disorder Temperature method described in the Test Methods section above. The order-disorder temperatures (ODT) are shown in Table 4, and illustrate the effect an adhesive composition can have on the ODT of an elastomer composition of the present disclosure.

Example 3

Slow recovery stretch laminates are prepared with the extruded films disclosed in Table 2 (Sample Films F1b and F2). Elastomeric film samples are cut to be approximately 40 millimeters wide by approximately 117 millimeters long for Sample Film F1b or approximately 40 millimeters wide by approximately 147 millimeters long for Sample Film F2. The mass of each elastomeric film is measured to the nearest 0.1 milligram. The basis weight (grams per square meter, "gsm") of each film is calculated by dividing the film weight (in grams) by the film area (length by width in square meters). The slow recovery stretch laminates in Table 5 are adhesively bonded multilayer laminate structures comprising two nonwovens sandwiching the elastomeric film. The nonwoven, available from First Quality Nonwovens (Great Neck, N.Y.), is a spunbond-meltblown-spunbond polypropylene thermally bonded nonwoven having a basis weight of about 22 gsm. One of the nonwovens is bonded to the first surface of the elastomeric film using a single layer of adhesive applied in a spiral pattern in an amount of about 18.6 gsm. The second nonwoven is bonded to the second surface of the elastomeric film using a single layer of adhesive applied in a spiral pattern in an amount of about 18.6 gsm. A suitable adhesive is H2861 available from Bostik, Inc. (Wauwatusa, Wis.).

The stretch laminate preparation, stretching Sample Film F1b to 450% engineering strain or Sample Film F2 to 280% engineering strain, involves the following steps:

(1) Measure the width, length and weight of the elastomer film to be used in the stretch laminate. Attach double-sided tape (about 40 millimeters wide by about 1 inch long) to each end of the film so that the length of film between the tapes is about 66.5 millimeters for Sample Film F1b or about 96.3 millimeters for Sample Film F2.

(2) Place a nonwoven sample (about 2 inches wide by 455 millimeters long) on a board and tape each end down to hold the laminate flat onto the board. The length of the nonwoven between the tapes is about 415 millimeters long.

(3) Place a glue strip (i.e., 18.6 gsm of the adhesive applied in a spiral pattern to one face of a 40 millimeter wide by 445 millimeter long sheet of release paper) centered on top of the nonwoven and with the glue side to the nonwoven. Apply pressure to bond the adhesive to the nonwoven using a 4.5 pound roller (ChemInstruments, Fairfield, Ohio, model HR-100) with 4 full strokes, where a stroke is a single pass from edge-to-edge on the nonwoven. Remove the release paper.

(4) Using the double-sided tape, attach one end of the elastomeric film (40 millimeters wide non-stretched by 66.5 millimeters long between tapes for Sample Film F1b or 40 millimeters wide non-stretched by 96.3 millimeters long between tapes for Sample Film F2) to one end of the glue/nonwoven assembly. Stretch the free end of the elastomeric film to a length of 366 millimeters, and place it centered on top of the glue/nonwoven assembly. In this way, the slow recovery elastic is stretched to about 450% engineering strain for Sample Film F1b (66.5 millimeters to 366 millimeters) or to about 280% engineering strain for Sample Film F2 (96.3 millimeters to 366 millimeters).

(5) Place a glue strip, similar to the one described in step (3), centered on top of the stretched elastomeric film and with the glue side to the elastomeric film. Apply pressure to bond (HR-100, 4 full strokes) and remove the release paper.

(6) Place the second nonwoven (2 inches wide by 455 millimeters long between tapes) centered on top of the laminate. Apply pressure with the roller (HR-100, 20 full strokes) to bond the laminate.

(7) Trim away the sides of the laminate and retain about the middle 16 millimeters, making sure that the elastomeric film extends fully across the 16 millimeter width for the total length of the laminate. The area of the fully extended slow recovery stretch laminate ($A_{FESL}$) is then about 0.00586 square meters (366 millimeters long by 16 millimeters wide between tapes), and the two strips of glue spirals used in steps 3 and 5 add approximately 0.22 grams of adhesive to the stretch laminate (18.6 grams per square meter adhesive per side×2 sides×0.00586 square meters). For film samples that are narrower than 16 millimeters after stretching the elastomeric film to 366 millimeters in step (4), reduce the width of the trimmed laminate accordingly and calculate the corresponding extended area $A_{FESL}$ and adhesive add-on level.

(8) Remove the laminate structure from the board and allow to recover for 10 minutes at room temperature (about 22° C.) hanging vertically, followed by another 10 minutes of recovery at about 40° C. laying flat on release paper. Measure the length of the gathered laminate between the tapes without stretching. The samples are then allowed to fully recover by placing them in a 30° C. oven and measuring the length of the gathered laminate about every 12 hours. Complete recovery is considered less than a 5% change in length in a 12 hour time period. After recovery is complete, the laminate is stored securely for at least 12 hours at room temperature before testing.

Stretch laminates L1b and L2 in Table 5 are prepared from the corresponding extruded elastomeric film compositions in Table 2 (film F1b for laminate L1b, and film F2 for laminate L2), where five laminates are made from each Sample Film and where the spacing between each elastomeric film specimen for the laminate preparation is about 80 inches in the machine direction of manufacture. Laminate L2 represents a stretch laminate of the present disclosure while Laminate L1b represents a comparative stretch laminate.

The average maximum laminate strain (determined according to the Maximum Laminate Strain method), the initial percent strain for the Post Elongation Recovery Test, and the peak test strain for the Two-Cycle Hysteresis Test for Laminates are shown in Table 5. The initial percent strain for the Post Elongation Recovery Test and the peak strain for the Two-Cycle Hysteresis Test for Laminates are taken as 70% of the average maximum percent strain determined according to the Maximum Laminate Strain Test rounded up to the nearest multiple of five if the value does not result in a target strain that is divisible by five when rounded to the nearest percent. Stretch laminates L1b and L2 are measured according to the Two-Cycle Hysteresis Test for Laminates and the Post Elongation Recovery methods described in the Test Methods section above. The normalized unload force at 37° C. and the percent of initial strain after 15 seconds recovery at 22° C. (72° F.) and 37° C. (99° F.) are shown in Table 5. Additionally, Stretch laminates L1b and L2 are aged according to the Elastomer and Laminate Aging method described in the Test Methods section above. The unload forces of the aged and corresponding non-aged stretch laminates L1b and L2 are measured according to the Two-Cycle Hysteresis Test For Laminates method described in the Test Methods section above. The normalized unload force at 37° C. (99° F.) at the tested hold strains are shown in Table 5 along with the corresponding force retention factor at each hold strain. Table 5 shows the advantage of a slow recovery stretch laminate comprising an hydrogenated elastomer.

TABLE 5

Slow Recovery Stretch Laminate Properties and Aging

| Laminate Property | Laminate Aged?* | Sample Laminate Number | |
|---|---|---|---|
| | | L1b | L2 |
| Engineering strain of elastic film during laminate preparation | No | 450% | 280% |
| Maximum laminate strain (engineering strain) | No | 286% | 253% |
| Peak test strain for Two-Cycle Hysteresis test and Initial strain for Post Elongation Recovery test (engineering strain) | No | 200% | 180% |
| Normalized unload force at 37° C. (99° F.) and 60% strain [N/(g/m)] | No | 0.64 | 0.92 |
| Percent of initial strain after 15 seconds recovery at 22° C. (72° F.) | No | 21.4% | 35.6% |
| Percent of initial strain after 15 seconds recovery at 37° C. (99° F.) | No | 6.2% | 7.4% |
| Two-Cycle Hystereis - Laminate L1a** | | | |
| Unload force at 37° C. (99° F.) and 110% hold strain (Newtons per inch) | No | 1.64 | |
| | Yes | 0.88 | |
| Force Retention Factor*** | | 2.16 | |
| Unload force at 37° C. (99° F.) and 80% hold strain (Newtons per inch) | No | 1.28 | |
| | Yes | 0.61 | |
| Force Retention Factor*** | | 1.91 | |
| Unload force at 37° C. (99° F.) and 55% hold strain (Newtons per inch) | No | 0.96 | |
| | Yes | 0.33 | |
| Force Retention Factor*** | | 1.52 | |
| Unload force at 37° C. (99° F.) and 35% hold strain (Newtons per inch) | No | 0.68 | |
| | Yes | 0.05 | |
| Force Retention Factor*** | | 1.08 | |
| Two-Cycle Hystereis - Laminate L2** | | | |
| Unload force at 37° C. (99° F.) and 100% hold strain (Newtons per inch) | No | | 1.26 |
| | Yes | | 0.79 |
| Force Retention Factor*** | | | 2.68 |
| Unload force at 37° C. (99° F.) and 75% hold strain (Newtons per inch) | No | | 1.04 |
| | Yes | | 0.59 |
| Force Retention Factor*** | | | 2.31 |
| Unload force at 37° C. (99° F.) and 50% hold strain (Newtons per inch) | No | | 0.78 |
| | Yes | | 0.34 |
| Force Retention Factor*** | | | 1.77 |
| Unload force at 37° C. (99° F.) and 30% hold strain (Newtons per inch) | No | | 0.53 |
| | Yes | | 0.08 |
| Force Retention Factor*** | | | 1.18 |

*Laminate aged according to Film and Laminate Aging Method - 1 week at 40° C. and 50% engineering strain
**Laminate unload forces normalized to one inch laminate width
***Force Retention Factor = (No Aged Force)/(No Aged Force − Aged Force)

Example 4

Polymer Molecular Weight Determination

Polymer number average molecular weight and molecular weight distributions are determined by GPC SEC/MALS. The GPC uses a Waters Alliance 2695 HPLC autoinjeetor. It contains three Styragel HR columns (HR3, HR4 and HR5). The column heater is set to 30° C. The flow rate is 1.0 mL/min and the mobile phase is tetrahydrofuran, HPLC grade available from Sigma-Aldrich Inc., St. Louis, Mo. The detectors are a Wyatt Dawn EOS Light scattering detector calibrated with toluene and normalized using 100 kilo Dalton polystyrene (molecular weight standard available from Polysciences, Inc., Warrington, Pa.) in mobile phase and a Waters 2414 refractive index detector at 30° C. Samples for analysis are prepared at a known concentration of 2 mg/mL. Samples are filtered using 0.45 μm nylon membrane filters. The injection volume is 100 μl. The data is collected and analyzed using ASTRA 5.3.2.15. Values for dn/dc are calculated from the refractive index trace assuming 100% mass recovery.

Example 5

Low Molecular Weight Tetramethyl Bisphenol-A Polycarbonate (TMBAPC)

To a dry 1 L three neck flask is added 74 ml of 20% phosgene in toluene (available from Sigma-Aldrich) and 88 ml THF (available from Sigma-Aldrich). In a second flask 40.63 grams of tetramethyl bisphenol A (available from Sigma-Aldrich) is mixed with 50 ml anhydrous THF, 8.55 grams of 4-dimethylamino pyridine (available from Sigma-Aldrich), and 49 ml of diisopropylethylamine (available from Sigma-Aldrich). This solution is added via separatory funnel to the solution of phosgene over a 1H period maintaining the temperature between 6-13° C. The mixture is stirred for 48H. After 48 hours, the THF is evaporated. The product is redissolved in 500 ml methylene chloride (available from Sigma-Aldrich), which is washed with 250 ml water and 250 ml 10% citric acid. The solvent is then evaporated. Filtration provides 8.0 grams of a white solid.

Gel Permeation Chromotography (GPC) analysis by the method of Example 4 shows a number average molecular weight of Mn=2.0 kilo Daltons, and a molecular weight distribution of Mw/Mn=1.2, where Mw is the weight average molecular weight. Measurement of the glass transition temperature by the Hard Block Glass Transition method described in the Test Methods section shows a glass transition temperature of 142° C.

Example 6

Medium Molecular Weight TMBAPC

To a dry 1 L three neck flask is added 74 ml of 20% phosgene in toluene (available from Sigma-Aldrich) and 88 ml THF (available from Sigma-Aldrich). In a second flask 40.63 grams of tetramethyl bisphenol A (available from Sigma-Aldrich) is mixed with 50 ml anhydrous THF, 8.55 grams of 4-dimethylamino pyridine (available from Sigma-Aldrich), and 49 ml of diisopropylethylamine (available from Sigma-Aldrich). This solution is added via separatory funnel to the solution of phosgene over a 1H period maintaining the temperature between 6-13° C. The mixture is stirred for 48H. After 48 hours, the THF is evaporated. The product is redissolved in 500 ml methylene chloride (available from Sigma-Aldrich), which is washed with 250 ml water and 250 ml 10% citric acid. The solvent is then evaporated. Filtration provides 11.25 grams of a white solid.

Gel Permeation Chromatography (GPC) analysis by the method of Example 4 shows a number average molecular weight of Mn=5.65 kilo Daltons, and a molecular weight distribution of Mw/Mn=1.23. Measurement of the glass transition temperature by the Hard Block Glass Transition method described in the Test Methods section shows a glass transition temperature of 180° C.

Example 7

High Molecular Weight TMBAPC

To a dry 1 L three neck flask is added 74 ml (140 mmole) of 20% phosgene in toluene (available from Sigma-Aldrich) and 88 ml THF (available from Sigma-Aldrich). In a second flask 40.63 grams of tetramethyl bisphenol A (available from Sigma-Aldrich) is mixed with 50 ml dry THF, 8.55 grams of 4-dimethylamino pyridine (available from Sigma-Aldrich), and 49 ml of diisopropylethylamine (available from Sigma-Aldrich). This solution is added via separatory funnel to the solution of phosgene over a 1H period maintaining the temperature below 10° C. The solution is stirred for 5 hours at 5° C. and at room temperature (23° C.) for 72 hours. The THF is evaporated and the product is redissolved in 250 ml of methylene chloride (available from Sigma-Aldrich) and the solution is added dropwise to 1.4 L isopropanol. A precipitate forms and is collected providing 12.2 grams of a white solid.

GPC analysis by the method of Example 4 shows a number average molecular weight of Mn=9.59 kilo Daltons and a molecular weight distribution of Mw/Mn=1.20. Measurement of the glass transition temperature by the Hard Block Glass Transition method described in the Test Methods section shows a glass transition temperature of 192° C.

Example 8

High Molecular Weight TMBAPC with Benzyl End Groups

Five grams of the product from Example 7 is dissolved in 50 ml of methylene chloride (available from Sigma-Aldrich) to which is added 0.41 ml of triethylamine (available from Sigma-Aldrich), 0.01 grams of 4-Dimethylaminopyridine (available from Sigma-Aldrich), and 0.438 ml of benzyl chloroformate (available from Sigma-Aldrich). This is stirred at 23° C. for 16 hours. Analysis of an aliquot indicates 50% conversion. Additional portions of 0.41 ml of triethylamine and 0.438 ml of benzyl chloroformate are added each hour for two additional hours. The reaction is then diluted with 200 ml of methylene chloride and washed with water, then with 1N Hydrochloric acid, then washed with saturated sodium chloride solution. The solvent is then evaporated and the product is vacuum dried.

GPC analysis by the method of Example 4 shows a number average molecular weight of Mn=9.97 kilo Daltons and a molecular weight distribution of Mw/Mn=1.28. Measurement of the glass transition temperature by the Hard Block Glass Transition method described in the Test Methods section shows a glass transition temperature of 180° C. NMR analysis indicates the presence of terminal benzyl groups at about 100% substitution.

Example 9

Styrene Monomer Purification

Styrene (available from Sigma-Aldrich) is purified by passing through an activated alumina (available from Sigma-Aldrich) column under nitrogen atmosphere to remove inhibitors and then the styrene is added to a clean, dry round bottom flask filled with nitrogen and fitted with a rubber septum.

Example 10

Synthesis of Polystyrene

To a reactor at 60° C., is added 500 milliliters of cyclohexane (pesticide residue analysis (PRA) grade from Sigma-Aldrich) and 50 grams of styrene (as purified in Example 9). This is titrated with s-butyl lithium (available from Sigma-Aldrich) to a persistent yellow color and 1.0 ml of butyl lithium is added. After 20 minutes, 1 ml of methanol (available from Sigma-Aldrich) is added and the polymer solution is then precipitated into 3 liters of methanol to isolate the product.

GPC analysis by the method of Example 4 shows a number average molecular weight of Mn=38.0 kilo Daltons and a molecular weight distribution of Mw/Mn=1.03. Measurement of the glass transition temperature by the Hard Block Glass Transition method described in the Test Methods section shows a glass transition temperature of 85° C.

Example 11

Polystyrene Blends

Polymer blends B1-B3 listed in Table 6 are prepared by solution blending—(1) 0.75 grams of the polystyrene from Example 10 and 0.25 grams of the TMBAPC component are dissolved in 10 ml of chloroform (available from Sigma-Aldrich), (2) the solution is poured into a Teflon dish and loosely covered with a watch glass, (3) the solvent is allowed to evaporate slowly for 16 hours at room temperature (22° C.), and (4) the film is vacuum dried at 40° C. for 24 hours. Measurement of the glass transition temperature by the Hard Block Glass Transition method described in the Test Methods section shows the glass transition temperatures listed in Table 6.

TABLE 6

Blend Compositions (weight percent) and Glass Transition Temperatures

| | Blend or Example Number | | | | | | |
|---|---|---|---|---|---|---|---|
| | Example 10 | Example 5 | B1 | Example 7 | B2 | Example 8 | B3 |
| Blend Component* | | | | | | | |
| Low MW TMBAPC from Example 5 | | 100% | 25% | | | | |
| High MW TMBAPC from Example 7 | | | | 100% | 25% | | |
| High MW TMBAPC with benzyl end groups from Example 8 | | | | | | 100% | 25% |
| Polystyrene homopolymer from Example 10 | 100% | | 75% | | 75% | | 75% |
| Blend Property | | | | | | | |
| Glass transition temperature (° C.) | 85° C. | 142° C. | 98° C. | 192° C. | 89° C. | 180° C. | 97° C. |

*Component percentages are weight percent

Example 12

Compression molded films of elastomer compositions F9 and F10 listed in Table 7 are prepared, where film F9 is prepared according to the film preparation methods described in Example 1 with metal temperatures of the mixer set to about 205° C. and film F10 is prepared according to the film preparation methods described in Example 15. The weight ratio of added elastomer (Septon 4033) to modifying resin (Eastotac H-142R) to mineral oil (White Britol 50T) in elastomer film F9 is equivalent to that in elastomer film F3, and the weight ratio of added elastomer1 (Septon 4033) to elastomer2 (Septon 4044) to modifying resin (Eastotac H-142R) to mineral oil (White Britol 50T) in elastomer film F10 is equivalent to that in elastomer film F5.

Films of the elastomer compositions in Table 7 are measured according to the Order-Disorder Temperature and Post Elongation Recovery methods described in the Test Methods section above. The order-disorder temperature (ODT) and the percent of initial strain after 15 seconds recovery at 22° C. (72° F.) and 37° C. (99° F.) are shown in Table 8. Additionally, films of the elastomer compositions F1a, F3, F5, F9, and F10 in Table 7 are aged according to the Elastomer and Laminate Aging method described in the Test Methods section above. The corresponding non-aged control films of elastomer compositions F1a, F3, F5, F9, and F10 in Table 7 are prestrained to 300% engineering strain and allowed to recover according to the Elastomer and Laminate Aging method described in the Test Methods section above. The unload forces of the aged and non-aged elastomer films are measured according to the Two-Cycle Hysteresis Test For Elastomers method described in the Test Methods section above. The normalized unload force at 37° C. (99° F.) and hold strains of 60%, 100%, 150%, and 200% engineering strain are shown in Table 8 along with the corresponding force retention factor at each hold strain. Table 8 shows the advantage of adding a high glass transition temperature hard block modifier to a block copolymer composition comprising an hydrogenated elastomer.

TABLE 7

Slow Recovery Elastomer Compositions (weight percent)

| | Sample Film Number** | | | | | | |
|---|---|---|---|---|---|---|---|
| | F1a | F1b | F2 | F3 | F9 | F5 | F10 |
| Film Component* | | | | | | | |
| Vector 4211 (SIS, 29 wt % styrene) | 48.5% | 48.5% | | | | | |
| Septon 4033 (SEEPS, 30 wt % styrene) | | | 44.6% | 44.6% | 43.2% | 33.5% | 32.4% |
| Septon 4044 (SEEPS, 32 wt % styrene) | | | | | | 11.2% | 10.8% |
| Arkon P140 | 48.5% | 48.5% | | | | | |
| Eastotac H-142R | | | 53.5% | 53.5% | 51.8% | 53.5% | 51.8% |
| Mineral Oil (White Britol 50T) | 3.0% | 3.0% | 1.9% | 1.9% | 1.8% | 1.9% | 1.8% |
| TMBAPC from Example 6 | | | | | 3.2% | | 3.2% |
| Film Property | | | | | | | |
| Film type (E = extruded, CM = compression molded) | E | E | E | CM | CM | CM | CM |
| Arithmetic average film basis weight (grams per square meter) | 131 | 140 | 88 | 157 | 179 | 173 | 276 |

*Weight percent styrene are nominal values based on manufacturer's technical data sheet. Component percentages are weight percent.

**Samples F1a and F1b are comparative examples; Samples F2, F3, F5, F9, and F10 are embodiments of the present invention.

TABLE 8

Elastomer Order-Disorder Temperature and Aging

| Film Property | Film Aged? * | F1a | F2 | F3 | F9 | F5 | F10 |
|---|---|---|---|---|---|---|---|
| Order-Disorder Temperature (ODT) | No | 156° C. | 151° C. | 157° C. | 166° C. | 200° C. | 206° C. |
| Percent of initial strain after 15 seconds recovery at 22° C. (72° F.) | No | 34.9% | 52.9% | 39.5% | 54.1% | 44.3% | 49.7% |
| Percent of initial strain after 15 seconds recovery at 37° C. (99° F.) | No | 11.6% | 8.4% | 3.0% | 5.9% | 3.0% | 4.0% |
| Normalized unload force at 37° C. (99° F.) and 200% hold strain (Newtons) | No | 0.51 | 1.28 | 1.16 | 1.01 | 1.06 | *** |
|  | Yes | 0.20 | 0.92 | 1.00 | 0.90 | 0.96 | *** |
| Force Retention Factor ** |  | 1.65 | 3.56 | 7.25 | 9.18 | 10.6 |  |
| Normalized unload force at 37° C. (99° F.) and 150% hold strain (Newtons) | No | 0.41 | 1.06 | 0.98 | 0.82 | 0.89 | 0.92 |
|  | Yes | 0.14 | 0.75 | 0.83 | 0.74 | 0.81 | 0.84 |
| Force Retention Factor ** |  | 1.52 | 3.42 | 6.53 | 10.3 | 11.1 | 11.5 |
| Normalized unload force at 37° C. (99° F.) and 100% hold strain (Newtons) | No | 0.31 | 0.84 | 0.79 | 0.65 | 0.72 | *** |
|  | Yes | 0.05 | 0.54 | 0.63 | 0.56 | 0.63 | *** |
| Force Retention Factor ** |  | 1.19 | 2.80 | 4.94 | 7.22 | 8.00 |  |
| Normalized unload force at 37° C. (99° F.) and 60% hold strain (Newtons) | No | 0.22 | 0.64 | 0.59 | 0.48 | 0.53 | 0.54 |
|  | Yes | 0.01 | 0.31 | 0.40 | 0.36 | 0.42 | 0.45 |
| Force Retention Factor ** |  | 1.05 | 1.94 | 3.11 | 4.00 | 4.82 | 6.00 |

* Film aged according to Elastomer and Laminate Aging Method - 1 week at 40° C. and 100% engineering strain; films not aged for Two Cycle Hysteresis Test are prestrained to 300% engineering strain then allowed to recover according to the procedure outlined in the Elastomer and Laminate Aging Method.
** Force Retention Factor = (Non Aged Film Force)/(Non Aged Film Force − Aged Film Force)
*** Not measured Example 13

Extruded films containing about 94% by weight of the elastomer composition F2 in Table 2 and about 6% by weight of homopolymer polystyrene (3190 available from INEOS NOVA LLC, Channahon, Ill.) are prepared according to the film preparation methods described in Example 1, where the polystyrene is ground and sieved so that particle sizes predominantly in the size range from about 0.047 inches (United States sieve size 16) to about 0.079 inches (United States sieve size 10) are extruded. Film samples are tested according to the Two-Cycle Hysteresis Test For Elastomers, and the Order Disorder Temperature (ODT) and Post Elongation Recovery methods described in the Test Methods section above. The ODT is about 201° C., the normalized unload force is about 0.45 Newton's at 37° C. and 60% hold strain, the percent of initial strain after 15 seconds recovery at 22° C. is about 65%, and the percent of initial strain after 15 seconds recovery at 37° C. is about 16%. Further, at equivalent basis weights, the tensile strength shows about a 27% increase over the elastomer composition F2 in Table 2, where the tensile strength is determined according to ASTM D 882 using a 1 inch sample width, a 1 inch gage length, and a crosshead speed of 10 inches per minute.

Example 14

Polystyrene Block Copolymer with High Glass Transition Temperature Soft Block

To a reactor at 25° C. is added 3 liters of cyclohexane (pesticide residue analysis (PRA) grade from Sigma-Aldrich), 30 ml of Tetrahydrofuran (anhydrous grade available from Sigma-Aldrich), and 50 grams of styrene (purified as described in Example 9). This is titrated with s-butyl lithium (available from Sigma-Aldrich) to a persistent yellow color, and 3.1 ml of s-butyl lithium is added to give the desired molecular weight. After 20 minutes, a sample is taken and 234 grams of isoprene (available from Sigma-Aldrich) is added to the reactor. This is allowed to react for 180 minutes maintaining the temperature at 25° C. A sample is taken for analysis and 50 grams of styrene (purified as described in Example 9) is added. After 20 minutes the reaction is terminated with methanol. A 20 gram sample is taken for GPC analysis and glass transition testing, stabilized with 0.1 weight percent Irganox 1010 (available from BASF, Florham Park, N.J.), and vacuum dried.

GPC analysis by the method of Example 4 shows a number average molecular weight of Mn=80 kilo Daltons and a molecular weight distribution of Mw/Mn=1.04. Measurement of the glass transition temperature by the Hard Block Glass Transition method described in the Test Methods section shows a soft block glass transition temperature of 13° C.

Example 15

Film blends of elastomer compositions F11-F14 in Table 9 are prepared by solution blending and compression molding into films. This method consists of—(1) dissolving all components in a suitable solvent, e.g., chloroform, where the weight percent of solids is about 5%, (2) pouring the solution into a petri-dish, or other suitable container, and allowing to dry overnight at room temperature, (3) vacuum drying the films at about 120° C. for about 1 hour, and (4) preparing compression molded films according to the methods described in Example 1. Compression molded films of the elastomer compositions F11-F14 in Table 9 are measured according to the Post Elongation Recovery method described in the Test Methods section. The percent of initial strain after 15 seconds at 22° C. (72° F.) is shown in Table 9.

TABLE 9

Elastomer composition (weight percent) and Post Elongation Recovery

| | Sample Film Number | | | |
|---|---|---|---|---|
| Film Component* | F11 | F12 | F13 | F14 |
| Polystyrene block copolymer from Example 14 | 100.0% | 94.0% | 89.0% | 81.0% |

TABLE 9-continued

Elastomer composition (weight percent)
and Post Elongation Recovery

| | Sample Film Number | | | |
|---|---|---|---|---|
| | F11 | F12 | F13 | F14 |
| Arkon P140 | | 5.0% | 10.0% | 15.0% |
| Mineral Oil (White Britol 50T) | | 1.0% | 1.0% | 4.0% |
| Film Property | | | | |
| Percent of initial strain after 15 seconds recovery at 22° C. (72°) | 4.2% | 15.9% | 30.8% | 44.9% |

*Component percentages are weight percent

Example 16

Randomization Catalyst

A randomization catalyst is generated by the reaction of 1 gram of potassium metal (available from Sigma-Aldrich) with 1.16 grams of 2,3-dimethyl-3-pentanol (available from Sigma-Aldrich) dissolved in 50 ml of cyclohexane (PRA grade available from Sigma-Aldrich).

Example 17

Synthesis of Poly(styrene-isoprene) Random Copolymer

To a reactor at 60° C., is added 1 liter of cyclohexane (pesticide residue analysis (PRA) grade (available from Sigma-Aldrich) and 22 grams of styrene (as purified in Example 9). This is titrated with s-butyl lithium (available from Sigma-Aldrich) to a persistent yellow color and 38 grams of isoprene (available from Sigma-Aldrich) is added to the reactor. To this is added 0.7 ml of s-butyl lithium. This is followed by addition of 0.2 ml of the randomization catalyst prepared as described in Example 16. A sample is taken for analysis and the reaction is terminated by addition of methanol (available from Sigma-Aldrich), stabilized with 0.1 weight percent Irganox 1010 (available from BASF, Florham Park, N.J.), and vacuum dried.

GPC analysis by the method of Example 4 shows a number average molecular weight of Mn=56.0 kilo Daltons and a molecular weight distribution of Mw/Mn=1.03. Measurement of the glass transition temperature by the Hard Block Glass Transition method described in the Test Methods section shows a glass transition temperature of negative 42° C. (−42° C.).

Example 18

Synthesis of First Medium Molecular Weight Polystyrene Block Copolymer with Random Styrene-Isoprene Soft Block To a reactor at 65° C., is added 3 liters of cyclohexane (pesticide residue analysis (PRA) grade (available from Sigma-Aldrich) and 58 grams of styrene (as purified in Example 9). This is titrated with s-butyl lithium (available from Sigma-Aldrich) to a persistent yellow color and 3.5 ml of butyl lithium is added to give the desired molecular weight. This is followed by addition of 1 ml of the randomization catalyst prepared as described in Example 16. After 20 minutes, a sample is taken and 135 grams of isoprene (available from Sigma-Aldrich) and 45 grams of styrene (as purified in Example 9) are added to the reactor. This is allowed to react for 45 minutes maintaining the temperature at 50° C. A sample is taken for analysis and 39 grams of styrene (as purified in Example 9) is added. After 20 minutes the reaction is terminated with methanol. A 20 gram sample is taken for analysis and testing, stabilized with 0.1 weight percent Irganox 1010 (available from BASF, Florham Park, N.J.), and vacuum dried.

GPC analysis by the method of Example 4 shows the $1^{st}$ block with a number average molecular weight of Mn=13.0 kilo Daltons and a molecular weight distribution of Mw/Mn=1.07, the diblock with a number average molecular weight of Mn=52.0 kilo Daltons and a molecular weight distribution of Mw/Mn=1.02, and the final triblock with a number average molecular weight of Mn=62.0 kilo Daltons and a molecular weight distribution of Mw/Mn=1.02. Measurement of the glass transition temperature by the Hard Block Glass Transition method described in the Test Methods section shows a soft block glass transition temperature of 14° C.

Example 19

Synthesis of High Molecular Weight Polystyrene Block Copolymer with Random Styrene-Isoprene Soft Block To a reactor at 25° C., is added 3 liters of cyclohexane (pesticide residue analysis (PRA) grade (available from Sigma-Aldrich), 1 ml of anhydrous THF (available from Sigma-Aldrich) and 35 grams of styrene (as purified in Example 9). This is titrated with s-butyl lithium (available from Sigma-Aldrich) to a persistent yellow color and 1.7 ml of butyl lithium is added to give the desired molecular weight. After 20 minutes, a sample is taken and 180 grams of isoprene (available from Sigma-Aldrich) and 60 grams of styrene (as purified in Example 9) are added to the reactor. This is allowed to react for 180 minutes maintaining the temperature at 25° C. A sample is taken for analysis and 30 grams of styrene (as purified in Example 9) is added. After 20 minutes the reaction is terminated with methanol. A 20 gram sample is taken for analysis and testing, stabilized with 0.1 weight percent Irganox 1010 (available from BASF, Florham Park, N.J.), and vacuum dried.

GPC analysis by the method of Example 4 shows the $1^{st}$ block with a number average molecular weight of Mn=15.0 kilo Daltons and a molecular weight distribution of Mw/Mn=1.07, the diblock with a number average molecular weight of Mn=126 kilo Daltons and a molecular weight distribution of Mw/Mn=1.09, and the final triblock with a number average molecular weight of Mn=142 kilo Daltons and a molecular weight distribution of Mw/Mn=1.02. Measurement of the glass transition temperature by the Hard Block Glass Transition method described in the Test Methods section shows a soft block glass transition temperature of 15° C.

Example 20

Film blends of elastomer compositions F15-F17 in Table 10 are prepared by solution blending and compression molding into films according to the methods of Example 15. Compression molded films of the elastomer compositions F11-F14 in Table 10 are measured according to the Post Elongation Recovery method described in the Test Methods section. The percent of initial strain after 15 seconds at 22° C. (72° F.) is shown in Table 10.

TABLE 10

Elastomer composition (weight percent)
and Post Elongation Recovery

| | Sample Film Number | | |
|---|---|---|---|
| | F15 | F16 | F17 |
| Film Component* | | | |
| Polystyrene block copolymer from Example 18 | 75.0% | | |
| Polystyrene block copolymer from Example 19 | | 70.0% | 100.0% |
| Random copolymer from Example 17 | 20.0% | 20.0% | |
| Polystyrene homopolymer from Example 13 | | 10.0% | |
| SHF-61 oil** | 5.0% | | |
| Film Property | | | |
| Percent of initial strain after 15 seconds recovery at 22° C. (72°) | 34.8% | 48.5% | 65.0% |

*Component percentages are weight percent
**Available from Exxon-Mobil, Houston, TX Example 21

Purification of T-Butyl Styrene

Tert-butyl styrene (available from Sigma-Aldrich) is purified by passing through an activated alumina (available from Sigma-Aldrich) column under nitrogen atmosphere to remove inhibitors and then the t-butyl styrene is added to a clean, dry round bottom flask filled with nitrogen and fitted with rubber septa.

Example 22

Hydrogenation Catalyst

Hydrogenation catalyst is prepared as follows; 0.345 grams of nickel(2-ethyl hexanoate) (0.001 mole) (available from Sigma-Aldrich) is dissolved in 30 ml of cylcohexane (PRA grade available from Sigma-Aldrich). To this is added 3 ml of triethylaluminum (0.003 mole) (1.0M in hexanes available from Sigma-Aldrich) resulting in a black dispersion of nickel catalyst.

Example 23

Preparation of Acetyl Nitrate

A solution of acetyl nitrate is prepared as follows. To 600 ml of methylene chloride (available from Sigma-Aldrich) is added 320 grams of acetic anhydride (available from Sigma-Aldrich) and this is cooled to 0° C. To this is slowly added 100 grams of nitric acid (available from Sigma-Aldrich), while maintaining the temperature at 0° C. This is allowed to react for 60 minutes at 0° C.

Example 24

Synthesis of Polystyrene Block Copolymer with Isoprene Soft Block

To a clean reactor at 60° C. is added 3 liters of cyclohexane (pesticide residue analysis (PRA) grade from Sigma Aldrich) and 60 grams of styrene (as purified in Example 9). This is titrated with s-butyl lithium (available from Sigma-Aldrich) to a persistent yellow color and 5 mmole of s-butyl lithium is added to give the desired molecular weight. After 20 minutes, a sample is taken and 280 grams of isoprene (available from Sigma-Aldrich) is added to the reactor. This is allowed to react for 45 minutes maintaining the temperature at 60° C. A sample is taken for analysis and 60 grams of styrene (as purified in Example 9) is added. After 20 minutes the reaction is terminated with degassed methanol. A sample is taken for analysis, stabilized with 0.1 weight percent Irganox 1010 (available from BASF), and vacuum dried. The polymer solution is precipitated by pouring it into a large excess of methanol with vigorous stirring. The polymer precipitate is filtered and Irganox 1010 is added to stabilize the polymer which is then vacuum dried.

GPC analysis by the method of Example 4 shows the $1^{st}$ block with a number average molecular weight of Mn=12.8 kilo Daltons and a molecular weight distribution of Mw/Mn=1.08, the final triblock with a number average molecular weight of 80.0 kilo Daltons and a molecular weight distribution of Mw/Mn=1.02, and an overall composition of 27 weight percent styrene and 73 weight percent isoprene. Measurement of the final triblock glass transition temperature according to the Hard Block Glass Transition method described in the Test Methods section shows a soft block glass transition temperature of −61° C. and a hard block glass transition temperature of 65° C.

Example 25

Hydrogenation of Polystyrene Block Copolymer with Isoprene Soft Block 300 grams of the polymer from Example 24 is dissolved in 2500 ml of cyclohexane (pesticide residue analysis (PRA) grade from Sigma-Aldrich). This solution is degassed by bubbling nitrogen thru it for two minutes. This solution is added to a pressure reactor and the hydrogenation catalyst from Example 22 is added and 50 psi of hydrogen pressure is maintained while providing vigorous stirring (500 rpm). The hydrogenation is carried out for 16 hours at which point the polymer solution is removed from the reactor into a jar with a solution of 1 liter of 0.5 molar HCl. This is mixed with vigorous agitation until the black catalyst is oxidized and the polymer solution becomes clear. The mixture is allowed to settle into two layers and the water layer is discarded. To the polymer/cyclohexane solution is added 1 liter of 0.5M aqueous sodium hydroxide solution (available from Sigma-Aldrich). This is mixed vigorously for 5 minutes and then allowed to settle into two layers. The aqueous layer is discarded and the polymer/cyclohexane layer is stabilized with 0.1 weight percent Irganox 1010 (available from BASF) and the polymer solution is then dried to isolate the polymer. NMR analysis of the dried polymer shows about 100% hydrogenation of the isoprene double bonds.

Example 26

Nitration of Polystyrene Block Copolymer with Ethylene/Propylene Soft Block 50 grams of the polymer from Example 25 is dissolved in 500 ml of methylene chloride (available from Sigma-Aldrich) at 0° C., along with 20 ml of acetic anhydride (available from Sigma-Aldrich) to which is added 129 ml of the acetyl nitrate from Example 25. This mixture is reacted for 120 minutes at 0° C., and the reaction is stopped by precipitation of the solution into 3 liters of methanol. Elemental analysis shows a 30% degree of nitration.

Example 27

Synthesis of Second Medium Molecular Weight Polystyrene Block Copolymer with Random Styrene-Isoprene Soft Block To a clean reactor at 60° C. is added 3 liters of cyclohexane (pesticide residue analysis (PRA) grade from Sigma-Aldrich) and 60 grams of styrene (as purified in Example 9). This is titrated with s-butyl lithium (available from Sigma-Aldrich) to a persistent yellow color and 5 mmole of s-butyl lithium is added to give the desired molecular weight. This is followed by addition of 0.2 mmole (1 ml) of the randomization catalyst from Example 16. After 20 minutes, a sample is taken and 95 grams of isoprene (available from Sigma-Aldrich) and 85 grams of styrene (as purified in Example 9) is added to the reactor. This is allowed to react for 45 minutes maintaining the temperature at 50° C. A sample is taken for analysis and 40 grams of styrene (as purified in Example 9) is added. After 20 minutes the reaction is terminated with degassed methanol. A 20 gram sample is taken for analysis and testing, stabilized with 0.1 weight percent Irganox 1010 (available from BASF), and vacuum dried.

GPC analysis of the final triblock by the method of Example 4 shows a number average molecular weight of Mn=65 kilo Daltons and a molecular weight distribution of Mw/Mn=1.03. Measurement of the final triblock glass transition temperature according to the Hard Block Glass Transition method described in the Test Methods section shows a hard block glass transition temperature of 51° C. Measurement of the final triblock order-disorder transition (ODT) temperature according to the Order-Disorder Temperature method described in the Test Methods section shows an ODT of 90° C.

Example 28

Hydrogenation of Second Medium Molecular Weight Polystyrene Block Copolymer with Random Styrene-Isoprene Soft Block 150 grams of the polymer from Example 27 is dissolved in 2500 ml of cyclohexane (pesticide residue analysis (PRA) grade from Sigma-Aldrich). This solution is degassed by bubbling nitrogen thru it for two minutes. This solution is added to a pressure reactor and the hydrogenation catalyst from Example 22 is added and 50 psi of hydrogen pressure is maintained while providing vigorous stirring (500 rpm). The hydrogenation is carried out for 16 hours at which point the polymer solution is removed from the reactor into a jar with a solution of 1 liter of 0.5 molar HCl. This is mixed with vigorous agitation until the black catalyst is oxidized and the polymer solution becomes clear. The mixture is allowed to settle into two layers and the water layer is discarded. To the polymer/cyclohexane solution is added 1 liter of 0.5M aqueous sodium hydroxide solution. This is mixed vigorously for 5 minutes and then allowed to settle into two layers. The aqueous layer is discarded and the polymer/cyclohexane layer is stabilized with 0.1 weight percent Irganox 1010 (available from BASF) and the polymer solution is then dried to isolate the polymer. NMR analysis of the dried polymer shows about 100% hydrogenation of the isoprene double bonds.

Measurement of the glass transition temperatures according to the Hard Block Glass Transition method described in the Test Methods section shows a soft block glass transition temperature of −12° C. and a hard block glass transition temperature of 81° C. Measurement of the order-disorder transition (ODT) temperature according to the Order-Disorder Temperature method described in the Test Methods section shows an ODT of 166° C.

Example 29

Nitration of Medium Molecular Weight Polystyrene Block Copolymer with Random Styrene-Ethylene/Propylene Soft Block 50 grams of the polymer from Example 28 is dissolved in 500 ml of methylene chloride (available from Sigma-Aldrich) at 0° C., to which is added 20 ml of acetic anhydride (available from Sigma-Aldrich) and 129 ml of the acetyl nitrate from Example 23. This mixture is reacted for 120 minutes at 0° C., and the reaction is stopped by precipitation of the solution into 3 liters of methanol. The precipitate is further washed with a 50/50 by volume ethanol/water solution then soaked in water overnight. The polymer is then washed with ethanol and vacuum dried.

Measurement of the glass transition temperatures according to the Hard Block Glass Transition method described in the Test Methods section shows a soft block glass transition temperature of −21° C. and a hard block glass transition temperature of 97° C. Measurement of the order-disorder transition (ODT) temperature according to the Order-Disorder Temperature method described in the Test Methods section shows an ODT of greater than 250° C.

Example 30

Synthesis of Polystyrene Block Copolymer with Random t-Butyl Styrene-Isoprene Soft Block To a clean reactor at 20° C., is added 3 liters of cyclohexane (pesticide residue analysis (PRA) grade from Sigma-Aldrich), 2 ml of tetrahydrofuran (available from Sigma-Aldrich) and 60 grams of styrene (as purified in Example 9). This is titrated with s-butyl lithium (available from Sigma-Aldrich) to a persistent yellow color and 5 mmole of s-butyl lithium is added to give the desired molecular weight. After 20 minutes, a sample is taken and 132 grams of isoprene (available from Sigma-Aldrich) along with 55 grams of purified t-butyl styrene (as prepared in Example 21) are added to the reactor. This is allowed to react for 180 minutes maintaining the temperature at 30° C. A sample is taken for analysis and 40 grams of styrene (as purified in Example 9) is added. After 20 minutes the reaction is terminated with degassed methanol. A 20 gram sample is taken for analysis and testing, stabilized with 0.1 weight percent Irganox 1010 (available from BASF), and vacuum dried.

GPC analysis of the final triblock by the method of Example 4 shows a number average molecular weight of Mn=80 kilo Daltons and a molecular weight distribution of Mw/Mn=1.01. Measurement of the final triblock glass transition temperatures according to the Hard Block Glass Transition method described in the Test Methods section shows a soft block glass transition temperature of 6° C. Measurement of the final triblock order-disorder transition (ODT) temperature according to the Order-Disorder Temperature method described in the Test Methods section shows an ODT of 141° C.

Example 31

Hydrogenation of Polystyrene Block Copolymer with Random t-Butyl Styrene-Isoprene Soft Block 200 grams of the polymer from Example 30 is dissolved in 2500 ml of cyclohexane (pesticide residue analysis (PRA) grade from Sigma-Aldrich). This solution is degassed by bubbling nitrogen thru it for two minutes. This solution is added to a pressure reactor and the hydrogenation catalyst from Example 22 is added and 50 psi of hydrogen pressure is maintained while providing vigorous stirring (500 rpm). The hydrogenation is carried out for 16 hours at which point the polymer solution is removed from the reactor into a jar with a solution of 1 liter of 0.5 molar HCl. This is mixed with vigorous agitation until the black catalyst is oxidized and the polymer solution becomes clear. The mixture is allowed to settle into two layers and the water layer is discarded. To the polymer/cyclohexane solution is added 1 liter of 0.5M aqueous sodium hydroxide solution. This is mixed vigorously for 5 minutes and then allowed to settle into two layers. The aqueous layer is discarded and the polymer/cyclohexane layer is stabilized with 0.1 weight percent Irganox 1010 (available from BASF) and the polymer solution is then dried to isolate the polymer. NMR analysis of the dried polymer shows about 100% hydrogenation of the isoprene double bonds.

Measurement of the glass transition temperatures according to the Hard Block Glass Transition method described in the Test Methods section shows a soft block glass transition temperature of 5° C. Measurement of the order-disorder transition (ODT) temperature according to the Order-Disorder Temperature method described in the Test Methods section shows an ODT of 176° C.

Example 32

Nitration of Polystyrene Block Copolymer with Random t-Butyl Styrene-Ethylene/Propylene Soft Block 50 grams of the polymer from Example 31 is dissolved in 500 ml of methylene chloride (available from Sigma-Aldrich) at 0° C., to which is added 50 ml of acetic anhydride (available from Sigma-Aldrich) and 138 ml of the acetyl nitrate prepared in Example 23. This mixture is reacted for 120 minutes at 0° C., and the reaction is stopped by precipitation of the solution into 5 liters of ethanol. The precipitate is further washed with ethanol and vacuum dried overnight.

Measurement of the glass transition temperatures according to the Hard Block Glass Transition method described in the Test Methods section shows a hard block glass transition temperature of 96° C. Measurement of the order-disorder transition (ODT) temperature according to the Order-Disorder Temperature method described in the Test Methods section shows an ODT of 220° C.

Example 33

Nitration of Polystyrene Block Copolymer with Random Ethylene-Ethylene/Propylene Soft Block 25.4 grams of Septon 4033 (available from Kuraray America Inc., Pasedena, Tex.) is dissolved in 500 ml of methylene chloride (available from Sigma-Aldrich) at 0° C. Separately, 12.66 grams of chlorine is condensed into 52.75 grams of methylene chloride. 12.66 grams of this chlorine solution is added into the Septon solution and allowed to mix at room temperature (22° C.). After two days of reaction, 15 ml of acetic anhydride is added to the Septon solution and this is allowed to stir for one hour. A separate solution of 100 ml of methylene chloride and 30.24 grams of acetic anhydride is made and cooled to 0° C. and then 13.1 grams of nitric acid is added slowly. This acetyl-nitrate solution is added drop wise to the Septon solution which is cooled to −10° C. The entire reaction is kept in the dark. After two hours at −10° C., the reaction is allowed to warm to 0° C. for an additional hour of reaction, then it is precipitated into 3 liters of methanol. This mixture is filtered and washed with 50/50 by volume ethanol/water, then soaked in water overnight. The next day this is filtered and washed with ethanol and then vacuum dried.

GPC analysis by the method of Example 4 shows a number average molecular weight of Mn=85 kilo Daltons and a molecular weight distribution of Mw/Mn=1.09. Elemental analysis shows a 32% degree of nitration.

Example 34

An elastomer composition consisting of 45.1 wt % of the polymer from Example 33, 53.0 wt % Eastotac H-142R modifying resin (available from Eastman Chemical Company, Kingsport, Tenn.), and 1.9 wt % Britol® 50T mineral oil (available from Crompton Corporation, Petrolia, Pa.) is prepared according to the method of Example 15 with dichloromethane (available from Sigma-Aldrich) as the solvent. Compression molded films are prepared from the polymer blend according to the methods described in Example 1 with the blend pressed initially at 180° C. for 30 seconds at 1000 psi and then 30 seconds at 10,000 psi, and then at 225° C. for 45 seconds at 15,000 psi.

Films of this elastomer composition are measured according to the Post Elongation Recovery and Order Disorder Temperature (ODT) methods described in the Test Methods section above. These analyses show the percent of initial strain after 15 seconds recovery at 22° C. is 39% and the ODT is greater than 250° C. Additionally, films of this elastomer composition are aged according to the Elastomer and Laminate Aging method described in the Test Methods section above. The corresponding non-aged control films of this elastomer composition are prestrained to 300% engineering strain and allowed to recover according to the Elastomer and Laminate Aging method described in the Test Methods section above. The unload forces of the aged and non-aged elastomer films are measured according to the Two-Cycle Hysteresis Test For Elastomers method described in the Test Methods section above. The normalized unload forces at 37° C. (99° F.) and hold strains of 60%, 100%, 150%, and 200% engineering strain are shown in Table 11 along with the corresponding force retention factor at each hold strain.

TABLE 11

Aging of Block Copolymer Composition Comprising Nitrated Block Copolymer

| Film Property | Hold Strain | | | |
|---|---|---|---|---|
| | 200% | 150% | 100% | 60% |
| Non-aged film normalized unload force at 37° C. (Newtons)* | 1.17 | 0.98 | 0.79 | 0.61 |
| Aged film normalized unload force at 37° C. (Newtons)* | 0.81 | 0.66 | 0.51 | 0.37 |
| Force Retention Factor** | 3.25 | 3.06 | 2.82 | 2.54 |

*Film aged according to Elastomer and Laminate Aging Method - 1 week at 40° C. and 100% engineering strain; films not aged for Two Cycle Hysteresis Test are prestrained to 300% engineering strain then allowed to recover according to the procedure outlined in the Elastomer and Laminate Aging Method.
**Force Retention Factor = (Non Aged Film Force)/(Non Aged Film Force − Aged Film Force)

Example 35

Samples of the following materials are tested according to the Oil Exposure method described in the Test Methods section using Johnson's Baby Oil (available in the U.S. from Johnson & Johnson, New Brunswick, N.J. where mineral oil and fragrance are the listed ingredients) and isopropyl palmitate (90+% available from Sigma-Aldrich): (1) elastomer film F3 from Example 1, (2) elastomer film from Example 34, and (3) elastomer resin Septon 4033 (available from Kuraray America Inc., Pasedena, Tex.). After 30 hours exposure to excess baby oil at room temperature, all three materials are swollen with oil and remain intact, and both the elastomer film F3 from Example 1 and the elastomer film from Example 34 are readily discernable by hand to be stretchable to at least about 500% engineering strain. By contrast, after 30 hours exposure to excess isopropyl palmitate at room temperature, both the elastomer film F3 from Example 1 and the Septon 4033 resin are completely dissolved while the elastomer film from Example 34 remains intact and is readily discernable by hand to be stretchable to at least about 100% engineering strain.

Example 36

Prophetic

Table 12 shows the solubility parameters of various substituted polystyrenes, and Tables 13-15 show the solubility parameters of various random copolymers of styrene and substituted styrene. The solubility parameters are determined according to the method described by L. H. Sperling in *Introduction to Physical Polymer Science*, Wiley-Interscience (New York, 1992). Additionally, according to the method described by Sperling, the solubility parameter of polystyrene is 8.96 $(cal/cm^3)^{1/2}$, the solubility parameter of isopropyl palmitate is 8.12 $(cal/cm^3)^{1/2}$, and the solubility parameter of mineral oil (dodecane) is 7.75 $(cal/cm^3)^{1/2}$, where the densities used in determining these solubility parameters are 1.04 $g/cm^3$, 0.85 $g/cm^3$, and 0.75 $g/cm^3$, respectively.

TABLE 12

Solubility Parameters of Substituted Polystyrenes

| Chemical Name | Chemical Abbreviation* | Solubility Parameter [$(cal/cm^3)^{1/2}$] | | |
|---|---|---|---|---|
| | | Monofunctional** | Difunctional** | Trifunctional** |
| Nitro substituted polystyrene | NO2-PS | 9.86 (1.1) | 10.07 (1.1) | 10.20 (1.1) |
| Chlorine substituted polystyrene | Cl-PS | 10.10 (1.2) | 10.79 (1.3) | 11.92 (1.46) |
| Bromine substituted polystyrene | Br-PS | 10.14 (1.5) | 11.74 (1.95) | 12.93 (2.3) |
| Nitrile substituted polystyrene | CN-PS | 11.14 (1.1) | 12.26 (1.1) | 13.06 (1.1) |
| Methyl ketone substituted polystyrene | Me-CO-PS | 9.49 (1.0) | — | — |
| Ethyl ketone substituted polystyrene | Et-CO-PS | 9.49 (1.0) | — | — |
| Propyl ketone substituted polystyrene | Pr-CO-PS | 9.49 (1.0) | — | — |
| Butyl ketone substituted polystyrene | Bu-CO-PS | 9.39 (0.99) | — | — |
| Pentyl ketone substituted polystyrene | Pen-CO-PS | 9.06 (0.96) | — | — |
| Hexyl ketone substituted polystyrene | Hex-CO-PS | 8.92 (0.94) | — | — |
| Phenyl ketone substituted polystyrene | Ph-CO-PS | 9.16 (1.0) | — | — |
| Methyl acetylester substituted polystyrene | Me-COO-PS | 9.71 (1.1) | 9.76 (1.1) | 9.79 (1.1) |
| Butyl acetylester substituted polystyrene | Bu-COO-PS | 9.58 (1.07) | 9.67 (1.07) | 9.71 (1.07) |
| Hexyl acetylester substituted polystyrene | Hex-COO-PS | 9.38 (1.04) | 9.46 (1.04) | 9.51 (1.04) |
| Phenyl acetylester substituted polystyrene | Ph-COO-PS | 10.02 (1.15) | 10.03 (1.15) | 10.03 (1.15) |
| Benzyl acetylester substituted polystyrene | Ben-COO-PS | 10.51 (1.2) | 10.53 (1.2) | 10.54 (1.2) |

*PS = Polystyrene
**Number in parenthesis is the density in $g/cm^3$ used in determining the solubility parameter

TABLE 13

Solubility Parameters of Random Copolymers of Styrene and Substituted Styrene (Part 1)

| Degree of Substitution (%) | Solubility Parameter [$(cal/cm^3)^{1/2}$] | | | | |
|---|---|---|---|---|---|
| | PS-co-NO2-PS | PS-co-Cl-PS | PS-co-Br-PS | PS-co-CN-PS | PS-co-Ph—CO-PS |
| 0 | 8.96 | 8.96 | 8.96 | 8.96 | 8.96 |
| 10 | 9.05 | 9.07 | 9.08 | 9.18 | 8.98 |
| 20 | 9.14 | 9.19 | 9.20 | 9.40 | 9.00 |
| 30 | 9.23 | 9.30 | 9.31 | 9.61 | 9.02 |
| 40 | 9.32 | 9.42 | 9.43 | 9.83 | 9.04 |
| 50 | 9.41 | 9.53 | 9.55 | 10.0 | 9.06 |
| 60 | 9.50 | 9.65 | 9.67 | 10.3 | 9.08 |
| 70 | 9.59 | 9.76 | 9.78 | 10.5 | 9.10 |
| 80 | 9.68 | 9.87 | 9.90 | 10.7 | 9.12 |
| 90 | 9.77 | 9.99 | 10.0 | 10.9 | 9.14 |
| 100 | 9.86 | 10.1 | 10.1 | 11.1 | 9.16 |
| 150 | 9.97 | 10.4 | 10.9 | 11.7 | — |
| 200 | 10.1 | 10.8 | 11.7 | 12.3 | — |
| 250 | 10.1 | 11.4 | 12.3 | 12.7 | — |
| 300 | 10.2 | 11.9 | 12.9 | 13.1 | — |

TABLE 14

Solubility Parameters of Random Copolymers of Styrene and Substituted Styrene (Part 2)

| Degree of Substitution (%) | Solubility Parameter [(cal/cm³)$^{1/2}$] | | | | |
|---|---|---|---|---|---|
| | PS-co-Me-CO-PS | PS-co-Et-CO-PS | PS-co-Pr-CO-PS | PS-co-Bu-CO-PS | PS-co-Pen-CO-PS |
| 0 | 8.96 | 8.96 | 8.96 | 8.96 | 8.96 |
| 10 | 9.01 | 9.01 | 9.01 | 9.00 | 8.97 |
| 20 | 9.07 | 9.07 | 9.07 | 9.05 | 8.98 |
| 30 | 9.12 | 9.12 | 9.12 | 9.09 | 8.99 |
| 40 | 9.17 | 9.17 | 9.17 | 9.13 | 9.00 |
| 50 | 9.22 | 9.22 | 9.22 | 9.18 | 9.01 |
| 60 | 9.28 | 9.28 | 9.28 | 9.22 | 9.02 |
| 70 | 9.33 | 9.33 | 9.33 | 9.26 | 9.03 |
| 80 | 9.38 | 9.38 | 9.38 | 9.31 | 9.04 |
| 90 | 9.43 | 9.43 | 9.44 | 9.35 | 9.05 |
| 100 | 9.49 | 9.49 | 9.49 | 9.39 | 9.06 |

TABLE 15

Solubility Parameters of Random Copolymers of Styrene and Substituted Styrene (Part 3)

| Degree of Substitution (%) | Solubility Parameter [(cal/cm³)$^{1/2}$] | | | | |
|---|---|---|---|---|---|
| | PS-co-Me-COO-PS | PS-co-Bu-COO-PS | PS-co-Hex-COO-PS | PS-co-Ph-COO-PS | PS-co-Ben-COO-PS |
| 0 | 8.96 | 8.96 | 8.96 | 8.96 | 8.96 |
| 10 | 9.03 | 9.02 | 9.00 | 9.07 | 9.11 |
| 20 | 9.11 | 9.08 | 9.04 | 9.17 | 9.27 |
| 30 | 9.18 | 9.15 | 9.09 | 9.28 | 9.42 |
| 40 | 9.26 | 9.21 | 9.13 | 9.38 | 9.58 |
| 50 | 9.33 | 9.27 | 9.17 | 9.49 | 9.73 |
| 60 | 9.41 | 9.33 | 9.21 | 9.60 | 9.89 |
| 70 | 9.48 | 9.39 | 9.25 | 9.70 | 10.04 |
| 80 | 9.56 | 9.46 | 9.29 | 9.81 | 10.20 |
| 90 | 9.63 | 9.52 | 9.34 | 9.92 | 10.35 |
| 100 | 9.71 | 9.58 | 9.38 | 10.02 | 10.51 |
| 150 | 9.73 | 9.62 | 9.42 | 10.02 | 10.52 |
| 200 | 9.76 | 9.67 | 9.46 | 10.03 | 10.53 |
| 250 | 9.78 | 9.69 | 9.48 | 10.03 | 10.53 |
| 300 | 9.79 | 9.71 | 9.50 | 10.03 | 10.54 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a) a topsheet;
    b) a backsheet joined with the topsheet;
    c) an absorbent core interposed between the topsheet and backsheet; and
    d) an article element;
    wherein the article element comprises a slow recovery stretch laminate exhibiting an unload force at 37° C. of 0.16 N/(g/m) or greater and a percent of initial strain after 15 seconds of recovery at 22° C. of 10% or greater;
    wherein the slow recovery stretch laminate comprises an elastic member having an order-disorder temperature (ODT) of greater than 135° C.;
    wherein the elastic member comprises an hydrogenated block copolymer elastomer comprising at least one soft block and at least two hard blocks; and
    wherein the slow recovery stretch laminate has a force retention factor of greater than 3 for at least two of four hold strains (selected from hold strains of 200%, 150%, 100%, and 60%) under Normalized Unload Force at 37° C. (99° F.).

2. The absorbent article of claim 1 wherein the ODT is greater than 150° C.

3. The absorbent article of claim 1 wherein the elastic member comprises a blend of elastomers.

4. The absorbent article of claim 1 wherein the hydrogenated block copolymer elastomer comprises at least two substantially polystyrene hard blocks.

5. The absorbent article of claim 1 wherein the ODT is greater than 170° C.

6. The absorbent article of claim 4 wherein the hydrogenated block copolymer elastomer is hydrogenated in the soft block.

7. The absorbent article of claim 1 wherein the article element is selected from the group consisting of an anal cuff, an elasticized topsheet, a fastening system, a leg cuff, a waist elastic feature, a side panel, an ear, an outer cover, and combinations thereof.

8. The absorbent article of claim 1 wherein the slow recovery stretch laminate exhibits a percent of initial strain after 15 seconds of recovery at 22° C. of 20% or greater.

9. The absorbent article of claim 1 wherein the slow recovery stretch laminate exhibits a percent of initial strain after 15 seconds of recovery at 37° C., wherein the difference of the percent of initial strain after 15seconds of recovery at 22° C. and the percent of initial strain after 15 seconds of recovery at 37° C. is greater than 5%.

10. The absorbent article of claim 1 wherein the article element comprises:
 at least a first substrate having a first surface and a second surface; and
 at least one elastic member joined or attached to the first surface of the substrate.

11. The absorbent article of claim 10 wherein the article element comprises a second substrate having a first surface and a second surface, wherein the elastic member is joined to the first surface of the second substrate such that the elastic member is disposed between the first substrate and the second substrate.

12. The absorbent article of claim 10 wherein the article element is joined or attached to the first surface of the substrate via a method selected from the group consisting of adhesive bonding, thermal bonding, pressure bonding, ultrasonic bonding, and combinations thereof.

13. The absorbent article of claim 1 wherein at least one of the elastic member or the slow recovery stretch laminate comprises:
 a) 20% to 100% of at least one hydrogenated block copolymer elastomer comprising at least one soft block and at least two hard blocks;
 b) optionally, 0.01% to 60% of at least one modifying resin; and
 c) optionally, 0.01% to 60% of at least one additive.

14. The absorbent article of claim 6 wherein the hydrogenated block copolymer elastomer is hydrogenated greater than 90 mole percent of the soft block.

15. The absorbent article of claim 13 wherein the modifying resin is selected from a group comprising unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof.

16. The absorbent article of claim 10 wherein the elastic member is in a form selected from a group comprising a film, a strand, a band, a cross-hatch array, a foam, and combinations thereof.

17. The absorbent article of claim 10 wherein the first substrate is selected from a group comprising nonwoven webs, woven webs, knitted fabrics, films, film laminates, apertured films, nonwoven laminates, sponges, foams, scrims, and combinations thereof.

18. The absorbent article of claim 1 wherein the absorbent article is selected from a group comprising diapers, training pants, pull-on garments, refastenable pants, adult incontinence products, or feminine care products.

19. An article comprising:
 a slow recovery stretch laminate comprising an elastic member comprising an hydrogenated block copolymer elastomer comprising at least one soft block and at least two hard blocks;
 wherein the slow recovery stretch laminate exhibits an unload force at 37° C. of 0.16 N/(g/m) or greater and a percent of initial strain after 15 seconds of recovery at 22° C. of 10% or greater;
 wherein the elastic member exhibits an ODT of greater than about 135° C.; and
 wherein the slow recovery stretch laminate has a force retention factor of greater than 5 for at least two of four hold strains (selected from hold strains of 200%, 150%, 100%, and 60%) under Normalized Unload Force at 37° C. (99° F.).

20. An article comprising:
 a slow recovery elastomer comprising an hydrogenated block copolymer elastomer comprising at least one soft block and at least two hard blocks;
 wherein the slow recovery elastomer exhibits a normalized unload force of greater than 0.07N at 37° C. and 60% hold strain, and a percent of initial strain after 15seconds of recovery at 22° C. of 10% or greater;
 wherein the slow recovery elastomer exhibits an ODT of greater than 135° C.; and
 wherein the slow recovery stretch laminate has a force retention factor of greater than 3 for at least three of four hold strains (selected from hold strains of 200%, 150%, 100%, and 60%) under Normalized Unload Force at 37° C. (99° F.).

* * * * *